(12) United States Patent
Iimura et al.

(10) Patent No.: US 9,133,309 B2
(45) Date of Patent: Sep. 15, 2015

(54) ORGANOPOLYSILOXANE COPOLYMER

(75) Inventors: Tomohiro Iimura, Sodegaura (JP);
Akito Hayashi, Ichihara (JP); Seiki Tamura, Ichihara (JP); Haruhiko Furukawa, Chiba (JP)

(73) Assignee: DOW CORNING TORAY CO., LTD., Chiyoda-Ku, Tokyo (JP)

( * ) Notice: Subject to any disclaimer, the term of this patent is extended or adjusted under 35 U.S.C. 154(b) by 0 days.

(21) Appl. No.: 13/503,447

(22) PCT Filed: Oct. 22, 2010

(86) PCT No.: PCT/JP2010/069237
§ 371 (c)(1),
(2), (4) Date: Jul. 9, 2012

(87) PCT Pub. No.: WO2011/049246
PCT Pub. Date: Apr. 28, 2011

(65) Prior Publication Data
US 2012/0269747 A1    Oct. 25, 2012

(30) Foreign Application Priority Data
Oct. 23, 2009 (JP) ................. 2009-244976

(51) Int. Cl.
| | | |
|---|---|---|
| C07F 7/08 | (2006.01) |
| A61K 8/25 | (2006.01) |
| A61K 8/31 | (2006.01) |
| A61K 47/00 | (2006.01) |
| C08G 77/46 | (2006.01) |
| A61Q 19/00 | (2006.01) |
| C08G 77/12 | (2006.01) |
| C08G 77/20 | (2006.01) |
| C08G 77/50 | (2006.01) |
| C08L 83/12 | (2006.01) |
| A61K 8/893 | (2006.01) |
| A61Q 1/10 | (2006.01) |
| A61Q 15/00 | (2006.01) |
| A61Q 17/04 | (2006.01) |
| A61Q 19/10 | (2006.01) |
| A61Q 1/02 | (2006.01) |
| A61Q 13/00 | (2006.01) |
| A61Q 19/08 | (2006.01) |

(52) U.S. Cl.
CPC ............... *C08G 77/46* (2013.01); *A61K 8/893* (2013.01); *A61Q 19/00* (2013.01); *C08G 77/12* (2013.01); *C08G 77/20* (2013.01); *C08G 77/50* (2013.01); *C08L 83/12* (2013.01); *A61Q 1/02* (2013.01); *A61Q 1/10* (2013.01); *A61Q 13/00* (2013.01); *A61Q 15/00* (2013.01); *A61Q 17/04* (2013.01); *A61Q 19/08* (2013.01); *A61Q 19/10* (2013.01)

(58) Field of Classification Search
CPC ............................. C08G 18/289; A61K 8/893
USPC .................. 528/10, 32, 33; 524/858
See application file for complete search history.

(56) References Cited

U.S. PATENT DOCUMENTS

| | | | |
|---|---|---|---|
| 4,431,789 A | 2/1984 | Okazaki et al. | |
| 4,616,076 A | 10/1986 | Ona et al. | |
| 4,631,208 A | 12/1986 | Westall | |
| 4,698,178 A | 10/1987 | Huttinger et al. | |
| 5,144,054 A | 9/1992 | Shioya et al. | |
| 5,472,686 A | 12/1995 | Tsubaki et al. | |
| 5,484,950 A * | 1/1996 | Crivello | 549/215 |
| 5,654,362 A | 8/1997 | Schulz, Jr. et al. | |
| 5,660,819 A | 8/1997 | Tsubaki et al. | |
| 5,874,069 A | 2/1999 | Mendolia et al. | |
| 5,889,108 A | 3/1999 | Zhang | |
| 5,919,441 A | 7/1999 | Mendolia et al. | |
| 5,929,163 A | 7/1999 | Harashima | |
| 5,981,680 A | 11/1999 | Petroff et al. | |
| 6,168,782 B1 | 1/2001 | Lin et al. | |

(Continued)

FOREIGN PATENT DOCUMENTS

| | | |
|---|---|---|
| CA | 2291284 A1 | 5/2000 |
| EP | 1031592 A2 | 8/2000 |

(Continued)

OTHER PUBLICATIONS

Murthy et al. (Biomacromolecules, published 2007, pp. 3244-3252).*

(Continued)

*Primary Examiner* — Richard Schnizer
*Assistant Examiner* — Alma Pipic
(74) *Attorney, Agent, or Firm* — Howard & Howard Attorneys PLLC

(57) ABSTRACT

A novel organopolysiloxane copolymer is disclosed. The copolymer has excellent surface active power and exhibits excellent blending stability in cosmetic preparations and excellent feeling improvement characteristics in comparison to conventionally known polyether-modified silicones and silicone-containing alternating copolymers. The organopolysiloxane copolymer can be used in combination with various cosmetic formulation ingredients. The copolymer is an AB-type organopolysiloxane copolymer which has a silylalkyl group having a carbosiloxane dendrimer structure at one end of the molecular chain, and a hydrophilic segment at the other end. A method for producing the AB-type organopolysiloxane copolymer; a surfactant and a powder processing agent which are respectively composed of the organopolysiloxane copolymer; and a composition for external application and a cosmetic formulation which respectively contain the organopolysiloxane copolymer are also disclosed.

14 Claims, 2 Drawing Sheets

(56) References Cited

U.S. PATENT DOCUMENTS

| | | |
|---|---|---|
| 6,184,407 B1 | 2/2001 | Yoshitake et al. |
| 6,534,072 B2 | 3/2003 | Mondet et al. |
| 6,576,623 B1 | 6/2003 | Nakanishi et al. |
| 6,660,281 B1 | 12/2003 | Nakanishi et al. |
| 7,001,971 B2 | 2/2006 | Nakanishi |
| 7,482,419 B2 | 1/2009 | Caprasse et al. |
| 7,507,775 B2 | 3/2009 | Leatherman et al. |
| 7,601,680 B2 | 10/2009 | Wang et al. |
| 7,612,051 B2 | 11/2009 | Kamei et al. |
| 7,655,744 B2 | 2/2010 | Miyanaga |
| 7,771,709 B2 | 8/2010 | Nakanishi et al. |
| 7,998,903 B2 | 8/2011 | Nakanishi et al. |
| 8,034,891 B2 | 10/2011 | Okawa |
| 8,080,239 B2 | 12/2011 | Matsuo et al. |
| 2005/0261133 A1 | 11/2005 | Nakanishi et al. |
| 2009/0203802 A1 | 8/2009 | Kamei et al. |
| 2010/0190871 A1 | 7/2010 | Araki et al. |
| 2011/0182846 A1 | 7/2011 | Ikeda et al. |
| 2012/0269748 A1 | 10/2012 | Tamura et al. |
| 2012/0269875 A1 | 10/2012 | Tamura et al. |

FOREIGN PATENT DOCUMENTS

| | | | |
|---|---|---|---|
| EP | 2014701 A2 | | 1/2009 |
| EP | 2174985 A1 | | 4/2010 |
| EP | 2180028 | * | 4/2010 |
| EP | 2180028 A1 | | 4/2010 |
| JP | 50004199 A | * | 1/1975 |
| JP | 57139123 A | * | 8/1982 |
| JP | 57-149290 A | | 9/1982 |
| JP | 61-090732 A | | 5/1986 |
| JP | 61-123635 A | | 6/1986 |
| JP | 61-127733 A | | 6/1986 |
| JP | 61-293903 A | | 12/1986 |
| JP | 61-293904 A | | 12/1986 |
| JP | 62034039 B | | 7/1987 |
| JP | 62-187406 A | | 8/1987 |
| JP | 62-195389 A | | 8/1987 |
| JP | 62-215510 A | | 9/1987 |
| JP | 62-216635 A | | 9/1987 |
| JP | 04-108795 A | | 4/1992 |
| JP | 4134013 A | | 5/1992 |
| JP | 04-211605 A | | 8/1992 |
| JP | 04-234307 A | | 8/1992 |
| JP | 05-112424 A | | 5/1993 |
| JP | 05-163436 A | | 6/1993 |
| JP | 05-186596 A | | 7/1993 |
| JP | 05-311076 A | | 11/1993 |
| JP | 06-157236 A | | 6/1994 |
| JP | 06-305933 A | | 11/1994 |
| JP | 6089147 B | | 11/1994 |
| JP | 07-033622 A | | 2/1995 |
| JP | 07-100358 A | | 4/1995 |
| JP | 07-187945 A | | 7/1995 |
| JP | 08-217626 A | | 8/1996 |
| JP | 08-268831 A | | 10/1996 |
| JP | 08-268832 A | | 10/1996 |
| JP | 02-583412 B2 | | 2/1997 |
| JP | 09-071504 A | | 3/1997 |
| JP | 09-194323 A | | 7/1997 |
| JP | 09-194594 A | | 7/1997 |
| JP | 02-719303 B2 | | 2/1998 |
| JP | 10-167946 A | | 6/1998 |
| JP | 10-245317 A | | 9/1998 |
| JP | 10-310504 A | | 11/1998 |
| JP | 10-310505 A | | 11/1998 |
| JP | 10-310506 A | | 11/1998 |
| JP | 10-310507 A | | 11/1998 |
| JP | 10-310508 A | | 11/1998 |
| JP | 10-310509 A | | 11/1998 |
| JP | 10-316536 A | | 12/1998 |
| JP | 07-025728 A | | 1/1999 |
| JP | 11-049957 A | | 2/1999 |
| JP | 2000-063225 A | | 2/2000 |
| JP | 2000-072784 A | | 3/2000 |
| JP | 2000-239390 A | | 9/2000 |
| JP | 2001-011281 A | | 1/2001 |
| JP | 2001-039819 A | | 2/2001 |
| JP | 2001-072891 A | | 3/2001 |
| JP | 2001-316473 A | | 11/2001 |
| JP | 2002-038013 A | | 2/2002 |
| JP | 2002-179797 A | | 6/2002 |
| JP | 2002-179798 A | | 6/2002 |
| JP | 2004-169015 A | | 6/2004 |
| JP | 2004-182680 A | | 7/2004 |
| JP | 2004-231608 A | | 8/2004 |
| JP | 2004-339244 A | | 12/2004 |
| JP | 2005-042097 A | | 2/2005 |
| JP | 2005-089494 A | | 4/2005 |
| JP | 2005-194523 A | | 7/2005 |
| JP | 2005-344076 A | | 12/2005 |
| JP | 2006-218472 A | | 8/2006 |
| JP | 2007-532754 A | | 11/2007 |
| JP | 2009-511710 A | | 3/2009 |
| JP | 2009-511712 A | | 3/2009 |
| WO | WO 03/041664 A1 | | 5/2003 |
| WO | WO 03/075864 A1 | | 9/2003 |
| WO | WO 2007/135771 A1 | | 11/2007 |
| WO | WO 2009/022621 A1 | | 2/2009 |
| WO | WO 2009/025146 A1 | | 2/2009 |

OTHER PUBLICATIONS

International Search Report for Application No. PCT/JP2010/069237 dated Jan. 11, 2011, 6 pages.
International Search Report for Application No. PCT/JP2010/069249 dated Jan. 11, 2011, 6 pages.
International Search Report for Application No. PCT/JP2010/069248 dated Jan. 11, 2011, 4 pages.
Supplementary European Search Report for Application No. EP 10 82 5093 dated May 16, 2013; 2 pages.
Supplementary European Search Report for Application No. EP 10 82 5094 completed on Dec. 11, 2013, 2 pages.

* cited by examiner

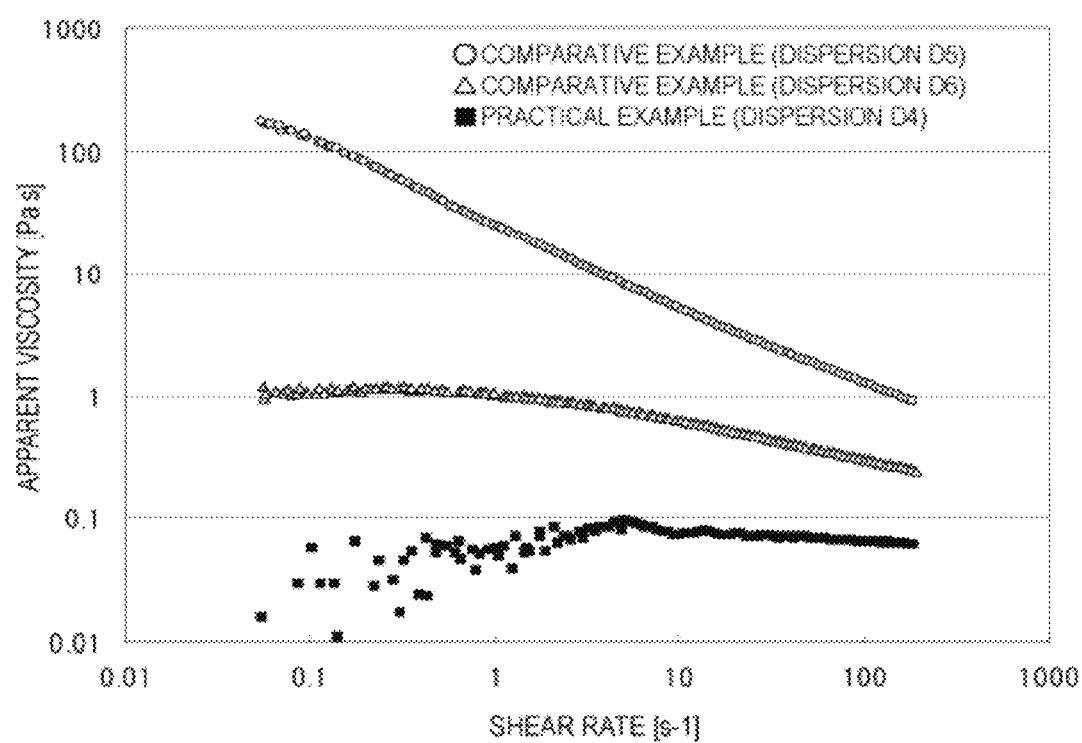

ORGANOPOLYSILOXANE COPOLYMER

RELATED APPLICATIONS

This application claims priority to and all the advantages of International Patent Application No. PCT/JP2010/069237, filed on Oct. 22, 2010, which claims priority to Japanese Patent Application No. JP2009-244976, filed on Oct. 23, 2009.

TECHNICAL FIELD

The present invention relates to a novel AB-type organopolysiloxane copolymer and a method of manufacturing the same; a surfactant and a powder treatment agent comprising the organopolysiloxane copolymer; and a topical composition and a cosmetic composition comprising the organopolysiloxane copolymer.

BACKGROUND ART

Organopolysiloxane derivatives are proactively compounded as cosmetic composition-use oil solutions for the purpose of reducing stickiness and oiliness of cosmetics. However, polydimethyl siloxanes have structural characteristics that lead to poor compatibility with skin, resulting in a multitude of problems such as insufficient moisturizing.

In order to solve these problems extensive research has been conducted into imparting surface activity and improved feel to a polyorgano-polysiloxane through introducing a polyoxyethylene group and/or a polyglyceryl group into the dimethylpolysiloxane (e.g. Patent Documents 1 and 2). JP-S-61-123635 and the like describe a graft-type polyoxyethylene-modified silicone and JP-S-57-149290 and the like describe a polyglyceryl-modified silicone which are produced by addition reacting a polyether compound having an allyl group on an end thereof with the SiH group of an organohydrogenpolysiloxane via a hydrosilylation reaction. However, generally, because an organohydrogenpolysiloxane with a large degree of polymerization is frequently used as a raw material, the feel derived from the silicone becomes excessively strong and there are cases in which a natural feel cannot be obtained. Furthermore, because the polyorgano-polysiloxane as a raw material is nothing more than the mean structure, unmodified polyorgano-polysiloxane in which the polyoxyethylene group and the polyglyceryl group are not bonded is produced as an unavoidable by-product or remains in the system. As a result, compatibility with compounded cosmetic raw materials is negatively affected, which may lead to heterogeneity of the system, a cloudy visual appearance, and a decline in emulsion stability.

Additionally, JP-H-04-211605 and the like propose an (AB)n-type organopolysiloxane copolymer in which the silicone unit and the polyoxyethylene unit are alternately bonded (Patent Documents 3 to 5). Additionally, JP-H-2005-042097 and the like propose an (AB)n-type organopolysiloxane copolymer in which the silicone unit and the polyglycerine unit are alternately bonded (Patent Document 6). The amount of unreacted polyorgano-polysiloxane can be reduced because these alternating copolymers have repeating units and, moreover, when used as a cosmetic composition component, are an extremely useful cosmetic raw material because they impart superior feel.

However, in many cases alternating copolymers are synthesized via balance reactions and, as a result, the molecular weight of the alternating copolymer tends to increase. This leads to a problem in that the obtained surface activity and compatibility is suppressed, and thus, further improvement is needed. Additionally, for the same reason, there is need for further improvement in compatibility with compounded cosmetic raw materials.

On the other hand, AB-type or ABA-type organopolysiloxane copolymers have been proposed in which molecular weight is suppressed and only two or three of the silicone units, having a relatively simple molecular design, and the polyether units such as the polyoxyethylene units are bonded. These organopolysiloxane copolymers comprise hydrophobic silicone units and hydrophilic units and, therefore, are suggested to be useful as surfactants and cosmetic raw materials (Patent Documents 7 to 10). However, with these organopolysiloxane copolymers, when the hydrophobic siloxane unit becomes short, while hydrolysis resistance with respect to liquid change improves, the hydrophobicity and water repellency in the molecule of the same copolymer unavoidably decline and, in some cases, properties as a surfactant and emulsion stability become insufficient. On the other hand, while it is possible to two-dimensionally extend the siloxane chain length, and increase the hydrophobicity of the subject portion, there are cases where the feel derived from silicone as the cosmetic raw material strengthens, and a natural feel cannot be obtained. Additionally, in cases when a long chain siloxane portion is included, in addition to the issue related to feel described above, there are cases where compatibility with other cosmetic raw material components is negatively affected. In particular, when a long chain siloxane portion is mixed with an acidic cosmetic raw material, the long chain siloxane portion is prone to degradation. Thus, there is further need for an organopolysiloxane copolymer that is more useful as a surfactant and cosmetic raw material.

Patent Document 1: Japanese Unexamined Patent Application Publication No. S-61-123635A (Publication No. JP-S-63-016414)

Patent Document 2: Japanese Unexamined Patent Application Publication No. S-57-149290A (Publication No. JP-S-62-034039)

Patent Document 3: Japanese Unexamined Patent Application Publication No. H-04-211605A (Patent No. 3061434B)

Patent Document 4: Japanese Unexamined Patent Application Publication No. H-04-234307A (Patent No. 3071222B)

Patent Document 5: Japanese Unexamined Patent Application Publication No. H-05-163436A (Patent No. 3283277B)

Patent Document 6: Japanese Unexamined Patent Application Publication No. 2005-042097A Patent Document 7: Japanese Unexamined Patent Application Publication No. 2005-344076A Patent Document 8: Japanese Unexamined Patent Application Publication No. S-62-195389A (Patent No. 2583412B)

Patent Document 9: Japanese Unexamined Patent Application Publication (Translation of PCT Application) No. 2009-511710A Patent Document 10: Japanese Unexamined Patent Application Publication (Translation of PCT Application) No. 2009-511712A

DISCLOSURE OF THE INVENTION

Summary of the Invention

In order to resolve the problems described above, an object of the present invention is to provide a novel AB-type organopolysiloxane copolymer that, compared with conventional polyether-modified silicones and silicone-based alternating copolymers, has superior compounding stability in cosmetics and feeling to touch improvement characteristics, can be used in combination with a wide range of cosmetic ingredients, and that has superior surface activity. Furthermore, an object of the present invention is to provide a surfactant or a powder treatment agent comprising the organopolysiloxane copolymer, and a topical composition, particularly a cosmetic composition, comprising the organopolysiloxane copolymer.

Means to Resolve the Problems

As a result of intensive investigation aimed at solving the above problems, the present inventors arrived at the present invention. That is, the objects of the present invention are achieved by an AB-type organopolysiloxane copolymer having a silylalkyl group having a carbosiloxane dendrimer structure on one terminal and a hydrophilic segment on the other terminal of the molecular chain; a surfactant or powder treatment agent comprising the organopolysiloxane copolymer; and a topical composition, particularly a cosmetic composition, comprising the organopolysiloxane copolymer.

More specifically, the objects of the present invention are achieved by an organopolysiloxane copolymer expressed by general formula (1) below; a surfactant or powder treatment agent comprising the organopolysiloxane copolymer; and a topical composition, particularly a cosmetic composition, comprising the organopolysiloxane copolymer.

General Formula (1):

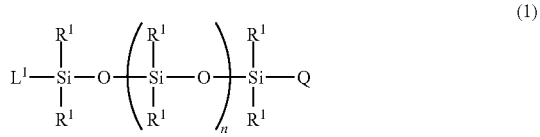

(1)

In general formula (1), $R^1$ independently represents an aryl group or an alkyl group having from 1 to 10 carbons, $L^1$ is a silyl alkyl group expressed by the following general formula (2) when i=1, Q is a hydrophilic segment, and n is a number in a range of 0 to 10.

General Formula (2):

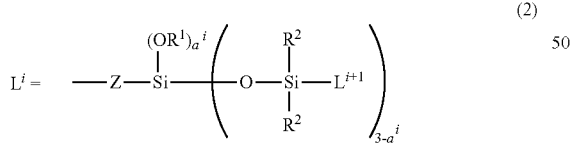

(2)

In general formula (2), $R^2$ is a phenyl group or an alkyl group having from 1 to 6 carbons, and Z is a divalent organic group. i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c. $a^i$ is a number in a range of 0 to 3.

Yet more specifically, the objects described above are achieved by, firstly, the invention of the AB-type organopolysiloxane copolymer having a silylalkyl group having a carbosiloxane dendrimer structure on one terminal and a hydrophilic segment on the other terminal of the molecular chain, described in [1] to [7] below.

[1] An organopolysiloxane copolymer expressed by the following general formula (1):

General Formula (1):

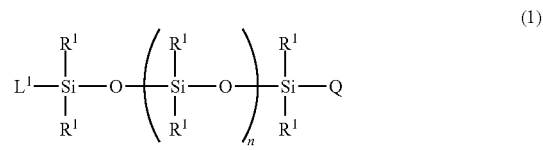

(1)

In general formula (1), $R^1$ independently represents an aryl group or an alkyl group having from 1 to 10 carbons, $L^1$ is a silyl alkyl group expressed by the following general formula (2) when i=1, Q is a hydrophilic segment, and n is a number in a range of 0 to 10.

General Formula (2):

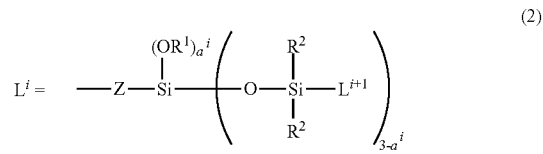

(2)

In general formula (2), $R^1$ is synonymous with the group described above, $R^2$ is a phenyl group or an alkyl group having from 1 to 6 carbons, Z is a divalent organic group. i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c. $a^i$ is a number in a range of 0 to 3.

[2] The organopolysiloxane copolymer described in [1], wherein in the general formula (1), $L^1$ is a functional group expressed by the following general formula (2-1) or general formula (2-2).

General Formula (2-1):

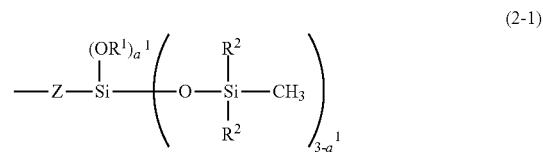

(2-1)

General Formula (2-2):

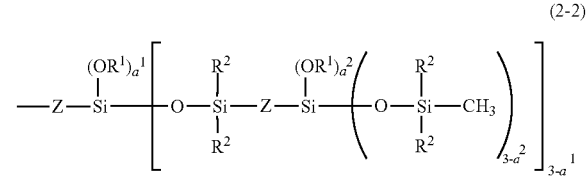

(2-2)

In these formulae, $R^1$, $R^2$, and Z are synonymous with the groups described above, and $a^1$ and $a^2$ are each independently numbers in a range of 0 to 3.

[3] The organopolysiloxane copolymer described in [1] or [2], wherein in the general formula (1), Q is bonded to the silicon atom via a linking group that is at least divalent, and is a hydrophilic segment comprising at least one hydrophilic unit selected from hydrophilic units expressed by the following structural formulae (3-1) to (3-4).

Formula 5

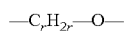

(3-1)

In structural formula 3-1, r is a number in a range of 1 to 6.

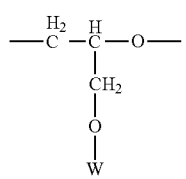

(3-2)

In structural formula 3-2, W is a hydrogen atom or an alkyl group having from 1 to 20 carbons.

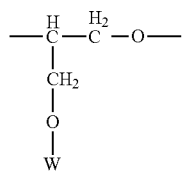

(3-3)

In structural formula 3-3, W is synonymous with the group described above.

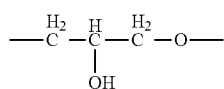

(3-4)

[4] The organopolysiloxane copolymer described any one of [1] to [3], wherein in the general formula (1), Q is a hydrophilic segment bonded to the silicon atom via a linking group that is at least divalent, comprising at least one linearly bonded hydrophilic unit selected from hydrophilic units expressed by the following structural formulae (3-1) to (3-4); or Q is a hydrophilic group bonded to the silicon atom via a linking group that is at least divalent, comprising at least one hydrophilic unit selected from hydrophilic units expressed by structural formulae (3-1) to (3-4) above, and a branch unit selected from groups expressed by structural formulae (3-5) to (3-7) below.

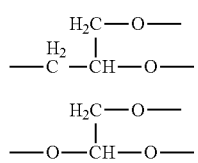

(3-5)

(3-6)

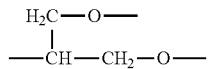

(3-7)

[5] The organopolysiloxane copolymer described in any one of [1] to [4], wherein in the general formula (1), Q is a hydrophilic segment expressed by general formulae (4-1) to (4-4) below.

General Formula (4-1):

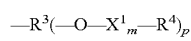

(4-1)

In this formula, $R^3$ is an organic group having (p+1) valency, and p is a number that is greater than or equal to 1. $X^1$ are each independently at least one hydrophilic unit selected from the hydrophilic units expressed by the general formulae (3-1) to (3-4) above, and m is a number in a range of 1 to 100. $R^4$ is a hydrogen atom or a group selected from the group consisting of acyl groups, glycidyl groups, and alkyl groups having from 1 to 20 carbons.

General Formula (4-2):

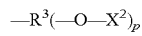

(4-2)

In this formula, $R^3$ is a group synonymous with the groups described above, and p is a number synonymous with the number described above and $X^2$ is a hydrophilic segment expressed by structural formula (4-2-1) below.

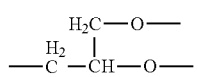

(4-2-1)

In structural formula (4-2-1), the at least one hydrophilic unit selected from the hydrophilic units expressed by the general formulae (3-1) to (3-4) is bonded to two oxygen atoms, each independently.

General Formula (4-3):

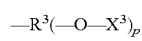

(4-3)

In this formula, $R^3$ is a group synonymous with the groups described above, and p is a number synonymous with the number described above and $X^3$ is a hydrophilic segment expressed by structural formula (4-3-1) below;

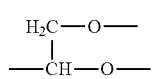

(4-3-1)

In structural formula (4-2-1), the at least one hydrophilic unit selected from the hydrophilic units expressed by the general formulae (3-1) to (3-4) is bonded to two oxygen atoms, each independently.

General Formula (4-4):

(4-4)

In this formula, $R^3$ is a group synonymous with the groups described above, and p is a number synonymous with the number described above and $X^4$ is a hydrophilic segment expressed by structural formula (4-4-1) below.

$$\begin{array}{c} H_2C-O-\\ |\\ -CH-CH_2-O- \end{array} \quad (4\text{-}4\text{-}1)$$

In structural formula (4-4-1), the at least one hydrophilic unit selected from the hydrophilic units expressed by the general formulae (3-1) to (3-4) is bonded to two oxygen atoms, each independently.

[6] The organopolysiloxane copolymer described in any one of [1] to [5], expressed by any one of structural formulae (1-1) to (1-4) below.

Structural Formula (1-1)

$$\left(H_3C-\underset{\underset{CH_3}{|}}{\overset{\overset{CH_3}{|}}{Si}}-O\right)_3-\underset{\underset{CH_3}{|}}{\overset{\overset{CH_3}{|}}{Si}}-R^5-\underset{\underset{CH_3}{|}}{\overset{\overset{CH_3}{|}}{Si}}-O-\left(\underset{\underset{CH_3}{|}}{\overset{\overset{CH_3}{|}}{Si}}-O\right)_n-\underset{\underset{CH_3}{|}}{\overset{\overset{CH_3}{|}}{Si}}-R'^3-O-X^1{}_m-R^4$$

Structural Formula (1-2)

$$\left(H_3C-\underset{\underset{CH_3}{|}}{\overset{\overset{CH_3}{|}}{Si}}-O\right)_3-\underset{\underset{CH_3}{|}}{\overset{\overset{CH_3}{|}}{Si}}-R^5-\underset{\underset{CH_3}{|}}{\overset{\overset{CH_3}{|}}{Si}}-O-\left(\underset{\underset{CH_3}{|}}{\overset{\overset{CH_3}{|}}{Si}}-O\right)_n-\underset{\underset{CH_3}{|}}{\overset{\overset{CH_3}{|}}{Si}}-R'^3-O-CH_2-\underset{\underset{H_2C-O-X^1{}_m-R^4}{|}}{CH}-O-X^1{}_m-R^4$$

Structural Formula (1-3)

$$\left(H_3C-\underset{\underset{CH_3}{|}}{\overset{\overset{CH_3}{|}}{Si}}-O\right)_3-\underset{\underset{CH_3}{|}}{\overset{\overset{CH_3}{|}}{Si}}-R^5-\underset{\underset{CH_3}{|}}{\overset{\overset{CH_3}{|}}{Si}}-O-\left(\underset{\underset{CH_3}{|}}{\overset{\overset{CH_3}{|}}{Si}}-O\right)_n-\underset{\underset{CH_3}{|}}{\overset{\overset{CH_3}{|}}{Si}}-R'^3-O-\underset{\underset{H_2C-O-X^1{}_m-R^4}{|}}{\overset{\overset{H}{|}}{C}}-O-X^1{}_m-R^4$$

Structural Formula (1-4)

$$\left(H_3C-\underset{\underset{CH_3}{|}}{\overset{\overset{CH_3}{|}}{Si}}-O\right)_3-\underset{\underset{CH_3}{|}}{\overset{\overset{CH_3}{|}}{Si}}-R^5-\underset{\underset{CH_3}{|}}{\overset{\overset{CH_3}{|}}{Si}}-O-\left(\underset{\underset{CH_3}{|}}{\overset{\overset{CH_3}{|}}{Si}}-O\right)_n-\underset{\underset{CH_3}{|}}{\overset{\overset{CH_3}{|}}{Si}}-R'^3-O-\underset{\underset{H_2C-O-X^1{}_m-R^4}{|}}{\overset{\overset{H}{|}}{C}}-O-X^1{}_m-R^4$$

In structural formulae (1-1) to (1-4), n is a number in a range from 0 to 10 and m is a number in a range from 1 to 100.

$X^1$ are each independently at least one hydrophilic unit selected from the hydrophilic units expressed by the general formulae (3-1) to (3-4) above.

$R'^3$ is a group selected from divalent organic groups expressed by general formulae (5-1), (5-1-2), (5-1-3), and (5-2) below.

$$-R^6- \quad (5\text{-}1)$$

(5-1-2)

(5-1-3)

$$-R^6-\overset{\overset{O}{\|}}{C}- \quad (5\text{-}2)$$

In this formula, $R^6$ may have a substituent, and are each independently a straight or branched chain alkylene group or alkenylene group having from 2 to 22 carbons, or an arylene group having from 6 to 22 carbons.

$R^4$ is a hydrogen atom or a group selected from the group consisting of acyl groups, glycidyl groups, and alkyl groups having from 1 to 20 carbons.

$R^5$ is a group selected from divalent organic groups expressed by general formulae (5-1) to (5-7) below.

$$-R^6- \quad (5\text{-}1)$$

$$-R^6-\overset{\overset{O}{\|}}{C}- \quad (5\text{-}2)$$

$$-R^6-\overset{\overset{O}{\|}}{C}-O-R^6- \quad (5\text{-}3)$$

$$-\overset{\overset{O}{\|}}{C}-R^6- \quad (5\text{-}4)$$

$$-R^6-\overset{\overset{O}{\|}}{C}-O-R^7- \quad (5\text{-}5)$$

$$-R^6-\overset{\overset{O}{\|}}{C}-\overset{\overset{H}{|}}{N}-R^7- \quad (5\text{-}6)$$

$$-R^6-R^7- \quad (5\text{-}7)$$

In these formulae, $R^6$ is a group synonymous with the groups described above; and $R^7$ is a group selected from divalent organic groups expressed by the following formulae.

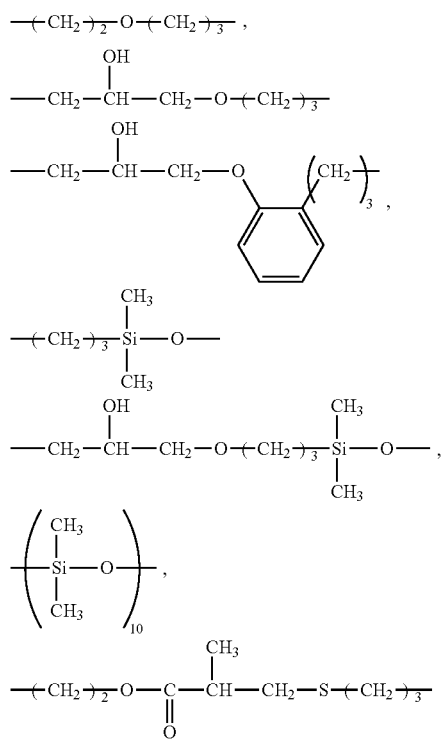

[7] The organopolysiloxane copolymer described in any one of [1] to [6], wherein n is equal to 0.

Another object of the present invention is achieved by the invention of a surfactant and an emulsion composition comprising the organopolysiloxane copolymer described in [8] to [8-2] below.

[8] A surfactant comprising the organopolysiloxane copolymer described in any one of [1] to [7].

[8-2] An emulsion composition comprising: (a-1) a surfactant comprising the organopolysiloxane copolymer described in any one of [1] to [7], (b) an oil agent selected from a silicone oil, a nonpolar organic compound, or a low polarity organic compound, and water.

Likewise, another object of the present invention is achieved by the invention of a powder treatment agent, a powder composition, and a powder in oil dispersion comprising the organopolysiloxane copolymer described in [9] to [9-5] below.

[9] A powder treatment agent comprising the organopolysiloxane copolymer described in any one of [1] to [7].

[9-1] A powder composition comprising: (a-2) a powder treatment agent comprising the organopolysiloxane copolymer described in any one of [1] to [7], and (d) a powder or a colorant.

[9-2] The powder composition described in [9-1], wherein from 1.0 to 30 parts by weight of (a-2) the powder treatment agent comprising the organopolysiloxane copolymer described in any one of [1] to [7] per 100 parts by weight of (d) the powder or the colorant are used to surface treat the component (d).

[9-3] The powder composition described in [9-1] or [9-2], wherein the component (d) is one or two or more selected from the group consisting of an inorganic pigment powder, an organic pigment powder, and a resin powder, having an average diameter in a range of 1 nm to 20 μm.

[9-4] The powder composition described in any one of [9-1] to [9-3], wherein part or all of the component (d) is a water-repellent treated powder or colorant.

[9-5] A powder in oil dispersion comprising: (a-2) the organopolysiloxane copolymer described in any one of [1] to [7], (d) a powder or a colorant, and (c) an oil agent selected from a silicone oil, a nonpolar organic compound, and a low polarity organic compound.

Furthermore, an object of the present invention is more preferably achieved by the invention of a topical composition, particularly the invention of a cosmetic composition, comprising the organopolysiloxane copolymer (including cases when compounded in the form of an emulsion composition, a powder composition, or a powder in oil dispersion as a raw material of the topical composition) described in [10] to [25].

[10] A topical composition comprising the organopolysiloxane copolymer described in any one of [1] to [7].

[11] The topical composition described in [10] that is a cosmetic composition or a medicament.

[12] The cosmetic composition described in [11] comprising the following components:

(a) from 0.1 to 99.9 wt. % of the organopolysiloxane copolymer described in any one of [1] to [7]; and (b) from 99.9 to 0.1 wt. % of a silicone oil, a nonpolar organic compound, or a low polarity organic compound.

[13] The cosmetic composition described in [12], wherein the component (b) is a silicone oil, more specifically a hydrophobic silicone oil having a viscosity at 25° C. of 0.65 to 100,000 mm²/s.

[14] The cosmetic composition described in [12], wherein the component (b) is a nonpolar organic compound or a low polarity organic compound, and said component (b) is a liquid at 5 to 100° C.

[15] The cosmetic composition described in [12] or [13], wherein a part or all of the silicone oil is a straight organopolysiloxane expressed by general formula (6), a cyclic organopolysiloxane expressed by general formula (7), or a branched organopolysiloxane expressed by general formula (8) below.

General Formula (6):

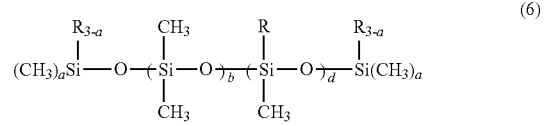

General Formula (7):

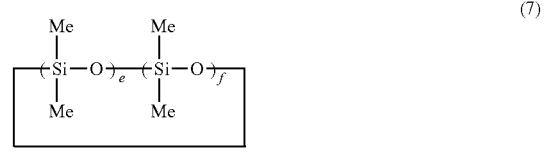

General Formula (8):

In the general formulae (6) to (8), Me is a methyl group, R is a hydrogen atom or a group selected from a hydroxyl group, or a monovalent nonsubstituted- or fluorine substituted-alkyl group having from 2 to 30 carbons, an aryl group, an amino substituted alkyl group, an alkoxy groups, and a group expressed by $(CH_3)_3SiO\{(CH_3)_2SiO\}_hSi(CH_3)_2CH_2CH_2—$.

a are each individually an integer from 0 to 3. b is an integer in a range from 0 to 1,000, d is an integer in a range from 0 to 1,000, and (b+d) is an integer in a range from 1 to 2,000. e and f are integers in a range from 0 to 8, and satisfy the relationship $3 \le e+f \le 8$. Additionally, g is an integer in a range of 1 to 4, and h is an integer in a range of 0 to 500.

[16] The cosmetic composition described in any one of [11] to [15], further comprising: (c) one or two or more selected from the group consisting of an anionic surfactant, a cationic surfactant, a nonionic surfactant, an amphoteric surfactant, and a semipolar surfactant.

[17] The cosmetic composition described in any one of [11] to [16], further comprising (d) a powder or a colorant.

[18] The cosmetic composition described in [17], wherein the component (d) is one or two or more selected from the group consisting of an inorganic pigment powder, an organic pigment powder, and a resin powder, having an average diameter in a range of 1 nm to 20 μm.

[19] The cosmetic composition described in [17] or [18], wherein part or all of the component (d) is a water-repellent treated powder or colorant.

[20] The cosmetic composition described in any one of [11] to [19], further comprising (e) a water-soluble polymer.

[21] The cosmetic composition described in any one of [11] to [20], further comprising (f) a silicone resin.

[22] The cosmetic composition described in any one of [11] to [21], further comprising (g) a silicone elastomer.

[23] The cosmetic composition described in any one of [11] to [22], further comprising: (h) an ultraviolet light blocking component.

[24] The cosmetic composition described in any one of [11] to [23], wherein the cosmetic composition is a skin care product, a cosmetic product for hair, an anti-perspirant product, a makeup product, or an ultraviolet light blocking product.

[25] The cosmetic composition described in any one of [11] to [24], wherein a form of a product is liquid, milk-like, cream-like, solid, paste-like, gel-like, powder-like, multilayer, mousse-like, or spray-like.

Moreover, an object of the present invention is preferably achieved by a method in which the organopolysiloxane copolymer is manufactured via a hydrosilylation reaction. The manufacturing method is described in detail in [26] below.

[26] A method for manufacturing the organopolysiloxane copolymer described in [1], comprising: addition reacting (A) an organopolysiloxane having silicon-bonded hydrogen atoms at both molecular terminals expressed by general formula (1') below, and (B) a compound having a carbosiloxane dendron structure that has one carbon-carbon double bond at a molecular terminal expressed by general formula (2') below (at an amount less than or equal to ½ a molar equivalent of the component (A)) in the presence of (C) a hydrosilylation reaction catalyst; and, thereafter, further addition reacting (D) a hydrophilic compound having one alkenyl group at a molecular terminal (at an amount less than or equal to ½ a molar equivalent of the component (A)).

General Formula (1'):

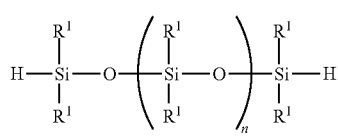

In general formula (1'), $R^1$ each independently represent an aryl group or an alkyl group having from 1 to 10 carbons, and n is a number in a range of 0 to 10.

General Formula (2'):

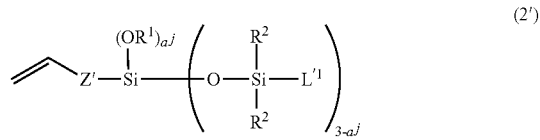

In general formula (2'), $L'^1$ is a methyl group or, when j=1, is a silylalkyl group expressed by general formula (2") below, and Z' is a divalent organic group.

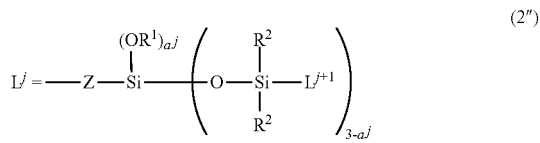

In general formula (2"), $R^2$ is a phenyl group or an alkyl group having from 1 to 6 carbons, and Z is a divalent organic group. j represents a generation of the silylalkyl group represented by $L^j$ and is an integer of 1 to c' when c' is a number of generations that is a number of repetitions of the silylalkyl group. The number of generations c' is an integer from 1 to 10, and $L^{j+1}$ is the silylalkyl group when j is less than c' and is a methyl group or a phenyl group when j=c'. $a^j$ is a number in a range from 0 to 3.

Effects of the Invention

According to the present invention, a novel organopolysiloxane copolymer can be provided that, compared with conventional polyether-modified silicones and silicone-based alternating copolymers, has superior compounding stability in cosmetics and feeling to touch improvement characteristics, can be used in combination with a wide range of cosmetic ingredients, and that has superior surface activity and powder treating capability. Furthermore, according to the present invention, a surfactant and a powder treatment agent formed from the organopolysiloxane copolymer, or a topical composition comprising said surfactant and powder treatment agent, particularly a cosmetic composition, can be provided.

BRIEF DESCRIPTION OF THE DRAWINGS

FIG. 2 is a chart showing evaluation results (Practical Example: Dispersion (D4)) of slurry-like dispersions (D4) to (D6) in which a mixed solution comprising decamethyl cyclopentasiloxane and trioctanoin at a ratio of 4:1 is used as a dispersing medium.

DETAILED DESCRIPTION OF THE INVENTION

Figure 1:
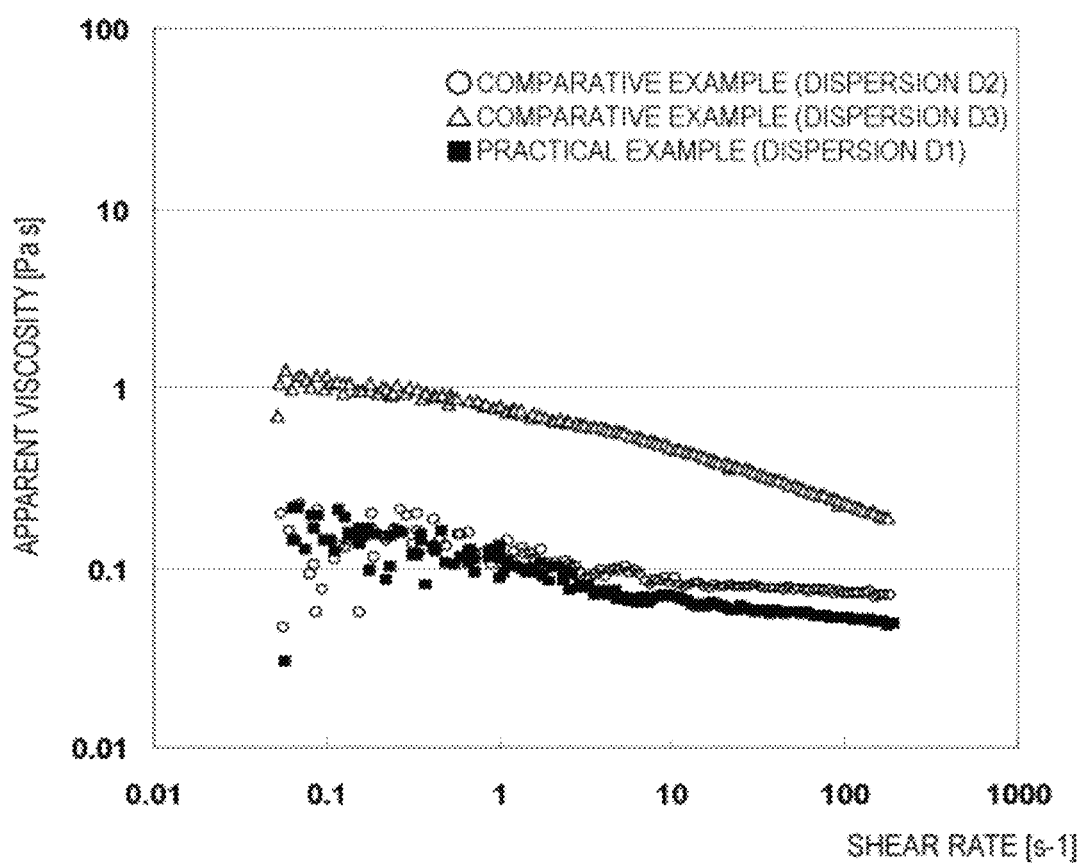
FIG. 1 is a chart showing evaluation results (Practical Example: Dispersion (D1)) of slurry-like dispersions (D1) to (D3) in which decamethyl cyclopentasiloxane was used as a dispersing medium.

A novel organopolysiloxane copolymer according to the present invention has a carbosiloxane dendrimer structure on one molecular terminal and a hydrophilic segment on the other terminal of the molecular chain, and specifically is an AB-type organopolysiloxane copolymer expressed by the following general formula (1) below. Hereinafter, the group represented by $L^1$ in general formula (1), which is a silylalkyl group expressed by the following general formula (2) when i=1, is also referred to as the "carbosiloxane dendrimer structure" and the "silylalkyl group having a carbosiloxane dendrimer structure".

General Formula (1):

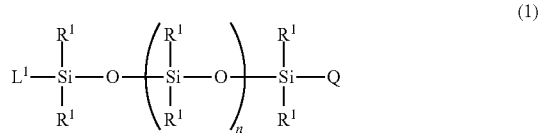

(1)

In general formula (1), $R^1$ independently represents an aryl group or an alkyl group having from 1 to 10 carbons. $L^1$ is a silylalkyl group expressed by the following general formula (2) when i=1, n is a number in a range from 0 to 10, and Q is a hydrophilic segment.

General Formula (2):

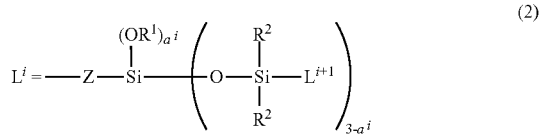

(2)

In general formula (2), $R^2$ is a phenyl group or an alkyl group having from 1 to 6 carbons, and Z is a divalent organic group. i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c. $a^i$ is a number in a range of 0 to 3.

In general formula (1), $R^1$ independently represents an aryl group or an alkyl group having from 1 to 6 carbons. Examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or annular alkyl groups. From a technical point of view, $R^1$ preferably is a methyl group or a phenyl groups. Preferably, n is a number in a range from 0 to 10 and, when the novel organopolysiloxane copolymer is used as a surfactant or a powder treatment agent, n preferably is a number in a range from 0 to 8 and more preferably a number in a range from 0 to 3. From the standpoint of obtaining chemical stability and superior surface activity effects and powder treatment effect, n is even more preferably 0 or 1. Note that when n is 0, the siloxane portion of the organopolysiloxane copolymer according to the present application, with the exception of the group represented by $L^1$ and the hydrophilic segment represented by Q, is a disiloxane structure. When n is 1, this siloxane portion is a trisiloxane structure.

In general formula (1), the group represented by $L^1$ is a silylalkyl group having a carbosiloxane dendrimer structure, and is defined as the silylalkyl group expressed by general formula (2) when i=1. The silylalkyl group having a carbosiloxane dendrimer structure has a structure where a carbosiloxane unit is extended in the form of a dendrimer and, thus, compared to a linear or simply branched polysiloxane unit, is a functional group that exhibits high water repellency; and, thus, a superior surfactant or powder treatment agent can be provided to the organopolysiloxane copolymer according to the present application without inhibiting the feeling to touch originating from the hydrophilic functional group. Additionally, the silylalkyl group having a carbosiloxane dendrimer structure is chemically stable, and for this reason, the silylalkyl group is a functional group providing advantageous properties such as usability in combination with a wide range of cosmetic ingredients.

In general formula (2), $R^2$ is a phenyl group or an alkyl group having from 1 to 6 carbons. Examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups.

In general formula (2), i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c. $L^{i+1}$ is preferably a methyl group when i=c.

From a technical standpoint, the number of generations c is preferably an integer from 1 to 3, and more preferably is 1 or 2. In each of the number of generations, the group represented by $L^1$ is expressed as follows. In this formula, $R^2$ and Z are synonymous with the groups described above.

When the number of generations c=1, $L^1$ is expressed by the following general formula (2-1).

General Formula (2-1):

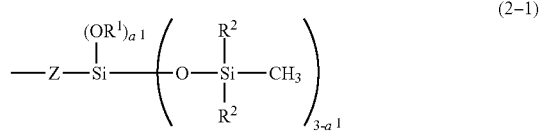

(2-1)

When the number of generations c=2, $L^1$ is expressed by the following general formula (2-2).

General Formula (2-2):

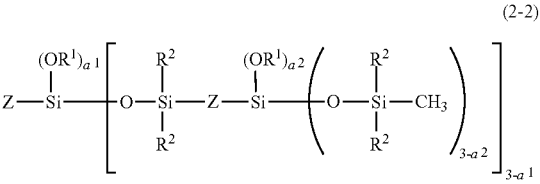

(2-2)

When the number of generations c=3, $L^1$ is expressed by the following general formula (2-3).

General Formula (2-3):

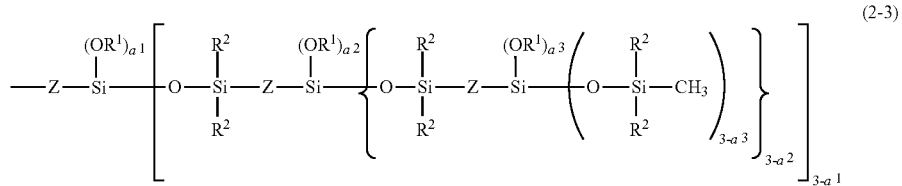

In formula (2), $a^i$ are each independently a number in a range from 0 to 3 and, in a structure expressed by formulae (2-1) to (2-3) where the number of generations is from 1 to 3, $a^1$, $a^2$, and $a^3$ are each independently a number in a range from 0 to 3. The $a^i$ is preferably a number in a range from 0 to 1 and more preferably the $a^i$ is 0.

In general formulae (2) and (2-1) to (2-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a carbosiloxane dendrimer structure, the functional group can be appropriately selected and is not restricted to the functional groups described above.

More specifically, Z are each independently a group selected from divalent organic groups expressed by the following general formulae (5-1) to (5-7). Of these, the Z in $L^1$ is preferably a divalent organic group expressed by general formula (5-1) that is introduced by a reaction between a silicon-bonded hydrogen atom and an alkenyl group. Likewise, Z is preferably a divalent organic group expressed by general formula (5-3) that is introduced by a reaction between a silicon-bonded hydrogen atom and an unsaturated carboxylic functional group. On the other hand, in the silylalkyl group represented by $L^i$ in which the number of generations c is 2 or more, and $L^i$ is $L^2$ to $L^c$, Z is preferably an alkylene group having from 2 to 10 carbons, more preferably a group selected from an ethylene group, a propylene group, a methylethylene group, and a hexylene group, and most preferably an ethylene group.

 (5-1)

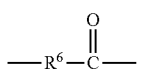 (5-2)

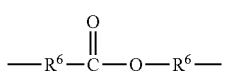 (5-3)

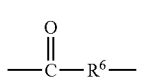 (5-4)

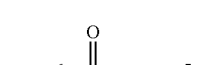 (5-5)

-continued

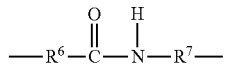 (5-6)

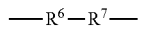 (5-7)

In these formulae (5-1) to (5-4), $R^6$ may have a substituent, and are each independently a straight or branched chain alkylene group or alkenylene group having from 2 to 22 carbons, or an arylene group having from 6 to 22 carbons. More specifically, examples of $R^6$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^6$ is preferably a group selected from an ethylene group, a propylene group, a methylethylene group, and a hexylene group.

In formulae (5-5) to (5-7), $R^7$ is a group selected from divalent organic groups expressed by the following formulae.

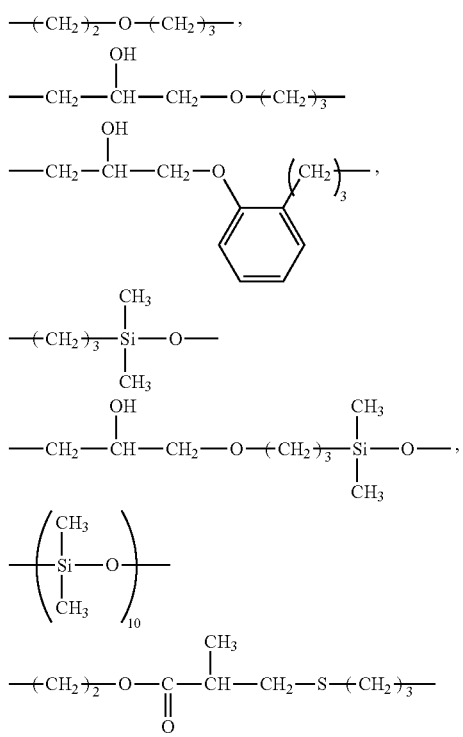

In general formula (1), Q is a hydrophilic segment, and is a portion that imparts the organopolysiloxane copolymer molecule according to the present application with hydrophilicity. Q is not particularly limited provided that it is a functional group derived from a hydrophilic compound, and examples thereof include alcohols that are at least monovalent, polyether-based compounds, polyglycerine-based compounds, polyglycidyl ether-based compounds, hydrophilic amines, hydrophilic sugars, and functional groups derived from quaternary amines or ammonium salts, that may be partially capped at the molecular end by a hydrocarbon.

More specifically, Q is a hydrophilic segment bonded to the silicon atom via a linking group that is at least divalent, and comprises at least one hydrophilic unit selected from hydrophilic units expressed by the following structural formulae (3-1) to (3-4).

$$-C_rH_{2r}-O- \quad (3\text{-}1)$$

The hydrophilic unit expressed by formula (3-1) is an oxyalkylene unit. In this formula, r is a number in a range from 1 to 6, and is preferably a number in a range from 2 to 4. The hydrophilic unit expressed by formula (3-1) can have one or more hydrophilic segments (Q). Additionally, the hydrophilic unit expressed by formula (3-1) is preferably included in the hydrophilic segment (Q) as a polyoxyalkylene unit where from 2 to 50 of the hydrophilic units expressed by formula (3-1) are linked and r are each independently from 2 to 4.

Particularly, from the standpoint of hydrophilicity, the hydrophilic unit expressed by formula (3-1) preferably is included in the hydrophilic segment Q as 4 to 50 linked polyoxyalkylene units, and more preferably as one or more type of the polyoxyalkylene unit expressed by formula (3-1-1).

$$-(C_2H_4O)_{t1}(C_3H_6O)_{t2}- \quad (3\text{-}1\text{-}1)$$

In this formula, t1 and t2 are each numbers greater than or equal to 0, and (t1+t2) is a number in a range from 4 to 50 and preferably in a range from 8 to 30.

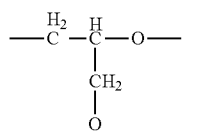
(3-2)

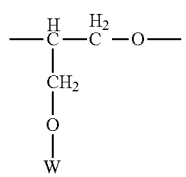
(3-3)

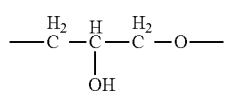
(3-4)

In formulae (3-2) to (3-4), W is a hydrogen atom or an alkyl group having from 1 to 20 carbons, and preferably is a hydrogen atom, a methyl group, or an ethyl group. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units expressed by structural formulae (3-2) to (3-4) are hydrophilic units included in a hydrophilic segment derived from a hydrophilic compound selected principally from polyhydric alcohols including glycerin, polyglycerines (also called "polyglycerols"), and polyglycidyl ethers or compounds in which terminal hydroxyl groups thereof are partially capped by hydrocarbon groups. However, the hydrophilic units are not limited thereto.

In general formula (1), Q may be, for example, a hydrophilic segment that does not have a branched structure such as a straight polyoxyalkylene group, and may also be a hydrophilic segment that has a branched structure in the segment such as a branched polyglycerol group or a branched polyglycidylether group.

More specifically, Q may be a hydrophilic segment bonded to the silicon atom via a linking group that is at least divalent, comprising at least one linearly bonded hydrophilic unit selected from hydrophilic units expressed by the following structural formulae (3-1) to (3-4); or, furthermore, Q may be a hydrophilic segment bonded to the silicon atom via a linking group that is at least divalent, comprising not less than one of at least one hydrophilic unit selected from hydrophilic units expressed by structural formulae (3-1) to (3-4) above, and a branch unit selected from groups expressed by structural formulae (3-5) to (3-7) below.

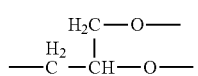
(3-5)

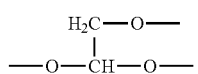
(3-6)

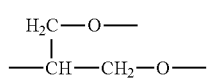
(3-7)

The linked group having at least divalency is a bonding site with respect to the siloxane included in the hydrophilic segment (Q), and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3 and more preferably 0 or 1 ether bonds in the linking group that is at least divalent.

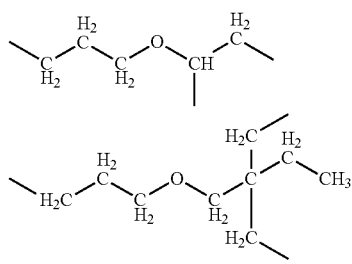

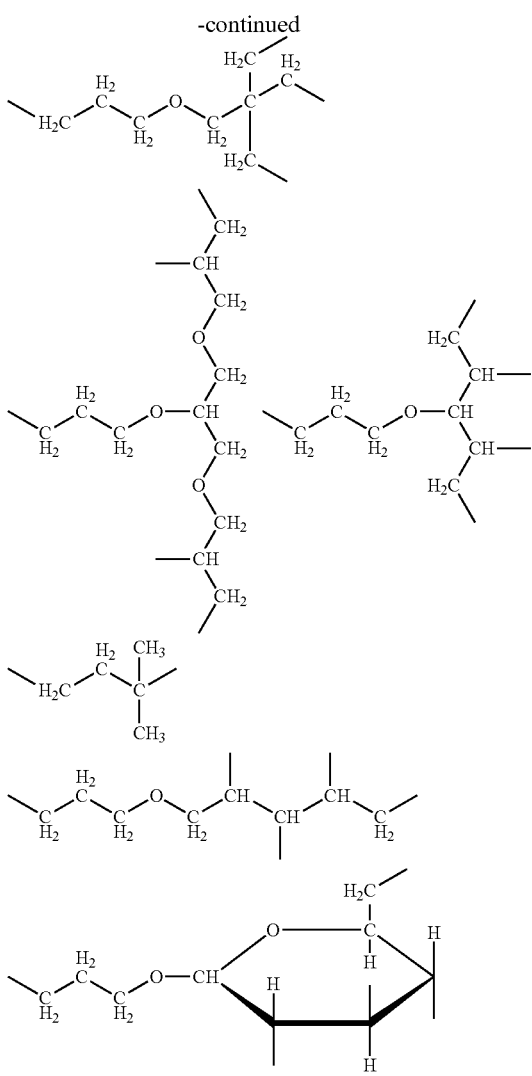

Q is more preferably a hydrophilic segment expressed by following general formulae (4-1) to (4-3).

General Formula (4-1):

$$—R^3(—O—X^1{}_m—R^4)_p \qquad (4\text{-}1)$$

In this formula, $R^3$ is an organic group having (p+1) valency, and p is a number that is greater than or equal to 1. Examples of $R^3$ include a group that is synonymous with the linking group having at least divalency.

It is more preferable that p is equal to 1 and that $R^3$ is a group selected from divalent organic groups expressed by the following general formula.

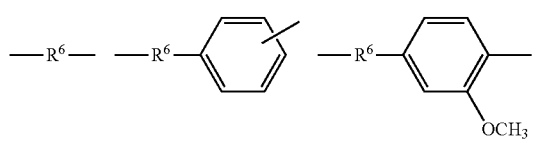

In this formula, $R^6$ may have a substituent, and are each independently a straight or branched chain alkylene group or alkenylene group having from 2 to 22 carbons, or an arylene group having from 6 to 22 carbons.

$X^1$ are each independently at least one hydrophilic unit selected from the hydrophilic units expressed by the general formulae (3-1) to (3-4) above, and m is a number in a range of 1 to 100. When $X^1$ is the hydrophilic unit (alkyleneoxy group) expressed by the general formula (3-1), m is preferably a number in a range from 4 to 50, and a structure expressed by $[—X^1{}_m—]$ is more preferably a polyoxyalkylene unit expressed by the formula (3-1-1). Additionally, when $X^1$ is the hydrophilic unit expressed by the general formulae (3-2) to (3-4), m is preferably a number in a range from 1 to 50, and more preferably is a number in a range from 1 to 15. $R^4$ is a hydrogen atom or a group selected from the group consisting of acyl groups, glycidyl groups, and alkyl groups having from 1 to 20 carbons, and preferably is a hydrogen atom or a methyl group.

General Formula (4-2):

$$—R^3(—O—X^2)_p \qquad (4\text{-}2)$$

In this formula, $R^3$ is a group synonymous with the groups described above, and p is a number synonymous with the number described above. $X^2$ is a hydrophilic unit expressed by structural formula (4-2-1) below.

In this formula, the at least one hydrophilic unit selected from hydrophilic units expressed by the general formulae (3-1) to (3-4) is bonded to two oxygen atoms, each independently. The hydrophilic unit may further be bonded to a branch unit selected from groups expressed by structural formulae (3-5) to (3-7). Moreover the hydrophilic unit may be formed so as to have a dendroid-shape polyether structure, a polyglycerol structure, or a polyglycidyl ether structure obtained by branching into multiple generations.

In cases when the hydrophilic unit does not have other branch units, examples of the hydrophilic segment expressed by general formula (4-2) include a hydrophilic segment expressed by the following general formula (4-2-2). In this formula, p, $R^3$, $X^1$, $R^4$, and m are the same as described above.

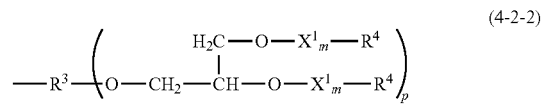

General Formula (4-3):

$$—R^3(—O—X^3)_p \qquad (4\text{-}3)$$

In this formula, $R^3$ is a group synonymous with the groups described above, and p is a number synonymous with the number described above. $X^3$ is a hydrophilic segment expressed by structural formula (4-3-1) below.

In this formula, the at least one hydrophilic unit selected from hydrophilic units expressed by the general formulae (3-1) to (3-4) is bonded to two oxygen atoms, each independently. The hydrophilic unit may further be bonded to a branch unit selected from groups expressed by structural formulae (3-5) to (3-7). Moreover the hydrophilic unit may be formed so as to have a dendroid-shape polyether structure, a polyglycerol structure, or a polyglycidyl ether structure obtained by branching into multiple generations.

In cases when the hydrophilic unit does not have other branch units, examples of the hydrophilic segment expressed by general formula (4-3) include a hydrophilic segment expressed by the following general formula (4-3-2). In this formula, p, $R^3$, $X^1$, $R^4$, and m are the same as described above.

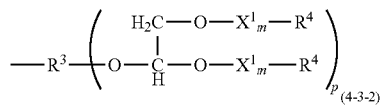

General Formula (4-4):

polyglycerol structure, or a polyglycidyl ether structure obtained by branching into multiple generations.

In cases when the hydrophilic unit does not have other branch units, examples of the hydrophilic segment expressed by general formula (4-4) include a hydrophilic segment expressed by the following general formula (4-4-2). In this formula, p, $R^3$, $X^1$, $R^4$, and m are the same as described above.

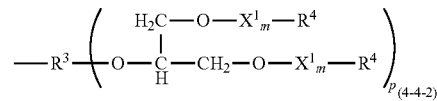

Particularly, the novel organopolysiloxane copolymer according to the present invention described above is preferably an AB-type organopolysiloxane copolymer expressed by the following structural formula. In this formula, Z, n, p, $R^3$, $X^1$, $R^4$ and m are the same as described above.

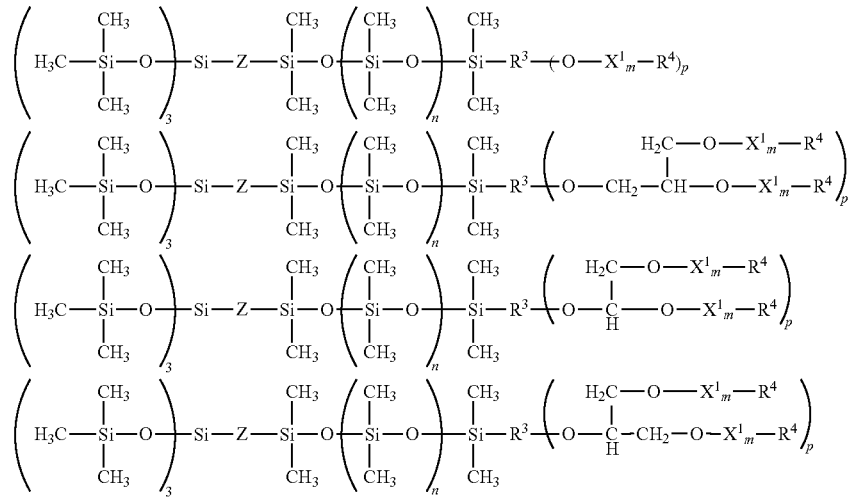

In this formula, $R^3$ is a group synonymous with the groups described above, and p is a number synonymous with the number described above. $X^4$ is a hydrophilic segment expressed by structural formula (4-4-1) below.

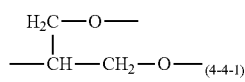

In this formula, the at least one hydrophilic unit selected from hydrophilic units expressed by the general formulae (3-1) to (3-4) is bonded to two oxygen atoms, each independently. The hydrophilic unit may further be bonded to a branch unit selected from groups expressed by structural formulae (3-5) to (3-7). Moreover the hydrophilic unit may be formed so as to have a dendroid-shape polyether structure, a Most preferably, the aforementioned Z is a straight or branched chain alkyl group having from 2 to 22 carbons, n is 0 or 1, and p is 1. This novel organopolysiloxane copolymer has superior compounding stability in cosmetics and feeling to touch improvement characteristics, can be used in combination with a wide range of cosmetic ingredients, and has superior surface activity and powder treating capability.

The novel organopolysiloxane copolymer according to the present application can be obtained by addition-reacting a hydrophilic compound, which has a reactive functional group at one terminal and a compound with a carbosiloxane dendron structure having one carbon-carbon double bond at another terminal of the molecular chain, with an organopolysiloxane capped at both molecular terminals with reactive functional groups. The type of addition reaction is not particularly limited but, from the standpoint of reaction control, purity, and yield, the addition reaction is preferably performed in the presence of a hydrosilylation reaction catalyst.

More specifically, an example of a method for manufacturing the novel organopolysiloxane copolymer comprises:

addition reacting (A) an organopolysiloxane having silicon-bonded hydrogen atoms at both molecular terminals expressed by general formula (1') below, and (B) a compound having a carbosiloxane dendron structure that has one carbon-carbon double bond at a molecular terminal expressed by general formula (2') below (at an amount less than or equal to ½ a molar equivalent of the component (A)) in the presence of (C) a hydrosilylation reaction catalyst; and, thereafter, further addition reacting (D) a hydrophilic compound having one alkenyl group at a molecular terminal (at an amount less than or equal to ½ a molar equivalent of the component (A)).

General Formula (1'):

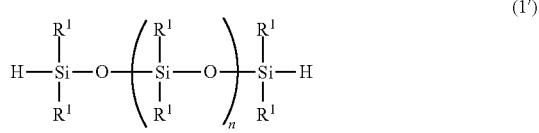

(1')

In general formula (1'), $R^1$ each independently represent an aryl group or an alkyl group having from 1 to 10 carbons, and n is a number in a range of 0 to 10.

General Formula (2'):

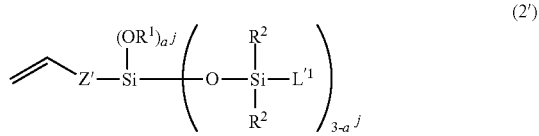

(2')

In general formula (2'), $L'^1$ is a methyl group or, when j=1, is a silylalkyl group expressed by general formula (2'') below, and Z' is a divalent organic group.

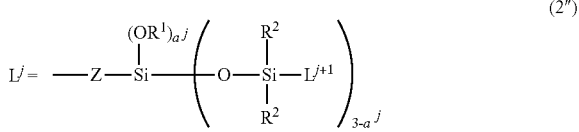

(2'')

In general formula (2), $R^2$ is a phenyl group or an alkyl group having from 1 to 6 carbons, and Z is a divalent organic group. j represents a generation of the silylalkyl group represented by $L^j$ and is an integer of 1 to c' when c' is a number of generations that is a number of repetitions of the silylalkyl group. The number of generations c' is an integer from 1 to 10, and $L^{j+1}$ is the silylalkyl group when j is less than c' and is a methyl group or a phenyl group when j=c'. $a^j$ is a number in a range of 0 to 3.

The hydrosilylation reaction is preferably performed in the presence of a catalyst. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum phosphine complex, platinum-phosphite complex, platinum alcholate catalyst, or the like. A usage amount of the catalyst is about 0.5 to 100 ppm in terms of platinum metal, when using a platinum catalyst.

The hydrophilic compound (D) having one alkenyl group on the molecular terminal is a hydrophilic compound having a reactive functional group such as an alkenyl group on a molecular terminal, and examples thereof include an allyl polyether, an allyl polyglycerol, an allyl polyglycidyl ether, a polyglyceryl eugenol, a glycerin monoallyl ether, and the like. The hydrophilic compound (D) can be synthesized according to a known method, or may be a commercially available product.

Additionally, the crude organopolysiloxane copolymer obtained via the addition reaction described above can be refined by performing a deodorizing treatment by a hydrogenation treatment in the presence of a hydrogenation catalyst in a solvent or without a solvent. This refined product can be preferably used in cases where the organopolysiloxane copolymer is used in an topical composition application in which odor reduction and compatibility with other cosmetic ingredients is needed. Moreover, the deodorizing treatment preferably has, as a pre-process or a post-process, a stripping process in which nitrogen gas is brought into contact with the crude organopolysiloxane copolymer or the hydrogenated product to remove light substance.

In the hydrogenation treatment and stripping process, solvents, reaction conditions, pressure-reduction conditions, and the like used in the refining of conventional organopolysiloxane copolymers can be used or selected without any restrictions.

Alternately, the odor of the crude organopolysiloxane copolymer obtained via the addition reaction described above can easily be reduced by performing a stripping process in which light substance is removed by bringing nitrogen gas into contact with the crude product, after an unreacted unsaturated compound is hydrolyzed by adding an acidic substance.

The novel organopolysiloxane copolymer according to the present invention is particularly useful as a surfactant or a powder treatment agent because it is hydrophobic, and has a carbosiloxane dendrimer structure that provides high water repellency and a hydrophilic segment in the same molecule. The hydrophilic segment is preferably a polyhydric alcohol such as polyether, glycerin, or the like, or a derivative thereof such as polyglycerine, polyglycidyl ether, or the like. Therefore, the novel organopolysiloxane copolymer of the present invention is particularly suited for use as a nonionic surfactant or a powder treatment agent for use in a cosmetic composition.

While applications as a surfactant are not particularly limited, the novel organopolysiloxane copolymer of the present invention displays superior surface activity effects (dispersibility, emulsifiability) at small amounts and, therefore has the benefits of being able to stably emulsify various oil agents and provide an emulsion with a unique texture and a superior feeling to touch. Moreover, the novel organopolysiloxane copolymer of the present invention is extremely useful as a surfactant for an topical composition, and, particularly, other than cosmetics, as a foam stabilizer used when manufacturing urethane foam, a release agent, an antifoam agent, a fiber treatment agent, an adhesive, an antifogging agent, a burnishing agent, a water repellent, a coating, a resin additive, an antistatic agent, and the like. Additionally, if a highly volatile polyether is used as the hydrophilic segment, the novel organopolysiloxane copolymer of the present invention can be suitably used in applications such as cleaning electronics or electronic parts.

The novel organopolysiloxane copolymer according to the present invention is, independently, a superior surfactant, but may also be suitably used in a mixture with a hydrophilic compound having a reactive functional group such as an alkenyl group or the like at a molecular terminal, such as an allyl polyether, an allyl polyglycerol, an allyl polyglycidyl ether, or the like. From the standpoint of uniform miscibility, emulsifiability, and dispersiblity with the organopolysiloxane copolymer, the hydrophilic compound having the reactive functional group is preferably exemplified by the same compound as the hydrophilic compound used in the manufacture of the organopolysiloxane copolymer.

The surfactant included in the organopolysiloxane copolymer according to the present invention can stably emulsify various oil agents and water to form an emulsion composition. The emulsion composition can be in the form of an oil-in-water emulsion or a water-in-oil emulsion. Furthermore, emulsion compositions comprising such an emulsion as an inner phase (particulate material), such as O/W/O type emulsions and the like can be obtained.

The emulsion composition preferably is an emulsion composition comprising (a) the organopolysiloxane copolymer according to the present invention, water, and an oil agent; and can be used as-is for a topical composition (particularly a cosmetic composition) or can be compounded as a raw material (particularly a cosmetic raw material) of various topical compositions.

The oil agent preferably is a (b) a silicone oil, a nonpolar organic compound, or a low polarity organic compound preferably used in a cosmetic raw material; and is preferably one or more oil agents selected from silicone oils, hydrocarbon oils, and ester oils that are liquid from 5 to 100° C. Note that, emulsification can be carried out by combining one or two or more commonly known vegetable oils and fats, animal oils and fats, higher alcohols, liquid triglyceride fatty acid, and artificial sebum with the oil agents described above. Note that this component (b) will be described in detail in the description related to the cosmetic composition of the present invention.

Water is free of ingredients that are harmful to the human body and needs only be clean. Examples thereof include tap water, purified water, mineral water, and the like. Additionally, a compounded amount of the water can be selected appropriately, but is generally within a range of 5 to 99 wt. % of the entire emulsion composition.

Examples of methods of dispersing/emulsifying the oil agent in water include using a mechanical force by means of an apparatus such as a homomixer, a paddle mixer, a Henschel mixer, a homodisper, a colloid mill, a propeller stirrer, a homogenizer, an in-line type continuous emulsifier, an ultrasonic emulsifier, a vacuum kneader, or the like to disperse the oil agent in water.

When using the novel organopolysiloxane copolymer as a powder treatment agent, dispersion stability in mixed oil agent systems is excellent and, after preparing a powder composition obtained by treating the powder surface using a treatment agent, even when a method is used where the powder composition is dispersed in an oil agent dispersing medium, a powder in oil dispersion having superior stability is provided in which the powder does not agglomerate or precipitate.

The powder that can be treated or dispersed by the novel organopolysiloxane copolymer of the present invention is preferably (d) a powder or colorant. Additionally, the component (d) is a powder and/or a colorant for use in a cosmetic composition, and this powder and/or colorant can be any powder provided that it is normally used in cosmetic compositions, and is not limited to form (sphere, bar, needle, plate, amorphous, spindle or the like), particle size (aerosol, microparticle, pigment-grade particle, or the like), or particle structure (porous, nonporous, or the like) thereof. When compounding the powder and/or colorant as a pigment, preferably one or two or more selected from an inorganic pigment powder, an organic pigment powder, and a resin powder having an average diameter in a range of 1 nm to 20 μm is compounded.

Examples of the powder or colorant (d) include inorganic powders, organic powders, surfactant metal salt powders (metallic soaps), colored pigments, pearl pigments, metal powder pigments, and the like. In addition, compound products of the pigments can also be used. Specific examples of inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, black mica, lithia mica, silicic acid, silicic acid anhydride, aluminum silicate, sodium silicate, magnesium sodium silicate, magnesium silicate, aluminum magnesium silicate, calcium silicate, barium silicate, strontium silicate, metal salts of tungstic acid, hydroxyapatite, vermiculite, higilite, bentonite, montmorillonite, hectorite, zeolite, ceramic powder, secondary Calcium phosphate, alumina, aluminum hydroxide, boron nitride, and the like. Examples of organic powders include polyamide powder, polyester powder, polyethylene powder, polypropylene powder, polystyrene powder, polyurethane powder, benzoguanamine powder, polymethylbenzoguanamine powder, polytetrafluoroethylene powder, poly(methyl methacrylate) powder, cellulose, silk powder, nylon powder, nylon 12, nylon 6, silicone powder, silicone rubber powder, silicone elastomer spherical particles surface-coated with polymethylsilsesquioxane, polymethylsilsesquioxane spherical particles, copolymers of styrene and acrylic acid, copolymers of divinylbenzene and styrene, vinyl resin, urea resin, phenol resin, fluorine resin, silicone resin, acrylic resin, melamine resin, epoxy resin, polycarbonate resin, microcrystalline fiber powder, starch powder, lauroyl lysine, and the like. Examples of surfactant metal salt powders include zinc stearate, aluminum stearate, calcium stearate, magnesium stearate, zinc myristate, magnesium myristate, zinc palmitate, zinc laurate, zinc cetylphosphate, calcium cetylphosphate, sodium zinc cetylphosphate, and the like. Examples of colored pigments include inorganic red pigments such as red iron oxide, iron oxide, iron hydroxide, iron titanate and the like; inorganic brown pigments such as gamma-iron oxide and the like; inorganic yellow pigments such as yellow iron oxide, ocher, and the like; inorganic black iron pigments such as black iron oxide, carbon black, and the like; inorganic purple pigments such as manganese violet, cobalt violet, and the like; inorganic green pigments such as chromium hydroxide, chromium oxide, cobalt oxide, cobalt titanate, and the like; inorganic blue pigments such as Prussian blue, ultramarine blue, and the like; laked pigments of tar pigments such as Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, Orange No. 207, and the like, laked pigments of natural pigments such as carminic acid, laccaic acid, carthamin, brazilin, crocin, and the like. Examples of pearl pigments include titanium oxide-coated mica, titanium mica, iron oxide-treated titanium mica, titanium oxide-coated mica, bismuth oxychloride, titanium oxide-coated bismuth oxychloride, titanium oxide-coated talc, fish scale foil, titanium oxide-coated colored mica, and the like. Examples of the metal powder pigment include powders of metals such as aluminum, gold, silver, copper, platinum, stainless steel, and the like.

Additionally, a UV-ray absorbing or scattering powder such as microparticle titanium oxide, microparticle iron-containing titanium oxide, microparticle zinc oxide, microparticle cerium oxide, compound products thereof, and the like may be used.

Furthermore, the powder and/or colorant is preferably partially or entirely subjected to a water-repellent treatment. Additionally, a product can be used in which these powders and/or colorants are compounded together; or subjected to surface treatment using a general oil agent, a silicone oil other than the organopolysiloxane copolymer according to the present invention, a fluorine compound, a surfactant, or the like. One type thereof or two or more types thereof can be used, as necessary. Furthermore, the compounded amount of the powder and/or colorant is preferably in a range from 0.1 to 99 wt. % of the entire cosmetic composition. Particularly, the compounded amount when using in a powdered solid cosmetic composition is preferably in a range from 80 to 99 wt. % of the entire cosmetic composition.

Examples of other water-repellent treatments include various treatments in which the powder and/or colorant is surface treated with a water repellency agent. Specific examples thereof include organosiloxane treatments such as a methylhydrogenpolysiloxane treatment, a silicone resin treatment, a silicone gum treatment, an acryl silicone treatment, a fluorinated silicone treatment, and the like; metallic soap treatments such as a zinc stearate treatment and the like; silane treatments such as a silane coupling agent treatment, an alkylsilane treatment, and the like; fluorine compound treatments such as a perfluoroalkylsilane treatment, a perfluoroalkyl phosphate treatment, a perfluoro polyether treatment, and the like; amino acid treatments such as an N-lauroyl-L-lysine treatment and the like; oil agent treatments such as a squalane treatment and the like; acryl treatments such as an alkyl acrylate treatment and the like. The treatments described above can be used in combinations of one or more types thereof.

When using the novel organopolysiloxane copolymer of the present invention as the powder surface treating agent, a compounded amount of the organopolysiloxane copolymer (a) and the powder and/or colorant (b) is preferably in a range from 0.1 to 30 parts by weight, and more preferably from 0.5 to 10 parts by weight per 100 parts by mass of the powder and/or colorant.

The organopolysiloxane copolymer according to the present invention can be used to treat a powder surface using a conventional method. This method is not particularly limited, and an appropriate method from those described below can be selected.

1. A method in which the target powder is surface treated by being dispersed in a medium selected from organic solvents in which a treatment agent is compounded.

2. A method in which the powder and a powder treatment agent are mixed and, thereafter, surface treating is performed using a pulverizer such as a ball mill, a jet mill, or the like.

3. A treatment method in which a treatment agent is compounded in a solvent and adsorbed on a surface of the powder by dispersing the powder therein and, thereafter, dried and sintered.

Additionally, "powder in oil dispersion" as used in the present invention, refers to a product in which a powder composition obtained as described above is dispersed in an oil agent or, alternately, a product in which an organopolysiloxane copolymer is dissolved or dispersed in an oil agent, and then the powder is added by being mixed or dispersed therein; and a form thereof is that of a liquid dispersed product. The powder in oil dispersion of the present invention can be appropriately prepared according to a known method such as the methods described below.

1. A method in which the powder composition obtained as described above is added to and dispersed in an oil agent such as an ester oil, a silicone oil, or the like.

2. A method in which an organopolysiloxane copolymer is dissolved or dispersed in the oil agent described above, the powder is added thereto, and the mixing is performed using a dispersing apparatus such as a ball mill, a bead mill, a sand mill, or the like.

The obtained powder in oil dispersion can be compounded as-is in a cosmetic composition.

In addition to being usable in surface activation, powder treatment, and powder dispersion as described above, the novel organopolysiloxane copolymer of the present invention can also be used in combination with a wide range of cosmetic ingredients. Thus, the novel organopolysiloxane copolymer of the present invention is extremely useful as a raw material in all types of preparations for external use that are topically applied to the skin or hair, specifically cosmetic raw materials or medicament raw materials.

Particularly, the novel organopolysiloxane copolymer of the present invention is suitable as a raw material of a cosmetic composition, can be used preferably as a water-based cosmetic raw material of the emulsion or the like, or can be used in a substantially water-free nonaqueous-based cosmetic composition. When used in these cosmetic composition applications, the compounded amount of the organopolysiloxane copolymer is preferably in a range of 0.1 to 40 wt. % of the entire cosmetic product.

The cosmetic composition of the present invention preferably comprises from 0.1 to 99.9 wt. % of (a) the organopolysiloxane copolymer according to the present invention and from 99.9 to 0.1 wt. % of (b) the silicone oil, the nonpolar organic compound, or the low polarity organic compound components.

The component (b) is what is referred to as the "oil agent" and preferable examples thereof include hydrophobic silicone oils that have a viscosity at 25° C. from 0.65 to 1000,000 mm²/s and nonpolar organic compounds or low polarity organic compounds that are a liquid at from 5 to 100° C.

Specific examples of the silicone oil component (b) include straight organopolysiloxanes expressed by the following general formula (6), cyclic organopolysiloxanes expressed by the general formula (7), and branched organopolysiloxanes expressed by the general formula (8).

General Formula (6):

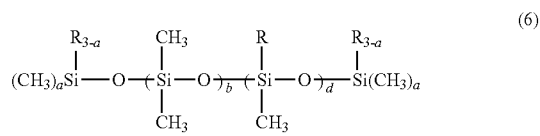

General Formula (7):

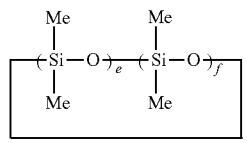

General Formula (8):

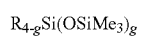

In general formulae (6) to (8) of the preceding paragraph, Me is a methyl group, R is a hydrogen atom, a hydroxyl group, or a group selected from an nonsubstituted or fluorine substituted monovalent alkyl group having from 2 to 30 carbons, an aryl group, an amino substituted alkyl group, an alkoxy group, and a group expressed by (CH3)3SiO{(CH3)2SiO}$_h$Si(CH3)2CH2CH2-. Specific examples thereof include saturated aliphatic hydrocarbon groups such as ethyl groups, propyl groups, butyl groups, pentyl groups, hexyl groups, heptyl groups, octyl groups, decyl groups, dodecyl groups, and the like; unsaturated aliphatic hydrocarbon groups such as vinyl groups, allyl groups, hexenyl groups, and the like; saturated cycloaliphatic hydrocarbon groups such as cyclopentyl groups, cyclohexyl groups, and the like; aromatic hydrocarbon groups such as phenyl groups, tolyl groups, naphthyl groups, and the like; and groups wherein the hydrogen atoms bonded to the carbon atoms of these groups are substituted partially by an organic group having a halogen atom, an epoxy group, a carboxyl group, an amino group, a (meth)acryl group, a mercapto group, or the like, or a group substituted by a trimethylsiloxy group and bonded via a divalent hydrocarbon group and/or a straight polydimethyl siloxane bond. a are each individually an integer from 0 to 3. b is an integer in a range from 0 to 1,000, d is an integer in a range from 0 to 1,000, and (b+d) is an integer in a range from 1 to 2,000. e and f are integers in a range from 0 to 8, and satisfy the relationship 3≤e+f≤8. Additionally, g is an integer in a range of 1 to 4, and h is an integer in a range of 0 to 500.

Examples of silicone oils having the structure described above include cyclic organopolysiloxanes such as hexamethyl cyclotrisiloxane (D3), octamethyl cyclotetrasiloxane (D4), decamethyl cyclopentasiloxane (D5), dodecamethylcyclohexasiloxane (D6), 1,1-diethylhexamethyl cyclotetrasiloxane, phenylheptamethyl cyclotetrasiloxane, 1,1-diphenylhexamethyl cyclotetrasiloxane, 1,3,5,7-tetravinyltetramethyl cyclotetrasiloxane, 1,3,5,7-tetramethyl cyclotetrasiloxane, 1,3,5,7-tetracyclohexyltetramethyl cyclotetrasiloxane, tris(3,3,3-trifluoropropyl)trimethylcyclotrisiloxane, 1,3,5,7-tetra(3-methacryloxypropyl)tetramethyl cyclotetrasiloxane, 1,3,5,7-tetra(3-acryloxypropyl)tetramethyl cyclotetrasiloxane, 1,3,5,7-tetra(3-carboxypropyl)tetramethyl cyclotetrasiloxane, 1,3,5,7-tetra(3-vinyloxypropyl)tetramethyl cyclotetrasiloxane, 1,3,5,7-tetra(p-vinylphenyl)tetramethyl cyclotetrasiloxane, 1,3,5,7-tetra[3-(p-vinylphenyl)propyl]tetramethyl cyclotetrasiloxane, 1,3,5,7-tetra(N-acryloyl-N-methyl-3-aminopropyl)tetramethyl cyclotetrasiloxane, 1,3,5,7-tetra(N,N-bis(lauroyl)-3-aminopropyl)tetramethyl cyclotetrasiloxane, and the like. Examples of straight organopolysiloxanes include a dimethylpolysiloxane in which both molecular terminals are capped with trimethylsiloxy groups (dimethylsilicone with a low viscosity such as 2 cst or 6 cst to dimethylsilicone with a high viscosity such as 1,000,000 cst), an organohydrogenpolysiloxane, a methylphenylpolysiloxane in which both molecular terminals are capped with trimethylsiloxy groups, a copolymer of methylphenylsiloxane and dimethylsiloxane in which both molecular terminals are capped with trimethylsiloxy groups, a diphenylpolysiloxane in which both molecular terminals are capped with trimethylsiloxy groups, a copolymer of diphenylsiloxane and dimethylsiloxane in which both molecular terminals are capped with trimethylsiloxy groups, a trimethylpentaphenyltrisiloxane, a phenyl (trimethylsiloxy)siloxane, a methylalkylpolysiloxane in which both molecular terminals are capped with trimethylsiloxy groups, a copolymer of methylalkylsiloxane and dimethylpolysiloxane in which both molecular terminals are capped with trimethylsiloxy groups, a copolymer of methyl (3,3,3-trifluoropropyl)siloxane and dimethylsiloxane in which both molecular terminals are capped with trimethylsiloxy groups, an α,ω-dihydroxypolydimethylsiloxane, an α,ω-diethoxypolydimethylsiloxane, a 1,1,1,3,5,5,5-heptamethyl-3-octyltrisiloxane, a 1,1,1,3,5,5,5-heptamethyl-3-dodecyltrisiloxane, a 1,1,1,3,5,5,5-heptamethyl-3-hexadecyltrisiloxane, a tristrimethylsiloxymethylsilane, a tristrimethylsiloxyalkylsilane, a tetrakistrimethylsiloxysilane, a tetramethyl-1,3-dihydroxydisiloxane, an octamethyl-1,7-dihydroxytetrasiloxane, a hexamethyl-1,5-diethoxytrisiloxane, a hexamethyldisiloxane, an octamethyltrisiloxane, a higher alkoxy-modified silicone, a higher fatty acid-modified silicone, and the like.

When at least one type of these silicone oils is included in the cosmetic composition of the present invention, the refreshing feeling to touch particular to silicone oil can be realized. For example, spreadability of the cosmetic composition on the skin and a refreshing feeling to touch can be imparted by including the silicone oil in a range from 0.5 to 25 wt. %, of the organosiloxane copolymer, in combination with a low viscosity organopolysiloxane. In this case, a compounded amount of the silicone oil is preferably in a range of 0.5 to 25 wt. % of the entire cosmetic composition.

Preferable oil agents other than silicone oils are oil agents that are liquid at 5 to 100° C. Preferably oil agents other than silicone oil are hydrocarbon oils and/or fatty ester oils. While these oil agents are components that are widely used, particularly as base materials for make-up cosmetic compositions, because they have a dendrimer structure, the oil agents have benefits of excellent compatibility with non-silicone based oil agents and the ability to maintain the moisturizing durability of these hydrocarbon oils and/or fatty ester oils. Furthermore, the organosiloxane copolymer according to the present invention functions as a surfactant or surfactant aid. Therefore, there are the benefits of improved compounding stability and stability over time of these oil agents in the cosmetic composition.

Compounding these oil agents other than silicone oil within a range of 0.5 to 25 wt. % of the entire cosmetic composition in forms of application where the oil agents are not used as the base material of the cosmetic composition such as in hair cosmetic compositions and oil-in-water emulsion cosmetics is beneficial in that the moisturizing durability and moisturizing feel of the cosmetic composition and a smooth sensation during use can be imparted. On the other hand, in a form of application in which the oil agents are used as the base material of a make-up cosmetic composition, a stable form of application and appearance of the cosmetic composition can be maintained and overall compatibility with other oil-based raw materials can be improved by compounding the oil agent in a range of 0.1 to 95 wt. % of the entire cosmetic composition.

Additionally, regarding the relationship of the oil agent with the components other than the component (a), by using the hydrocarbon oil and/or fatty ester oil in combination with the silicone oil, in addition to the refreshing feeling to touch particular to the silicone oil being imparted, moisture on the skin is retained, and a feeling that the cosmetic composition is moisturizing the skin or hair (also referred to as a "rich feeling to touch") and a smooth feeling to touch can be imparted. Moreover, stability over time of the cosmetic composition is not inhibited. Furthermore, with a cosmetic composition comprising the hydrocarbon oil and/or fatty ester oil and the silicone oil, these moisturizing components can be applied more stably and uniformly on the skin or hair, the moisturizing effects of the moisturizing component on the skin are improved and, compared to a cosmetic composition comprising only the oil agent other than the silicone oil (the hydrocarbon oil and/or fatty ester oil), a smoother, richer feeling to touch is imparted.

Examples of the hydrocarbon oil component (b) include liquid paraffin, light liquid isoparaffin, heavy liquid isoparaffin, vaseline, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene/polypropylene wax, squalane, squalene, pristane, polyisoprene, and the like.

Examples of the ester oil component (b) include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyloctanoate, cetyl lactate, myristyl lactate, diethyl phthalate, dibutyl phthalate, lanolin acetate, ethylene glycol monostearate, propylene glycol monostearate, propylene glycol dioleate, glyceryl monostearate, glyceryl monooleate, glyceryl tri(2-ethylhexanoate), trimethylolpropane tri(2-ethylhexanoate), ditrimethylolpropane triethylhexanoate, ditrimethylolpropane isostearate/sebacate, trimethylolpropane trioctanoate, trimethylolpropane triisostearate, diisopropyl adipate, diisobutyl adipate, 2-hexyldecyl adipate, di-2-heptylundecyl adipate, diisostearyl malate, hydrogenated castor oil monoisostearate, N-alkylglycol monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum ester, ethyl oleate, octyldodecyl oleate, neopentylglycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyloctyl sebacate, cetyl palmitate, octyldodecyl palmitate, octyl palmitate, 2-ethylhexyl palmitate, 2-hexyldecyl palmitate, 2-heptylundecyl palmitate, cholesteryl 12-hydroxystearate, dipentaerythritol fatty acid ester, 2-hexyldecyl myristate, ethyl laurate, 2-octyldodecyl N-lauroyl-L-glutamate, di(cholesteryl/behenyl/octyldodecyl)N-lauroyl-L-glutamate, di(cholesteryl/octyldodecyl)N-lauroyl-L-glutamate, di(phytosteryl/behenyl/octyldodecyl)N-lauroyl-L-glutamate, di(phytosteryl/octyldodecyl)N-lauroyl-L-glutamate, isopropyl N-lauroylsarcosinate, diisostearyl malate, neopentylglycol dioctanoate, isodecyl neopentanoate, isotridecyl neopentanoate, isostearyl neopentanoate, isononyl isononanoate, isotridecyl isononanoate, octyl isononanoate, isotridecyl isononanoate, diethylpentanediol dineopentanoate, methylpentanediol dineopentanoate, octyldodecyl neodecanoate, 2-butyl-2-ethyl-1,3-propanediol dioctanoate, pentaerythrityl tetraoctanoate, pentaerythrityl hydrogenated rosin, pentaerythrityl triethylhexanoate, dipentaerythrityl (hydroxystearate/stearate/rosinate), polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethylene glycol distearate), diisopropyl dimer dilinoleate, diisostearyl dimer dilinoleate, di(isostearyl/phytosteryl)dimer dilinoleate, (phytosteryl/behenyl)dimer dilinoleate, (phytosteryl/isostearyl/cetyl/stearyl/behenyl)dimer dilinoleate, dimer dilinoleyl dimer dilinoleate, dimer dilinoleyl diisostearate, dimer dilinoleyl hydrogenated rosin condensate, dimer dilinoleic acid hydrogenated castor oil, hydroxyalkyl dimer dilinoleyl ether, glyceryl triisooctanoate, glyceryl triisostearate, glyceryl trimyristate, glyceryl triisopalmitate, glyceryl trioctanoate, glyceryl trioleate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosane dioate, glyceryl di-2-heptylundecanoate, diglyceryl myristate isostearate, cholesteryl acetate, cholesteryl nonanoate, cholesteryl stearate, cholesteryl isostearate, cholesteryl oleate, cholesteryl 12-hydroxystearate, cholesteryl ester of macadamia nut oil fatty acid, phytosteryl ester of macadamia nut oil fatty acid, phytosteryl isostearate, cholesteryl ester of soft lanolin fatty acid, cholesteryl ester of hard lanolin fatty acid, cholesteryl ester of long-chain branched fatty acid, cholesteryl ester of long-chain α-hydroxy fatty acid, octyldodecyl ricinoleate, octyldodecyl ester of lanolin fatty acid, octyldodecyl erucate, isostearic acid hydrogenated castor oil, ethyl ester of avocado fatty acid, isopropyl ester of lanolin fatty acid, and the like.

Examples of fats or oils, higher alcohols, or higher fatty acids (the component (b)) include natural animal or vegetable fats and oils and semi-synthetic fats and oils such as avocado oil, linseed oil, almond oil, ibota wax, perilla oil, olive oil, cacao butter, kapok wax, kaya oil, carnauba wax, liver oil, candelilla wax, beef tallow, neatsfoot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shea butter, Chinese tung oil, cinnamon oil, jojoba wax, olive squalane, shellac wax, turtle oil, soybean oil, tea seed oil, camellia oil, evening primrose oil, corn oil, lard, rapeseed oil, Japanese tung oil, rice bran wax, germ oil, horse fat, persic oil, palm oil, palm kernel oil, castor oil, hydrogenated castor oil, castor oil fatty acid methyl ester, sunflower oil, grape oil, bayberry wax, jojoba oil, hydrogenated jojoba ester, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, reduced lanolin, lanolin alcohol, hard lanolin, lanolin acetate, lanolin fatty acid isopropyl ester, POE lanolin alcohol ether, POE lanolin alcohol acetate, lanolin fatty acid polyethylene glycol, POE hydrogenated lanolin alcohol ether, egg yolk oil, and the like. Herein, "POE" means "polyoxyethylene". Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, POE cholesteryl ether, monostearyl glycerol ether (batyl alcohol), monooleyl glycerol ether (selachyl alcohol), and the like. Examples of higher fatty acids include lauric acid, myristic acid, palmitic acid, stearic acid, behenic acid, undecylenic acid, oleic acid, linolic acid, linolenic acid, arachidonic acid, eicosapentaenoic acid (EPA), docosahexaenoic acid (DHA), isostearic acid, 12-hydroxystearic acid, and the like.

Examples of the fluorine-based oil component (b) include perfluoropolyether, perfluorodecalin, perfluorooctane, and the like, and one or two or more types of these oil agents can be used as necessary.

The topical composition and preferably the cosmetic composition of the present invention can, as necessary, further comprise another surfactant component (c). Particularly, one or two or more surfactants (c) selected from the group consisting of an anionic surfactant, a cationic surfactant, a nonionic surfactant, an amphoteric surfactant, and a semipolar surfactant can be used in combination for the purpose of dispersing the oil agent in water with higher stability. Furthermore, from the standpoint of being able to improve overall stability of the formulation, a silicone-based nonionic surfactant is preferably used. A compounded amount of these surfactants (c) is in a range from 0.1 to 25 wt. % and preferably in a range from 0.5 to 10 wt. % of the entire cosmetic composition. However, in cases where the cosmetic composition according to the present invention is a cosmetic composition for cleansing skin or cleansing hair, for the purpose of improving cleansing properties, the compounded amount can be adjusted to within a range from 0.1 to 90 wt. % of the entire cosmetic composition and, from the standpoint of cleansing ability, the surfactant component is preferably compounded at an amount not less than 25 wt. % of the entire cosmetic composition.

Likewise, in cases where the organopolysiloxane copolymer of the present invention is used in a cleansing agent, from the standpoint of cleansing activity, two or more types of surfactants can be preferably compounded.

More specifically, examples of anionic surfactants include saturated or unsaturated fatty acid salts (e.g. sodium laurate, sodium stearate, sodium oleate, sodium linolenate, and the like); alkylsulfuric acid salts; alkylbenzene sulfonic acids (e.g. hexylbenzenesulfonic acid, octylbenzenesulfonic acid, dodecylbenzenesulfonic acid, and the like) and salts thereof; polyoxyalkylene alkyl ether sulfuric acid salts; polyoxyalkylene alkenyl ether sulfuric acid salts; polyoxyethylene alkylsulfuric ester salts; sulfosuccinic acid alkyl ester salts; polyoxyalkylene sulfosuccinic acid alkyl ester salts; polyoxyalkylene alkylphenyl ether sulfuric acid salts; alkanesulfonic acid salts; octyltrimethylammonium hydroxide; dodecyltrimethylammonium hydroxide; alkyl sulfonates; polyoxyethylene alkylphenyl ether sulfuric acid salts; polyoxyalkylene alkyl ether acetic acid salts; alkyl phosphoric acid salts; polyoxyalkylene alkyl ether phosphoric acid salts; acylglutamic acid salts; α-acylsulfonic acid salts; alkylsulfonic acid salts; alkylallylsulfonic acid salts; α-olefinsulfonic acid salts; alkylnaphthalene sulfonic acid salts; alkanesulfonic acid salts; alkyl- or alkenylsulfuric acid salts; alkylamide sulfuric acid salts; alkyl- or alkenyl phosphoric acid salts; alkylamide phosphoric acid salts; alkyloylalkyl taurine salts; N-acylamino acid salts; sulfosuccinic acid salts; alkyl ether carboxylic acid salts; amide ether carboxylic acid salts; a-sulfofatty acid ester salts; alanine derivatives; glycine derivatives; and arginine derivatives. Examples of salts include alkali metal salts such as sodium salts and the like, alkaline earth metal salts such as magnesium salts and the like, alkanolamine salts such as triethanolamine salts and the like, and ammonium salts.

Examples of cationic surfactants include alkyltrimethylammonium chloride, stearyltrimethylammonium chloride, lauryltrimethylammonium chloride, cetyltrimethylammonium chloride, beef tallow alkyltrimethylammonium chloride, behenyltrimethylammonium chloride, stearyltrimethylammonium bromide, behenyltrimethylammonium bromide, distearyldimethylammonium chloride, dicocoyldimethylammonium chloride, dioctyldimethylammonium chloride, di(POE)oleylmethylammonium (2 EO) chloride, benzalkonium chloride, alkyl benzalkonium chloride, alkyl dimethylbenzalkonium chloride, benzethonium chloride, stearyl dimethylbenzylammonium chloride, lanolin derivative quaternary ammonium salt, diethylaminoethylamide stearate, dimethylaminopropylamide stearate, behenic acid amide propyldimethyl hydroxypropylammonium chloride, stearoyl colaminoformyl methylpyridinium chloride, cetylpyridinium chloride, tall oil alkylbenzyl hydroxyethylimidazolinium chloride, and benzylammonium salt.

Examples of nonionic surfactants include polyoxyalkylene ethers, polyoxyalkylene alkyl ethers, polyoxyalkylene fatty acid esters, polyoxyalkylene fatty acid diesters, polyoxyalkylene resin acid esters, polyoxyalkylene (hardened) castor oils, polyoxyalkylene alkyl phenols, polyoxyalkylene alkyl phenyl ethers, polyoxyalkylene phenyl phenyl ethers, polyoxyalkylene alkyl esters, polyoxyalkylene alkyl esters, sorbitan fatty acid esters, polyoxyalkylene sorbitan alkyl esters, polyoxyalkylene sorbitan fatty acid esters, polyoxyalkylene sorbitol fatty acid esters, polyoxyalkylene glycerol fatty acid esters, polyglycerol alkyl ethers, polyglycerol fatty acid esters, sucrose fatty acid esters, fatty acid alkanolamides, alkylglucosides, polyoxyalkylene fatty acid bisphenyl ethers, polypropylene glycol, diethyleneglycol, polyoxyalkylene-modified silicones, polyglyceryl-modified silicones, glyceryl-modified silicones, sugar-modified silicones, fluorine-based surfactants, polyoxyethylene/polyoxypropylene block polymers, and alkyl polyoxyethylene/polyoxypropylene block polymer ethers. Additionally, as necessary, polyoxyalkylene-modified silicones, polyglyceryl-modified silicones, and glyceryl-modified silicones in which an alkyl branch, a straight chain silicone branch, a siloxane dendrimer branch, or the like is provided with the hydrophilic group can be preferably used.

Examples of amphoteric surfactants include imidazoline-type, amidobetaine-type, alkylbetaine-type, alkylamidobetaine-type, alkylsulfobetaine-type, amidosulfobetaine-type, hydroxysulfobetaine-type, carbobetaine-type, phosphobetaine-type, aminocarboxylic acid-type, and amidoamino acid-type amphoteric surfactants. Specific examples thereof include imidazoline-type amphoteric surfactants such as sodium 2-undecyl-N,N,N-(hydroxyethylcarboxymethyl)-2-imidazoline, 2-cocoyl-2-imidazolinium hydroxide-1-carboxyethyloxy disodium salt, and the like; alkylbetaine-type amphoteric surfactants such as lauryl dimethylaminoacetic acid betaine, myristyl betaine, and the like; and amidobetaine-type amphoteric surfactants such as coconut oil fatty acid amidopropyl dimethylamino acetic acid betaine, palm kernel oil fatty acid amidopropyl dimethylamino acetic acid betaine, beef tallow fatty acid amidopropyl dimethylamino acetic acid betaine, hardened beef tallow fatty acid amidopropyl dimethylamino acetic acid betaine, lauric amidopropyl dimethylamino acetic acid betaine, myristic amidopropyl dimethylamino acetic acid betaine, palmitic amidopropyl dimethylamino acetic acid betaine, stearic amidopropyl dimethylamino acetic acid betaine, oleic amidopropyl dimethylamino acetic acid betaine, and the like; alkyl sulfobetaine-type amphoteric surfactants such as coconut oil fatty acid dimethyl sulfopropyl betaine and the like; alkylhydroxy sulfobetaine-type amphoteric surfactants such as lauryl dimethylaminohydroxy sulfobetaine and the like; phosphobetaine-type amphoteric surfactants such as laurylhydroxy phosphobetaine and the like; amidoamino acid-type amphoteric surfactants such as sodium N-lauroyl-N'-hydroxyethyl-N'-carboxymethyl ethylenediamine, sodium N-oleoyl-N'-hydroxyethyl-N'-carboxymethyl ethylenediamine, sodium N-cocoyl-N'-hydroxyethyl-N'-carboxymethyl ethylenediamine, potassium N-lauroyl-N'-hydroxyethyl-N'-carboxymethyl ethylenediamine, potassium N-oleoyl-N'-hydroxyethyl-N'-carboxymethyl ethylenediamine, sodium N-lauroyl-N-hydroxyethyl-N'-carboxymethyl ethylenediamine, sodium N-oleoyl-N-hydroxyethyl-N'-carboxymethyl ethylenediamine, sodium N-cocoyl-N-hydroxyethyl-N'-carboxymethyl ethylenediamine, monosodium N-lauroyl-N-hydroxyethyl-N',N'-dicarboxymethyl ethylenediamine, monosodium N-oleoyl-N-hydroxyethyl-N',N'-dicarboxymethyl ethylenediamine, monosodium N-cocoyl-N-hydroxyethyl-N',N'-dicarboxymethyl ethylenediamine, disodium N-lauroyl-N-hydroxyethyl-N',N'-dicarboxymethyl ethylenediamine, disodium N-oleoyl-N-hydroxyethyl-N',N'-dicarboxymethyl ethylenediamine, disodium N-cocoyl-N-hydroxyethyl-N',N'-dicarboxymethyl ethylenediamine, and the like.

Examples of semipolar surfactants include alkylamine oxide-type surfactants, alkylamine oxides, alkylamide amine oxides, alkylhydroxyamine oxides, and the like. Alkyldimethylamine oxides having from 10 to 18 carbons, alkoxyethyl dihydroxyethylamine oxides having from 8 to 18 carbons, and the like are preferably used. Specific examples thereof include dodecyldimethylamine oxide, dimethyloctylamine oxide, diethyldecylamine oxide, bis-(2-hydroxyethyl)dodecylamine oxide, dipropyltetradecylamine oxide, methylethylhexadecylamine oxide, dodecylamidopropyldimethylamine oxide, cetyldimethylamine oxide, stearyldimethylamine oxide, tallow dimethylamine oxide, dimethyl-2-hydroxyoctadecylamine oxide, lauryldimethylamine oxide, myristyldimethylamine oxide, stearyldimethylamine oxide, isostearyldimethylamine oxide, coconut fatty acid alkyldimethylamine oxide, caprylic amide propyldimethylamine oxide, capric amide propyldimethylamine oxide, lauric amide propyldimethylamine oxide, myristic amide propyldimethylamine oxide, palmitic amide propyldimethylamine oxide, stearic amide propyldimethylamine oxide, isostearic amide propyldimethylamine oxide, oleic amide propyldimethylamine oxide, ricinoleic amide propyldimethylamine oxide, 12-hydroxystearic amide propyldimethylamine oxide, coconut fatty acid amide propyldimethylamine oxide, palm kernel oil fatty acid amide propyldimethylamine oxide, castor oil fatty acid amide propyldimethylamine oxide, lauric amide ethyldimethylamine oxide, myristic amide ethyldimethylamine oxide, coconut fatty acid amide ethyldimethylamine oxide, lauric amide ethyldiethylamine oxide, myristic amide ethyldiethylamine oxide, coconut fatty acid amide ethyldiethylamine oxide, lauric amide ethyldihydroxyethylamine oxide, myristic amide ethyldihydroxyethylamine oxide, and coconut fatty acid amide ethyldihydroxyethylamine oxide.

The topical composition, particularly the cosmetic composition, of the present invention can, as necessary, further comprise a powder or colorant that is the same as the component (d).

The topical composition, particularly the cosmetic composition, of the present invention can, as necessary, further comprise a water-soluble polymer (e). The water-soluble polymer is compounded in order to enhance the sensation during use of the cosmetic composition. Any of amphoteric, cationic, anionic, and nonionic polymers, and water-swellable clay minerals can be used provided that it is commonly used in a cosmetic composition. One type or a combination of two or more types of water-soluble polymers can be used. The water-soluble polymers described above have an effect of thickening a hydrous component and, for this reason, are particularly useful in obtaining a gel-like water-based emulsion type cosmetic composition.

The water-soluble polymer can be compounded in order to prepare a cosmetic composition in the desired form, improve sensation during use of the cosmetic composition such as feeling to touch with respect to hair or the like, improving conditioning effects, and the like. Any of amphoteric, cationic, anionic, and nonionic polymers, and water-swellable clay minerals can be used provided that it is commonly used in a cosmetic composition. One type or a combination of two or more types of water-soluble polymers can be used. The water-soluble polymers described above have an effect of thickening a hydrous component and, for this reason, are particularly useful in obtaining a gel-like hydrous cosmetic composition, a water-in-oil emulsion cosmetic composition, and an oil-in-water emulsion cosmetic composition. Examples of natural water-soluble polymers include vegetable-based polymers such as gum Arabic, tragacanth gum, galactan, guar gum, carob gum, karaya gum, carrageenan, pectin, agar, quince seed (*Cyclonia oblonga*), algal colloid (seaweed extract), starch (rice, corn, potato, or wheat), glycyrrhizinic acid, and the like; microorganism-based polymers such as xanthan gum, dextran, succinoglucan, pullulan, and the like; and animal-based polymers such as collagen, casein, albumin, gelatin, and the like. Additionally, examples of semisynthetic water-soluble polymers include starch-based polymers such as carboxymethyl starch, methylhydroxypropyl starch, and the like; cellulose-based polymers such as methylcellulose, nitrocellulose, ethylcellulose, methylhydroxypropylcellulose, hydroxyethylcellulose, sodium cellulose sulfate, hydroxypropylcellulose, sodium carboxymethylcellulose (CMC), crystalline cellulose, cellulose powder, and the like; and alginate-based polymers such as sodium alginate, propylene glycol alginate, and the like. Examples of synthetic water-soluble polymers include vinyl-based polymers such as polyvinylalcohol, polyvinyl methyl ether-based polymer, polyvinylpyrrolidone, and carboxyvinyl polymer (CARBOPOL 940, CARBOPOL 941; manufactured by BF Goodrich Corporation), and the like; polyoxyethylene-based polymers such as polyethyleneglycol 20,000, polyethyleneglycol 6,000, polyethyleneglycol 4,000, and the like; copolymer-based polymers such as a copolymer of polyoxyethylene and polyoxypropylene, PEG/PPG-methylether, and the like; acryl-based polymers such as poly(sodium acrylate), poly(ethyl acrylate), polyacrylamide, and the like; polyethylene imines; cationic polymers; and the like. Examples of other cationic water-soluble polymers, in particular, as components which are preferably compounded in hair cosmetic compositions, include quaternary nitrogen-modified polysaccharides (e.g. cation-modified cellulose, cation-modified hydroxyethylcellulose, cation-modified guar gum, cation-modified locust bean gum, cation-modified starch, and the like); dimethyldiallylammonium chloride derivatives (e.g. a copolymer of dimethyldiallylammonium chloride and acrylamide, poly(dimethylmethylene piperidinium chloride), and the like); and vinylpyrrolidone derivatives (e.g. a copolymer of vinylpyrrolidone and dimethylaminoethyl methacrylic acid, a copolymer of vinylpyrrolidone and methacrylamide propyltrimethylammonium chloride, a copolymer of vinylpyrrolidone and methylvinylimidazolium chloride, and the like).

The topical composition, particularly a cosmetic composition, of the present invention can, depending on the purpose thereof, further comprise a silicone resin (f).

Preferable examples of silicone resins used in the cosmetic composition of the present invention depending on the purpose of the cosmetic composition include solid silicone netlike compounds such as MQ resins, MDQ resin, MTQ resin, MDTQ resin, TD resin, TQ resin, and TDQ resin formed from any combination of a trialkylsiloxy unit (M unit), a dialkylsiloxy unit (D unit), a monoalkylsiloxy unit (T unit), and a tetrafunctional siloxy unit (Q unit). Note that the sub stituent on the silicon of these silicone resins may include a substituted alkyl group, a phenyl group, an aryl group, or the like, in addition to the alkyl group. Of these, from the standpoint of obtaining superior usability, fluorine-modified silicone resins, trimethylsiloxy silicic acid (MQ resin), and dimethylsiloxy group-containing trimethylsiloxy silicic acid (MDQ resin) are particularly preferable. Compounding the silicone resin (D) in conjunction with the organopolysiloxane copolymer (A) according to the present invention is useful because the following improvement effects can be obtained due to the compounding of the silicone resin (D): improvements in feeling to touch of the cosmetic composition, uniform adhesion to the applied area, and adhesion of the powder to the skin.

The topical composition, particularly a cosmetic composition, of the present invention can, depending on the purpose thereof, further comprise a silicone elastomer (g).

The silicone elastomer (g) can be compounded in the cosmetic composition in any form, depending on the purpose of the cosmetic composition, but is preferably compounded as an organopolysiloxane elastomers spherical powder or a crosslinking organopolysiloxane.

Adding a powder silicone elastomer to a cosmetic composition comprising the organopolysiloxane copolymer (A) according to the present invention is advantageous because a feeling to touch that is substantial, such as that obtained when an oil agent is dispersed, is imparted, unevennesses of the skin are concealed, and, in contrast with oil agents, a natural impression is given due to oily shininess of the skin and oily texture being suppressed.

A primary particle size of silicone elastomer spherical particles (the component (g)) is preferably in a range from 0.1 to 50 μm. The organopolysiloxane elastomer spherical powder may be surface treated using silicone resin, silica, or the like. Examples of commercially available products of the organopolysiloxane elastomer spherical powder include Trefil E-506S, Trefil E-508, 9701 Cosmetic Powder, and 9702 Powder, manufactured by Dow Corning Toray Co., Ltd., and the likeAdditionally, the organopolysiloxane elastomer spherical powder can be used in the cosmetic composition of the present invention in the form of an aqueous dispersion. Examples of commercially available products of the aqueous dispersion include BY 29-129 and PF-2001 PIF Emulsion, manufactured by Dow Corning Toray Co., Ltd., and the like.

The crosslinking organopolysiloxane (the component (g)) is an organopolysiloxane having a structure in which the organopolysiloxane chain is three-dimensionally crosslinked via a reaction with a crosslinking component or the like, and preferably does not have a hydrophilic portion such as a polyoxyalkylene unit or the like, and is non-emulsifiable. Any crosslinking organopolysiloxane can be used without limitations to physical modes or preparation methods such as dilution, properties, and the like, provided that it is a crosslinking organopolysiloxane. Particularly preferable examples include α,ω-diene crosslinking silicone elastomers (commercially available products include DC 9040 Silicone Elastomer Blend, DC 9041 Silicone Elastomer Blend, DC 9045 Silicone Elastomer Blend, and DC 9046 Silicone Elastomer Blend, manufactured by Dow Corning Corporation, in the USA) described in U.S. Pat. No. 5,654,362. Likewise, examples of partially crosslinking organopolysiloxane polymers include (dimethicone/vinyldimethicone) crosspolymers, (dimethicone/phenylvinyldimethicone) crosspolymers, (PEG-8 to 30/C6 to C30 alkyldimethicone) crosspolymers, (vinyldimethicone/C6 to C30 alkyldimethicone) crosspolymers, (dimethicone/polyglycerol) crosspolymers, and the like, using INCI names (International Nomenclature Cosmetic Ingredient labeling names)

In the case of being compounded as an emulsifiable crosslinking organopolysiloxane formed by crosslinking by means of a polyether compound as a component in a cosmetic composition, the organopolysiloxane copolymer (A) according to the present invention functions as a surfactant or, alternately, a surfactant aid. For this reason, there is an advantage in that a uniform emulsification system can be formed. Furthermore, because the crosslinking organopolysiloxane functions as a surfactant, even when used in small amounts, a hydrous gel structure can be formed stably. This is advantageous because a water-containing cosmetic composition or emulsion cosmetic composition can be obtained that is soft and has superior water retention properties.

On the other hand, in the case of being compounded as a non-emulsifiable crosslinking organopolysiloxane, formed by crosslinking by means of an unsaturated hydrocarbon group such as a diene or an organopolysiloxane as a component, in a cosmetic composition, feel of adhesion to the skin can be improved. Furthermore, there are advantages in that excellent compatibility with other oil agents can be obtained, and the entire oil system can be uniformly and stably compounded in the cosmetic composition.

One or two or more types of the silicone elastomer can be compounded depending on the purpose thereof. A compounded amount of the silicone elastomer is preferably in a range from 0.05 to 25 wt. % and more preferably in a range from 0.1 to 15 wt. % of the entire cosmetic composition, depending on purpose and compounding intention.

Depending on the purpose thereof, the cosmetic composition of the present invention can include one or two or more ultraviolet light blocking components as a component (h). Examples thereof include benzoic acid-based UV absorbers such as paraminobenzoic acid (hereinafter, referred to as "PABA"), PABA monoglycerol ester, N,N-dipropoxy-PABA ethyl ester, N,N-diethoxy-PABA ethyl ester, N,N-dimethyl-PABA ethyl ester, N,N-dimethyl-PABA butyl ester, 2-[4-(diethylamino)-2-hydroxybenzoyl]benzoic acid hexylester (trade designation: Uvinul A plus), and the like; anthranilic acid-based UV absorbers such as homomethyl-N-acetylanthranilate and the like; salicylic acid-based UV absorbers such as amyl salicylate, menthyl salicylate, homomethyl salicylate, octyl salicylate, phenyl salicylate, benzyl salicylate, p-isopropanolphenyl salicylate, and the like; cinnamic acid-based UV absorbers such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxy cinnamate, ethyl-α-cyano-β-phenylcinnamate, 2-ethylhexyl-α-cyano-β-phenylcinnamate, glyceryl mono-2-ethylhexanoyl-diparamethoxycinnamate, 3-methyl-4-[methylbis(trimethylsiloxy)silylbutyl 3,4,5-trimethoxycinnamate, dimethicodiethyl benzal malonate (trade designation: PARSOL® SLX (INCI: Polysilicone-15)), and the like; benzophenone-based UV absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone- 5-sulfonate, 4-phenylbenzophenone, 2-ethylhexyl-4'-phenylbenzophenone-2-carboxylate, hydroxy-4-n-octoxybenzophenone, 4-hydroxy-3-carboxybenzophenone, and the like; benzotriazole-based UV absorbers such as 3-(4'-methylbenzylidene)-d,l-camphor, 3-benzylidene-d,l-camphor, urocanic acid, urocanic acid ethylester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dibenzaladine, dianisoylmethane, 4-methoxy-4'-t-butylbenzoylmethane, 5-(3,3-dimethyl-2-norbonylidene)-3-pentan-2-one, 2,2'-methylene bis(6-(2H-benzotriazole-2-il)-4-(1,1,3,3-tetramethylbutyl)phenol), and the like; triazine-based UV absorbers such as 2,4,6-tris[4-(2-ethylhexyloxycarbonyl)anilino]1,3,5-triazine, 2,4-bis-6-(4-methoxyphenyl)-1,3,5-triazine, and the like; 2-cyano-3,3-diphenyl prop-2-enoic acid-2-ethylhexyl ester; and the like.

Additionally, it is possible to use a product in which the organo-ultraviolet light blocking component is comprised in a hydrophobic polymer powder. The polymer powder may be hollow, and preferably has an average primary particle size in a range from 0.1 to 50 μm. Particle size distribution may be broad or sharp. Examples of types of the polymer include acrylic resins, methacryl resins, styrene resins, polyurethane resins, polyethylene, polypropylene, polyethylene terephthalate, silicone resins, nylons, acrylamide resins, and silylated polypeptide resins. A polymer powder comprising from 0.1 to 30 wt. % of an organo-ultraviolet light blocking component is preferable, and a polymer powder comprising 4-tert-butyl-4'-methoxydibenzoylmethane, a UV-A absorber, is particularly preferable.

The ultraviolet light blocking component that can be preferably used in the cosmetic composition of the present invention is at least one selected from the group consisting of fine particulate titanium oxide, microparticulate zinc oxide, paramethoxy cinnamic acid-2-ethylhexyl, 4-tert-butyl-4'-methoxydibenzoylmethane, benzotriazole-based UV absorbers, and triazine-based UV absorbers. These ultraviolet light blocking components are generally used, are easy to acquire, and have high ultraviolet light blocking effects and, thus can be beneficially used. Particularly, it is preferable that a combination of an inorganic-based and an organo-ultraviolet light blocking component be used, and it is even more preferable that a combination of an ultraviolet light blocking component corresponding to UV-A and an ultraviolet light blocking component corresponding to UV-B be used.

By using the organosiloxane copolymer (A) and the ultraviolet light blocking component in combination in the cosmetic composition of the present invention, the ultraviolet light blocking component is stably dispersed in the cosmetic composition while the emulsion stability thereof is maintained and, thus superior ultraviolet light blocking capacity is imparted to the cosmetic composition. Particularly, in the cosmetic composition of the present invention, a compounded amount of the ultraviolet light blocking component with respect to the entire cosmetic composition is in a range from 0.1 to 40.0 wt. %, and more preferably in a range from 0.5 to 15.0 wt. %.

Depending on the purpose thereof, the cosmetic composition of the present invention can include an inorganic ultraviolet light blocking component in addition to the ultraviolet light blocking component described above. The inorganic ultraviolet light blocking component may be a component in which an inorganic powder or the like recited for the powder or colorant is compounded. Examples thereof include metal oxides such as titanium oxide, zinc oxide, cerium oxide, titanium suboxide, iron-doped titanium oxides, and the like; metal hydroxides such as iron hydroxides and the like; metal flakes such as platy iron oxide, aluminum flake, and the like; and ceramics such as silicon carbide, and the like. Of these, at least one type of a material selected from fine particulate metal oxides and fine particulate metal hydroxides with an average particle size in a range from 1 to 100 nm is preferable.

The powder is preferably subjected to, for example, a conventional surface treatment such as fluorine compound treatments, of which a perfluoroalkyl phosphate treatment, a perfluoroalkylsilane treatment, a perfluoropolyether treatment, a fluorosilicone treatment, or a fluorinated silicone resin treatment is preferable; silicone treatments, of which a methylhydrogenpolysiloxane treatment, a dimethylpolysiloxane treatment, or a vapor-phase tetramethyltetrahydrogen cyclotetrasiloxane treatment is preferable; silicone resin treatments, of which a trimethylsiloxysilicic acid treatment is preferable; pendant treatments which are methods of adding alkyl chains after a vapor-phase silicone treatment; silane coupling agent treatments; titanium coupling agent treatments; silane treatments, of which an alkylsilane treatment or an alkylsilazane treatment is preferable; oil agent treatments; N-acylated lysine treatments; polyacrylic acid treatments; metallic soap treatments in which a stearic acid salt or a myristic acid salt is preferably used; acrylic resin treatments; metal oxide treatments; and the like. Multiple treatments described above are preferably performed. For example, the surface of the fine particulate titanium oxide can be coated with a metal oxide such as silicon oxide, alumina, or the like and, thereafter, surface treating using an alkylsilane can be carried out. A total amount of material used for the surface treatment is preferably in a range from 0.1 to 50 wt. % of the weight of the powder.

The following other components generally used in cosmetic compositions may be added to the cosmetic composition of the present invention, provided that such components do not inhibit the effectiveness of the present invention: alcohols, water-soluble polymers, organic resins, oil-soluble gelling agents, organically modified clay minerals, anti-perspiration active components, deodorant agents, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like. Note that, the other components are not limited to the examples recited above. The cosmetic composition of the present invention can include at least one selected from the group consisting of an acryl silicone dendrimer copolymer, a silicone raw rubber, a polyamide-modified silicone, an alkyl-modified silicone wax, and an alkyl-modified silicone resin wax as a component.

The cosmetic composition of the present invention can include one or two or more polyhydric alcohols and/or lower monohydric alcohols as the alcohol. Examples of lower alcohols include ethanol, isopropanol, n-propanol, t-butanol, s-butanol, and the like. Examples of polyhydric alcohols include divalent alcohols such as 1,3-butylene glycol, 1,2-butylene glycol, propylene glycol, trimethylene glycol, tetramethylene glycol, 2,3-butylene glycol, pentamethylene glycol, 2-buten-1,4-diol, dibutylene glycol, pentyl glycol, hexylene glycol, octylene glycol, and the like; trivalent alcohols such as glycerol, trimethylol propane, 1,2,6-hexanetriol, and the like; polyhydric alcohols having 4 or more valences such as pentaerythritol, xylitol, and the like; and sugar alcohols such as sorbitol, mannitol, maltitol, maltotriose, sucrose, erythritol, glucose, fructose, a starch-decomposed product, maltose, xylitose, starch-decomposed sugar-reduced alcohol, and the like. Furthermore, examples other than low-molecule polyhydric alcohols include polyhydric alcohol polymers such as diethylene glycol, dipropylene glycol, triethylene glycol, polypropylene glycol, tetraethylene glycol, diglycerol, polyethylene glycol, triglycerol, tetraglycerol, polyglycerol, and the like. Of these, 1,3-butylene glycol, sorbitol, dipropylene glycol, glycerol, and polyethylene glycol are particularly preferable. A compounded amount thereof is preferably from 0.1 to 50 wt. % of the entire cosmetic composition. Polyhydric alcohol can be blended in order to improve storage stability of the cosmetic composition, in an amount ranging from about 5 to 30 wt. % of the entire cosmetic composition. This is an example of a preferable mode of the present invention.

Depending on the purpose of the cosmetic composition, an acryl silicone dendrimer copolymer can be used in the cosmetic composition of the present invention. Specific, preferable examples of acryl silicone dendrimer copolymers include a vinyl-based polymer having a carbosiloxane dendrimer structure at the side chain such as that described in Japanese Patent No. 4009382 (Japanese Unexamined Patent Application Publication No. 2000-063225). Examples of commercially available products thereof include FA4001 CM Silicone Acrylate, FA4002 ID Silicone Acrylate (manufactured by Dow Corning Toray Co., Ltd.), and the like. When compounding the acryl silicone dendrimer copolymer alone, superior film formability can be obtained. Therefore, by compounding the dendrimer copolymer in the cosmetic composition according to the present invention, a strong cosmetic coating film can be formed on the applied part, and cosmetic durability such as sebum resistance, rubbing resistance, and the like can be significantly improved.

By using the organosiloxane copolymer (a) together with the acryl silicone dendrimer copolymer, there are advantages in that a surface protective property such as sebum resistance can be improved due to strong water repellency provided by the carbosiloxane dendrimer structure; and at the same time, excellent feeling to touch and brightness are imparted when applying, and irregularities such as pores and wrinkles of the skin to which the cosmetic composition is applied can be effectively concealed due to the high emulsion stability of the present invention product being maintained. Moreover, the organosiloxane copolymer (a) according to the present invention displays excellent miscibility with other oil agents, powders, the colorants, and the acryl silicone dendrimer copolymer and, therefore, there is an advantage in that makeup running or gathering on the skin can be controlled. Furthermore, when powders or colorants are treated in accordance with a conventional method by using the organosiloxane copolymer (a) together with the acryl silicone dendrimer copolymer, a powder composition for use in a cosmetic composition with superior compounding stability can be prepared.

A compounded amount of the acryl silicone dendrimer copolymer can be suitably selected based on the purpose and compounding intent thereof, but is preferably in a range from 1 to 99 wt. % and more preferably in a range from 30 to 70 wt. % of the entire cosmetic composition.

The cosmetic composition of the present invention, depending on the purpose thereof, can include a silicone raw rubber (referred to also as "silicone gum"). Silicone raw rubber is differentiated from the oily silicones described above because the degree of polymerization of silicone raw rubber is high and, as a result, has a degree of plasticity that is measurable. Examples of such a silicone raw rubber include substituted or nonsubstituted organopolysiloxanes having a dialkylsiloxy unit (D unit). Examples thereof include dimethylpolysiloxane, methylphenylpolysiloxane, aminopolysiloxane, methylfluoroalkylpolysiloxane, and the like, products that have a micro crosslinked structure thereof, and the like. Of these, a dimethylpolysiloxane raw rubber having a degree of polymerization from 3,000 to 20,000 is preferable.

Silicone gum has an ultra-high degree of polymerization and, therefore forms a protective film with superior breathability and retention on hair or skin. Therefore, the silicone gum is a component which can particularly provide glossiness and luster to hair and can impart a texture of firmness and body to the entire hair during use and after use.

A compounded amount of the silicone gum is from 0.05 to 30 wt. % and preferably from 1 to 15 wt. % of the entire cosmetic composition. When an emulsion composition prepared via a step of pre-emulsifying (including emulsion polymerization) is used, the silicone gum can easily be compounded, and can be stably compounded in the various cosmetic compositions of the present invention. Particularly, when the cosmetic composition of the present invention is a hair cosmetic composition or the like, an effect of imparting a specific feeling to touch or glossiness of the hair may be insufficient if the compounded amount of the silicone gum is less than the lower limit described above.

Depending on the purpose of the cosmetic composition, a polyamide-modified silicone can be compounded in the cosmetic composition of the present invention. Examples of the polyamide-modified silicone include a siloxane-based polyamide described in U.S. Pat. No. 5,981,680; and examples of commercially available products include 2-8178 Gellant, 2-8179 Gellant, and the like (manufactured by Dow Corning Corporation, in the USA). Such polyamide-modified silicones are useful as an oil-based raw material, and in particular, a thickening/gelling agent of a silicone oil, similar to the oil-soluble gelling agent described above.

Compatibility with the oil agent such as a silicone oil or the like can be further improved by using the polyamide-modified silicone together with the organosiloxane copolymer of the present invention. Thereby, the cosmetic composition according to the present invention delivers a superior sense of stability and adhesion, and excellent spreading and setting when applied to the skin or hair. Additionally, there are advantages from a quality standpoint such that a glossy, sheer sensation and superior luster can be provided, the viscosity or hardness (softness) of the entire cosmetic composition containing the oil-based raw material can be appropriately adjusted, and an oily sensation (oily and sticky feeling to touch) can be totally controlled. Moreover, because polyamide-modified silicone and the organosiloxane copolymer is used, dispersion stability of a perfume, a powder, and the like can be improved. Thereby, the obtained cosmetic composition is characterized by being able to maintain a uniform and fine cosmetic sensation for an extended period of time.

A compounded amount of the polyamide-modified silicone can be suitably selected based on the purpose and compounding intent thereof but, when using the polyamide-modified silicone as a gelling agent for an oil-based raw material, is in a range from 0.5 to 80 parts by weight and preferably in a range from 1 to 50 parts by weight per 100 parts by weight of the oil-based component such as the oil agent or the like.

Depending on the purpose of the cosmetic composition, the cosmetic composition of the present invention can include an alkyl-modified silicone wax. The alkyl-modified silicone wax need only be an alkyl-modified silicone wax in wax form at room temperature, and examples thereof include methyl (long chain alkyl) polysiloxanes having both molecular terminals capped with trimethylsiloxy groups, copolymers of a dimethylpolysiloxane having both molecular terminals capped with trimethylsiloxy groups and a methyl (long chain alkyl) siloxane, dimethylpolysiloxane modified with long chain alkyls at both terminals, and the like. Examples of commercially available products include AMS-C30 Cosmetic Wax, 2503 Cosmetic Wax, and the like (manufactured by Dow Corning Corporation, in the USA).

When using the organosiloxane copolymer according to the present invention in combination with the alkyl-modified silicone wax, compatibility with the oil-based raw material is improved, and superior formability and uniform dispersibility of the other components can be obtained and, thereby a cosmetic composition exhibiting superior storage stability over an extended period of time can be obtained. In particular, in a system containing a powder and a colorant, there is an advantage in that separation of the system including the alkyl-modified silicone wax, for the most part, does not occur, and an oil-based cosmetic composition having superior form-retaining strength and which spreads smoothly and uniformly when applied can be provided.

In the present invention, the alkyl-modified silicone wax preferably has a melting point of not lower than 60° C. because such will lead to cosmetic retainability effects and stability at high temperatures. A compounded amount thereof can be suitably selected based on the purpose and compounding intent thereof, and can be compounded in a range from 1 to 50 wt. % of the entire cosmetic composition. The compounded amount is preferably in a range from 5 to 40 wt. % because such leads to improvements in the formability and cosmetic retainability of the oil-based cosmetic composition. Additionally, the alkyl-modified silicone wax displays high compatibility with silicone oil having a long chain alkyl group such as the alkyl-modified silicone or the like and the crosslinking organopolysiloxanes and, therefore, is preferably used in combination with these optional components.

Examples of the alkyl-modified silicone resin wax used in the cosmetic composition of the present invention depending on the purpose of the cosmetic composition include the silsesquioxane resin wax described in Japanese Patent Application (Translation of PCT Application) No. 2007-532754.

As a result of using the alkyl-modified silicone resin wax in combination with the organosiloxane copolymer of the present invention and compounding these in the cosmetic composition of the present invention, there are advantages of conditioning effects on skin and hair being improved and fine texture and a moisturized feeling to touch being imparted.

In the present invention, a compounded amount of the alkyl-modified silicone resin wax can be suitably selected based on the purpose and compounding intent thereof, and can be compounded in a range from 0.5 to 50 wt. % of the entire cosmetic composition. The compounded amount is preferably in a range from 1 to 30 wt. % in order to attain sebum durability and a fine texture feeling to touch of the cosmetic composition.

Examples of the organic resin used in the cosmetic composition of the present invention depending on the purpose of the cosmetic composition include polyvinylalcohol, polyvinylpyrrolidone, polyalkyl acrylate copolymers, and the like.

Examples of the oil-soluble gelling agent used in the cosmetic composition of the present invention depending on the purpose of the cosmetic composition include aluminum stearate, magnesium stearate, zinc myristate, and similar metal soaps; N-lauroyl-L-glutamic acid, α,γ-di-n-butylamine, and similar amino acid derivatives; dextrin palmitate, dextrin stearate, dextrin 2-ethylhexanoate palmitate, and similar dextrin fatty acid esters; sucrose palmitate, sucrose stearate, and similar sucrose fatty acid esters; monobenzylidene sorbitol, dibenzylidene sorbitol, and similar benzylidene derivatives of sorbitol; and the like.

Examples of the organo-modified clay mineral used depending on the purpose of the cosmetic composition include dimethylbenzyl dodecylammonium montmorillonite clay, dimethyldioctadecylammonium montmorillonite clay, dimethylalkylammonium hectorite, benzyldimethylstearylammonium hectorite, distearyldimethylammonium chloride-treated aluminum magnesium silicate, and the like. Examples of commercially available products include Benton 27 (benzyldimethylstearylammonium chloride-treated hectorite, manufactured by Nationalred Co.), Benton 38 (distearyldimethylammonium chloride-treated hectorite, manufactured by Nationalred Co.), and the like.

Depending on the purpose of the cosmetic composition, the cosmetic composition of the present invention can include an anti-perspiration active component. Examples of the anti-perspiration active component include astringent salts such as aluminum chlorohydrate, aluminum-zirconium tetrachlorohydrex glycine (ZAG), and the like; but aluminum, hafnium, zinc, and zirconium salts (e.g. aluminum halide, aluminum hydroxy halide, zirconium halide, zirconium oxyhalide, zirconium hydroxy halide, zirconyl hydroxide halide, aluminium chloride zirconium, zirconium lactate-aluminum, and basic aluminum halide) can be used. Examples thereof include $Al_2(OH)_5Cl$, aluminum bromide, buffer aluminium sulphate, alum, dried alum, various aqueous, alcohol, or glycine complexes thereof (e.g. a complex of an aluminum-zirconium chlorohydrate and glycine comprising aluminum, zirconium, and glycine (a ZAG complex), and the like. A single anti-perspiration active component may be used or a combination of two or more may be used. In cases where the anti-perspirant composition according to the present invention is a water-in-oil emulsion-type anti-perspirant composition, these anti-perspiration active components are an aqueous phase component. On the other hand, soybean extracts and isoflavones are known for their anti-perspirant effects; and, because they have low water solubility, are preferably used by dissolving them in the oil phase.

In the present invention, a compounded amount of the anti-perspiration active component is an amount sufficient to reduce perspiration, and restricting the compounded amount to a small amount can be beneficial in personal care compositions. Specifically, from the standpoints of anti-perspirant effects and feeling to touch, the compounded amount of the anti-perspiration active component in an anti-perspirant composition is preferably from 5 to 25 wt. % of the entire cosmetic composition. When using a water soluble anti-perspiration active component, from the standpoint of cost effectiveness, it is preferable to increase the proportion of water in the composition to a maximum limit, while maintaining anti-perspirant effects, but the anti-perspiration active component can also be added to the aqueous phase at amount near the saturation amount.

The cosmetic composition of the present invention, particularly the anti-perspirant composition, can include a deodorant agent in conjunction with or in place of the anti-perspirant component. Examples of the deodorant agent include deodorizers, perfumes, and substances that prevent or remove odors caused by perspiration. Such deodorant agents are antimicrobial agents (germicides or fungicides), bacteriostatic agents, odor absorbing substances, deodorizers, perfumes, or the like, and are compounded for the purpose of preventing underarm odor, odor from perspiration, foot odor, and other bodily odors. Note that these deodorant agents are useful in cosmetic compositions other than anti-perspirants and it goes without saying that they can be beneficially compounded in the cosmetic composition of the present invention.

Examples of antimicrobial agents include alkyltrimethylammonium bromide, cetylpyridinium chloride, benzethonium chloride, benzalkonium chloride, chlorhexidine hydrochloride, chlorhexidine gluconate, [[(diisobutylphenoxy)ethoxy]ethyl]dimethylbenzylammonium chloride, N-lauroyl sarcosine sodium, N-palmitoyl sarcosine sodium, N-myristoyl glycine, N-lauroyl sarcosine potassium, trimethyl ammonium chloride, aluminum chlorohydroxy sodium lactate, triethyl citrate, tricetyl methyl ammonium chloride, 1,5-pentanediol, 1,6-hexanediol, 2,4,4'-trichloro-2'-hydroxy diphenylether (triclosan), and 3,4,4'-trichlorocarbanilide(triclocarban); L-lysine hexadecylamide and similar diaminoalkylamidos; citric acid, salicylic acid, piroctose, and other heavy metal salts, preferably zinc salts and acids thereof; pyrithione heavy metal salts, preferably pyrithione zinc, phenol zinc sulfate, ethylparaben, butylparaben, hinokitiol, farnesol, phenoxyethanol, isopropyl methylphenol, propolis, lysozyme, lysozyme chloride, combinations of lysozyme and vitamin E or derivatives thereof, combinations of organic acids such as lysozyme and α-hydroxyacid, and the like; and the like.

Examples of bacteriostatic agents include 1-heptyl glyceryl ether, 1-(2-ethylhexyl)glyceryl ether, 1-octyl glyceryl ether, 1-decyl glyceryl ether, 1-dodecyl glyceryl ether, and similar glyceryl monoalkyl ethers.

The odor absorbing substance is not particularly limited, provided that it absorbs odor causing substances and reduces odor, is constituted by a portion of the inorganic powders and organic polymers described above, and displays the same characteristics.

Examples of the odor absorbing substance include zinc oxide, magnesium oxide, zeolite, aluminometasilicate, silicic anhydride, colloidal silica, talc, mica, hydroxyapatite, cellulose, corn starch, silk, nylon powder, crosslinking organopolysiloxane powder, organopolysiloxane elastomer spherical powder, and the like. Likewise, carbonates such as alkali metal carbonates, alkali metal bicarbonate salts, and the like and hydrogen carbonates, ammonium salts, tetraalkylammonium salts, and the like can be used. Of these odor absorbing substances, sodium salts and potassium salts are more preferable. Additionally, organic or inorganic porous particles carrying silver, copper, zinc, cerium, or similar metal ions (e.g. silver ion-carrying zeolite, silver ion/zinc ion/ammonium ion-carrying zeolite), or aggregates of needle-like crystals including silver cancrinite can be used. Because these function as antimicrobial agents and odor absorbing substances, they can be used beneficially as the deodorant agent.

Furthermore, hydroxyalkylated cyclodextrin, sake cake extract containing rice fermenting liquid, and various extracts derived from animals, vegetables, microorganisms, fungi, and the like such as brown seaweed extract, cinnamon bark, clove, fennel, ginger, mentha, citron, gentiana lutea, apricot, eucalyptus, Sophora flavescens, mulberry, althea, sage, Anthemis nobilis, Scutellaria root, nutgall, gardenia, hamamelis, herbs, and the like can be used as the deodorant agent. A part of these components overlaps with a bioactive component described below, but selecting these extracts as the deodorant agent for the purpose of the functional effects thereof is both beneficial and preferable from the standpoint of the composition design of the cosmetic composition.

Preferably from 0.001 to 60 wt. %, more preferably from 0.01 to 30 wt. %, and yet more preferably from 0.01 to 3 wt. % of the odor absorbing substance is included in the entire composition. Provided that the compounded amount of the odor absorbing substance is within this range, there is an advantage that deodorizing performance can be improved while not negatively affecting the strength and feeling to touch of the formulation.

An anti-perspirant composition according to the present invention can be selected from any of a water-in-oil emulsion (water-based formulation), a stick form formulation, and a spray or similar aerosol formulation. Components thereof are dependent on the type of formulation selected, and can be appropriately selected from the cosmetic ingredients described above.

The cosmetic composition of the present invention can include a preservative for the purpose of preventing decomposition and the like. Exemplary preservatives include alkyl paraoxybenzoates, benzoic acid, sodium benzoate, sorbic acid, potassium sorbate, phenoxyethanol, and the like. Examples of antimicrobial agents include benzoic acid, salicylic acid, carbolic acid, sorbic acid, alkyl paraoxybenzoates, parachloromethacresol, hexachlorophene, benzalkonium chloride, chlorhexidine chloride, trichlorocarbanilide, trichlosan, photosensitizers, and the like. However, in cases where the cosmetic composition is a rouge, it is preferable that these are not included.

Examples of bioactive components used in the cosmetic composition depending on the purpose of the cosmetic composition include substances that impart some sort of bioactivity to the skin when applied on the skin. Examples thereof include anti-inflammatory agents, anti-aging agents, ultraviolet light blocking agents, tightening agents, anti-oxidizing agents, hair regrowth agents, hair growth promoters, moisturizing agents, circulation promoters, antimicrobial agents, germicides, drying agents, cooling agents, warming agents, vitamins, amino acids, wound healing accelerators, irritation mitigation agents, analgesics, cell activating agents, enzyme components, and the like. Of these, natural vegetable extract components, seaweed extract components, and herbal medicine components are particularly preferable. In the present invention, a single bioactive component may be used or, preferably, two or more bioactive components are used.

Specific examples of the bioactive component include Angelica keiskei extract, avocado extract, Hydrangea serrata extract, Althaea officinalis extract, Arnica montana extract, aloe extract, apricot extract, apricot kernel extract, Gingko biloba extract, fennel fruit extract, turmeric root extract, oolong tea extract, Rosa multiflora extract, Echinacea angustifolia leaf extract, Scutellaria baicalensis root extract, Phellodendron amurense bark extract, Coptis rhizome extract, Hordeum vulgare seed extract, Hypericum perforatum extract, Lamium album extract, Nasturtium officinale extract, orange extract, dried sea water solution, seaweed extract, hydrolyzed elastin, hydrolyzed wheat powders, hydrolyzed silk, Chamomilla recutita extract, carrot extract, Artemisia capillaris flower extract, Glycyrrhiza glabra extract, Hibiscus sabdariffa extract, Pyracantha fortuneana extract, kiwi extract, Cinchona succirubra extract, cucumber extract, guanosine, Gardenia florida extract, Sasa veitchii extract, Sophora angusti folia extract, walnut extract, grapefruit extract, Clematis vitalba leaf extract, chlorella extract, Morus alba extract, Gentiana lutea extract, black tea extract, yeast extract, burdock extract, fermented rice bran extract, rice germ oil, Symphytum officinale leaf extract, collagen, Vaccinum vitis idaea extract, Asiasarum sieboldi extract, Bupleurum falcatum extract, umbilical extract, Salvia extract, Crocus sativus flower extract, sasa bamboo grass extract, Crataegus cuneata fruit extract, Zanthoxylum piperitum extract, Corthellus shiitake extract, Rehmannia chinensis root extract, Lithospermum erythrorhizone root extract, Perilla ocymoides extract, Tilia cordata extract, Spiraea ulmaria extract, Paeonia albiflora extract, Acorns calamus root extract, Betula alba extract, Equisetum arvense extract, Hedera helix extract, Crataegus oxyacantha extract, Sambucus nigra extract, Achillea millefolium extract, Mentha piperita leaf extract, sage extract, Malva sylvestris extract, Cnidium officinale root extract, Swertia japonica extract, soybean seed extract, Zizyphus jujuba fruit extract, thyme extract, Camellia sinensis leaf extract, Eugenia caryophyllus flower extract, Imperata cylindrica extract, Citrus unshiu peel extract, Angelica acutiloba root extract, Calendula officinalis extract, Prunus persica kernel extract, Citrus aurantium peel extract, Houttuynia cordata extract, tomato extract, natto extract, carrot extract, garlic extract, Rosa canina fruit extract, hibiscus extract, Ophiopogon japonicus root extract, Nelumbo nucifera extract, parsley extract, honey, Hamamelis virginiana extract, Parietaria officinalis extract, Isodon trichocarpus extract, bisabolol, Eriojotrya japonica extract, Tussilago farfara flower extract, Petasites japonicus extract, Poria cocos extract, Ruscus aculeatus root extract, grape extract, propolis, Luffa cylindrica fruit extract, safflower flower extract, peppermint extract, Tillia miquellana extract, Paeonia suffruticosa root extract, Humulus lupulus extract, Pinus sylvestris cone extract, horse chestnut extract, Lysichiton camtschatcense extract, Sapindus mukurossi peel extract, Melissa officinalis leaf extract, peach extract, Centaurea cyanus flower extract, Eucalyptus globulus leaf extract, Saxifraga sarementosa extract, Citrus junos extract, Coix lacryma-jobi seed extract, Artemisia princeps extract, lavender extract, apple extract, lettuce extract, lemon extract, Astragalus sinicus extract, rose extract, rosemary extract, Roman chamomile extract, royal jelly extract, and the like.

Additionally, examples of the bioactive component include biological macromolecules such as deoxyribonucleic acid, mucopolysaccharides, sodium hyaluronate, sodium chondroitin sulfate, collagen, elastin, chitin, chitosan, hydrolytic membrana testae, and the like; amino acids such as glycine, valine, leucine, isoleucine, serine, threonine, phenylalanine, arginine, lysine, aspartic acid, glutamic acid, cystine, cysteine, methionine, tryptophan, and the like; hormones such as estradiol, ethenyl estradiol, and the like; oil-based components such as sphingo lipid, ceramide, cholesterol derivatives, phosphatides, and the like; anti-inflammatory agents such as ε-aminocaproic acid, glycyrrhizinic acid, β-glycyrrhetic acid, lysozyme chloride, guai-azulene, hydrocortisone, allantoin, tranexamic acid, azulene, and the like; vitamins such as vitamin A, B2, B6, C, D, and E, calcium pantothenate, biotin, nicotinic acid amide, vitamin C esters, and the like; active components such as allantoin, diisopropyl amine dichloroacetate, 4-aminomethyl cyclohexanecarboxylic acid, and the like; anti-oxidizing agents such as carotenoid, flavonoid, tannin, lignan, saponin, and the like; cell activator agents such as α-hydroxyacid, β-hydroxyacid, and the like; circulation promoters such as γ-oryzanol, vitamin E derivatives, and the like; wound healing agents such as retinol, retinol derivatives, and the like; refreshing agents such as cepharanthine, licorice extract, capsicum tincture, hinokitiol, iodized garlic extract, pyridoxine hydrochloride, dl-α-tocopherol, dl-α-tocopherol acetate, nicotinic acid, nicotinic acid derivatives, calcium pantothenate, D-pantothenyl alcohol, acetyl pantothenyl ethyl ether, allantoin, isopropyl methylphenol, carpronium chloride, benzalkonium chloride, diphenhydramine hydrochloride, Takanal, camphor, vanillylamide nonylate, vanillylamide nonanoate, piroctone olamine, glyceryl pentadecanoate, l-menthol, camphor, and the like; hair growth promoters such as mononitroguaiacol, resorcin, γ-aminobutyric acid, benzethonium chloride, mexiletine hydrochloride, auxin, female hormones, Cantharides tincture, cyclosporin, zinc pyrithione, hydrocortisone, Minoxidil, polyoxyethylene sorbitan monostearate, mentha oil, Sasanishiki extract, and the like; and the like.

Moreover, examples of skin beautifying components include whitening agents such as placenta extracts, arbutin, glutathione, saxifrageous extracts, and the like; cell activating agents such as royal jelly and the like; agents for ameliorating skin roughness; circulation promoters such as nonylic acid vanillylamide, benzyl nicotinate, beta-butoxyethyl nicotinate, capsaicin, zingerone, cantharide tincture, ichthammol, caffeine, tannic acid, α-borneol, tocopherol nicotinate, inositol hexanicotinate, cyclandelate, cinnarizine, tolazoline, acetylcholine, verapamil, cepharanthine, γ-oryzanol, and the like; astringents such as zinc oxide, tannic acid, and the like; antiseborrheic agents such as sulfur, thianthol, and the like; and the like. Examples of vitamins include vitamin As such as vitamin A oil, retinol, retinol acetate, retinol palmitate, and the like; vitamin Bs such as vitamin B2s such as riboflavin, riboflavin butyrate, flavin adenine dinucleotide, and the like; vitamin B6s such as pyridoxine hydrochloride, pyridoxine dioctanoate, pyridoxine tripalmitate, and the like; vitamin B12 and derivatives thereof; vitamin B15 and derivatives thereof, and the like; vitamin Cs such as L-ascorbic acid, L-ascorbyl dipalmitic acid esters, sodium L-ascorbyl 2-sulfate, dipotassium L-ascorbyl phosphoric acid diester, and the like; vitamin Ds such as ergocalciferol, cholecalciferol, and the like; vitamin Es such as α-tocopherol, β-tocopherol, γ-tocopherol, dl-α-tocopherol acetate, dl-α-tocopherol nicotinate, dl-α-tocopherol succinate, and the like; vitamin H; vitamin P; nicotinic acids such as nicotinic acid, benzyl nicotinate, and the like; pantothenic acids such as calcium pantothenate, D-pantothenyl alcohol, pantothenyl ethyl ether, acetyl pantothenyl ethyl ether, and the like; and the like.

Examples of pH adjusting agents used in the cosmetic composition of the present invention depending on the purpose of the cosmetic composition include lactic acid, citric acid, glycolic acid, succinic acid, tartaric acid, dl-malic acid, potassium carbonate, sodium hydrogen carbonate, ammonium hydrogen carbonate, and the like.

Examples of the solvent compounded in the cosmetic composition of the present invention depending on the purpose of the cosmetic composition include light isoparaffin, ethers, LPG, N-methylpyrrolidone, next-generation chlorofluorocarbons, and the like, in addition to water such as purified water, mineral water, and the like.

Examples of the antioxidants compounded in the cosmetic composition of the present invention depending on the purpose of the cosmetic composition include tocopherol, butylhydroxyanisole, dibutylhydroxytoluene, phytic acid, and the like. Examples of the chelating agent include alanine, sodium salt of edetic acid, sodium polyphosphate, sodium metaphosphate, phosphoric acid, and the like.

Examples of other moisturizing components compounded in the cosmetic composition of the present invention depending on the purpose of the cosmetic composition include hyaluronic acid, chondroitin sulfate, pyrrolidone carboxylic acid salts, polyoxyethylene methylglucoside, polyoxypropylene methylglucoside, and the like. It goes without saying that the polyhydric alcohols and the like exhibit a function of retaining moisture on the skin or hair. With the cosmetic composition of the present invention, there are cases in which moisture retention properties of the moisturizing agent can be improved by using these moisturizing components in combination with other oil-based raw materials, selecting a gel-like formulation form for the cosmetic composition, or using the moisturizing components in combination with a membrane forming component.

Specific examples of products that the cosmetic composition of the present invention can be used for include skin cleansing agent products, skin care products, makeup products, anti-perspirant products, ultraviolet light blocking products, and similar skincare cosmetic products; hair cleansing agent products, hair dressing products, hair coloration products, hair growth products, hair rinsing products, hair conditioning products, hair treatment products, and similar hair cosmetic products; and bath use cosmetic products. The cosmetic composition of the present invention is preferably a skin care product, a cosmetic product for hair, an anti-perspirant product, a makeup product, or an ultraviolet light blocking product. Examples of the medicament of the present invention include hair regrowth agents, hair growth promoters, analgesics, germicides, anti-inflammatory agents, refreshing agents, and skin anti-aging agents, but are not limited thereto.

The skincare cosmetic products can be used on any site of the entire body including the scalp, face (including lips, eyebrows, and cheeks), fingers, and fingernails. Specific examples thereof include cleansing gels, cleansing creams, cleansing foams, cleansing milks, cleansing lotions, face washing creams, eye makeup removers, face washing foams, liquid soaps (body soaps), hand soaps, gel-like soaps, bar soaps, facial rinses, body rinses, shaving creams, removers, acne treatment cosmetics, and similar skin cleansing agent products; skin creams, scalp treatments, skin milks, milk lotions, emulsions, toners, moisturizing liquids, beautifying liquids, facial packs, body powders, essences, shaving lotions, massage lotions, and similar skin care products; foundations, liquid foundations, oil-based foundations, makeup bases, powders, face powders, lipsticks, lip creams, muddy colored lipsticks or rouges, lip glosses, eye shadows, eye liners, eye creams, eyebrow pencils, eyelash cosmetic products, eyebrow pencils, eyebrow blushes, mascaras, blushers, cheek cosmetics (cheek color, cheek rouge), manicures, pedicures, nail colors, nail laquers, enamel removers, nail polishes, and similar makeup products; deodorants and similar anti-perspirants; and sunscreen agents, tanning use medicaments (sun tanning agent), and similar ultraviolet light blocking products.

Examples of hair-care cosmetic products include shampoos, rinse-in shampoos, and similar hair cleansing agents; hair oils, hair waxes, hair curl holding agents, setting agents, hair creams, hairsprays, hair liquids, and similar hair dressing products; hair coloring substances, hair color sprays, hair color rinses, hair color sticks, and similar hair coloration products; hair tonics, hair treatment essences, hair packs, and similar hair growing products; and oil rinses, cream rinses, treatment rinses, hair conditioners, hair treatments, and similar hair rinse or hair conditioning products. Additionally, examples of the bath use cosmetic products include bath oils, bath salts, and bath foams.

The cosmetic composition according to the present invention is not particularly limited to a cosmetic product form, and can be preferably applied to liquid, W/O emulsion O/W emulsion, W/O cream, O/W cream, solid (e.g. stick and the like), paste, gel, powder, multi-layer, mousse, mist, granule, flake, crushed stone, and similar forms. Particularly preferable forms thereof are W/O emulsion, W/O cream, solid, paste, gel, powder, multi-layered, mousse, and spray forms.

A container of the cosmetic composition and cosmetic product according to the present invention is not particularly limited either, and any container such as a jar, pump, tube, bottle, pressurized can dispensing container, pressure resistant aerosol container, light blocking container, compact container, cosmetic receptacle (kanazara), stick container, repeating container, spray container, divided container provided with a compound liquid dispensing opening, and the like can be filled with the cosmetic composition. Normal silicone-based formulations tend to separate easily in tubes, but the topical composition according to the present invention, particularly the cosmetic composition, has superior stability and, therefore, there is a benefit that the topical composition according to the present invention can be stored stably, even when charged into a tube container.

EXAMPLES

Hereinafter, the present invention is described in detail with reference to Practical Examples and Comparative Examples, but it should be understood that the present invention is not limited to these Practical Examples.

AB-type organopolysiloxane copolymers (P1 to P6) according to the present invention were synthesized according to the synthesis examples (synthesis methods) described below. Furthermore, in order to clarify the usefulness of the obtained organopolysiloxane copolymers, use as a surfactant (dispersing agent), use as an topical composition, and use as a cosmetic composition are described.

Structures of the AB-type organopolysiloxane copolymers P1 to P6 are as shown below.

(1) P1: An AB-type organopolysiloxane copolymer in which, in structural formula (PI) below, a=1 and b=4.

(2) P2: An AB-type organopolysiloxane copolymer in which, in structural formula (PI) below, a=3 and b=4.

(3) P3: An AB-type organopolysiloxane copolymer in which, in structural formula (PI) below, a=1 and b=1.

(4) P4: An AB-type organopolysiloxane copolymer in which, in structural formula (PI) below, a=1 and b=2.

Structural formula (PI):

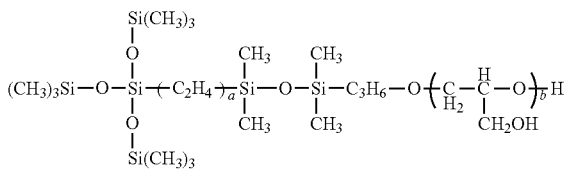

(5) P5: An AB-type organopolysiloxane copolymer in which, in structural formula (PII) below, a=1 and c=3.5.

(6) P6: An AB-type organopolysiloxane copolymer in which, in structural formula (PII) below, a=1 and c=9.2.

Structural formula (PII):

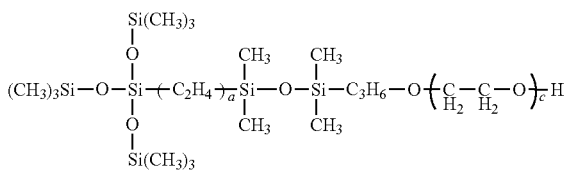

Practical Example 1

Synthesis Example 1

Synthesis of Organopolysiloxane Copolymer P1

624 g of 1,3-dihydrodisiloxane were added to a two-liter four-necked flask to which an agitation device, a thermometer, and a reflux condenser were attached, and heated to 75° C. Thereafter, a mixture of 300 g of tris(trimethylsiloxy)(vinyl)silane and 464 mg of a platinum catalyst was added dropwise to the flask over a period of three hours. After aging for one hour, ablation of the tris(trimethylsiloxy)(vinyl)silane was confirmed via gas chromatography. The excess 1,3-dihydrodisiloxane was removed under reduced pressure and, thereafter, a mixed solution of 412 g of tetraglycerin monoallyl ether and 412 g of IPA was added dropwise. After aging for six hours at 100° C., ablation of the Si—H bonds was confirmed using IR spectroscopy. Then, the volatile content was removed under reduced pressure. Thus, the organopolysiloxane copolymer P1 was obtained. Yield thereof was 600 g (79% yield). The molecular weight was 810. The product was identified and verified using NMR spectroscopy. The refractive index of the product was 1.451, and the product had light yellow, viscous liquid properties.

Practical Example 2

Synthesis Example 2

Synthesis of Organopolysiloxane Copolymer P2

300 g of 1,3-dihydrodisiloxane were added to a one-liter four-necked flask to which an agitation device, a thermometer, and a reflux condenser were attached, and heated to 75° C. Thereafter, a mixture of 169 g of tris(trimethylsiloxy)(hexenyl)silane and 235 mg of a platinum catalyst was added dropwise to the flask over a period of two hours. After aging for one hour, ablation of the tris(trimethylsiloxy)(hexenyl)silane was confirmed via gas chromatography. The excess 1,3-dihydrodisiloxane was removed under reduced pressure and, thereafter, a mixed solution of 198 g of tetraglycerin monoallyl ether and 198 g of IPA was added dropwise. After aging for six hours at 100° C., ablation of the Si—H bonds was confirmed using IR spectroscopy. Then, the volatile content was removed under reduced pressure. Thus, the organopolysiloxane copolymer P2 was obtained. Yield thereof was 310 g (80% yield). The molecular weight was 866. The product was identified and verified using NMR spectroscopy. The refractive index of the product was 1.450, and the product had light yellow, viscous liquid properties.

Practical Example 3

Synthesis Example 3

Synthesis of Organopolysiloxane Copolymer P3

936 g of 1,3-dihydrodisiloxane were added to a two-liter four-necked flask to which an agitation device, a thermometer, and a reflux condenser were attached, and heated to 75° C. Thereafter, a mixture of 450 g of tris(trimethylsiloxy)(vinyl)silane and 174 mg of a platinum catalyst was added dropwise to the flask over a period of four hours. After aging for one hour, ablation of the tris(trimethylsiloxy)(vinyl)silane was confirmed via gas chromatography. The excess 1,3-dihydrodisiloxane was removed under reduced pressure and, thereafter, 231 g of glycerin monoallyl ether was added dropwise. After aging for seven hours at 100° C., ablation of the Si—H bonds was confirmed using IR spectroscopy. Then, the volatile content was removed under reduced pressure. Thus, the organopolysiloxane copolymer P3 was obtained. Yield thereof was 800 g (97% yield). The molecular weight was 588. The product was identified and verified using NMR spectroscopy. The refractive index of the product was 1.431, and the product had light yellow, viscous liquid properties.

Practical Example 4

Synthesis Example 4

Synthesis of Organopolysiloxane Copolymer P4

658 g of 1,3-dihydrodisiloxane were added to a two-liter four-necked flask to which an agitation device, a thermometer, and a reflux condenser were attached, and heated to 75° C. Thereafter, a mixture of 316 g of tris(trimethylsiloxy)(vinyl)silane and 244 mg of a platinum catalyst was added dropwise to the flask over a period of three hours. After aging for one hour, ablation of the tris(trimethylsiloxy)(vinyl)silane was confirmed via gas chromatography. The excess 1,3-dihydrodisiloxane was removed under reduced pressure and, thereafter, a mixed solution of 200 g of diglycerin monoallyl ether and 200 g of IPA was added dropwise. After aging for two hours at 100° C., ablation of the Si—H bonds was confirmed using IR spectroscopy. Then, the volatile content was removed under reduced pressure. Thus, the organopolysiloxane copolymer P4 was obtained. Yield thereof was 515 g (79% yield). The molecular weight was 662. The product was identified and verified using NMR spectroscopy. The refractive index of the product was 1.439, and the product had light yellow, viscous liquid properties.

Practical Example 5

Synthesis Example 5

Synthesis of Organopolysiloxane Copolymer P5

936 g of 1,3-dihydrodisiloxane were added to a two-liter four-necked flask to which an agitation device, a thermometer, and a reflux condenser were attached, and heated to 75° C. Thereafter, a mixture of 450 g of tris(trimethylsiloxy)(vinyl)silane and 174 mg of a platinum catalyst was added dropwise to the flask over a period of four hours. After aging for one hour, ablation of the tris(trimethylsiloxy)(vinyl)silane was confirmed via gas chromatography. The excess 1,3-dihydrodisiloxane was removed under reduced pressure and, thereafter, 371 g of allyl polyether was added dropwise. After aging for three hours at 100° C., ablation of the Si—H bonds was confirmed using IR spectroscopy. Then, the volatile content was removed under reduced pressure. Thus, the organopolysiloxane copolymer P5 was obtained. Yield thereof was 930 g (99% yield). The molecular weight was 668. The product was identified and verified using NMR spectroscopy. The refractive index of the product was 1.433, and the product had light yellow, viscous liquid properties.

Practical Example 6

Synthesis Example 6

Synthesis of Organopolysiloxane Copolymer P6

558 g of 1,3-dihydrodisiloxane were added to a one-liter four-necked flask to which an agitation device, a thermometer, and a reflux condenser were attached, and heated to 75° C. Thereafter, a mixture of 268 g of tris(trimethylsiloxy)(vinyl)silane and 207 mg of a platinum catalyst was added dropwise to the flask over a period of three hours. After aging for one hour, ablation of the tris(trimethylsiloxy)(vinyl)silane was confirmed via gas chromatography. The excess 1,3-dihydrodisiloxane was removed under reduced pressure and, thereafter, a solution of 381 g of allyl polyether was added dropwise. After aging for four hours at 100° C., ablation of the Si—H bonds was confirmed using IR spectroscopy. Then, the volatile content was removed under reduced pressure. Thus, the organopolysiloxane copolymer P6 was obtained. Yield thereof was 671 g (88% yield). The molecular weight was 919. The product was identified and verified using NMR spectroscopy. The refractive index of the product was 1.443, and the product had light yellow, viscous liquid properties.

Synthesis of the Modified Disiloxanes for Use in Practical Examples 7 to 11, where One Terminal is a Carbosiloxane Synthesis Example 7

Synthesis of the Modified Disiloxane According to Structural Formula (PX) Below, where a=1

Structural formula (PX):

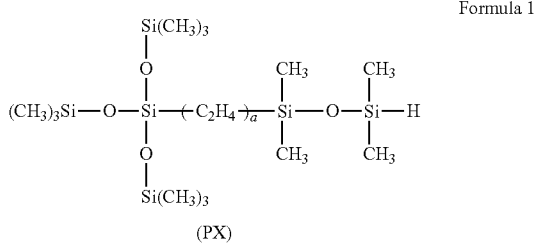

Formula 1

(PX)

1040 g of 1,3-dihydrodisiloxane were added to a two-liter four-necked flask to which an agitation device, a thermometer, and a reflux condenser were attached, and heated to 75° C. Thereafter, a mixture of 500 g of tris(trimethylsiloxy)(vinyl)silane and 193 mg of a platinum catalyst was added dropwise to the flask over a period of five hours. After aging for one hour, ablation of the tris(trimethylsiloxy)(vinyl)silane was confirmed via gas chromatography. The excess 1,3-dihydrodisiloxane was recovered by distilling under ambient pressure, and then distillation under reduced pressure was performed. Thus, a 1-(tris(trimethylsiloxy)(silyl)ethyl)-3-hydrodisiloxane was obtained. A boiling point thereof was 144° C./20 torr, and yield was 558.56 g (79% yield). The molecular weight was 456. The product was identified using NMR spectroscopy. Purity analyzed using GC chromatography was 95%. The product was a colorless, transparent liquid.

Practical Example 7

Synthesis Example 8

Synthesis of Organopolysiloxane Copolymer P8

A mixed solution of 291 g of tetraglycerin monoallyl ether and 291 g of IPA was added to a one-liter four-necked flask to which an agitation device, a thermometer, and a reflux condenser were attached, and heated to 75° C. After adding 296 mg of a platinum catalyst, 300 g of the chemical substance obtained aforehand was added dropwise. After aging for eight hours, ablation of the Si—H bonds was confirmed using IR spectroscopy. Then, the volatile content was removed under reduced pressure. Thus, the compound of Synthesis Example 1 (organopolysiloxane copolymer P1) was obtained. Yield thereof was 421 g (79% yield). The product was identified and verified using NMR spectroscopy.

Practical Example 8

Synthesis Example 9

Synthesis of Organopolysiloxane Copolymer P3

109 g of glycerin monoallyl ether were added to a 500 ml four-necked flask to which an agitation device, a thermometer, and a reflux condenser were attached, and heated to 75° C. After adding 76 mg of a platinum catalyst, 300 g of the chemical substance obtained aforehand was added dropwise. After aging for seven hours, ablation of the Si—H bonds was confirmed using IR spectroscopy. Then, the volatile content was removed under reduced pressure. Thus, the compound of Synthesis Example 3 (organopolysiloxane copolymer P3) was obtained. Yield thereof was 349 g (90% yield). The product was identified and verified using NMR spectroscopy.

Practical Example 9

Synthesis Example 10

Synthesis of Organopolysiloxane Copolymer P4

A mixed solution of 200 g of diglycerin monoallyl ether and 200 g of IPA was added to a one-liter four-necked flask to which an agitation device, a thermometer, and a reflux condenser were attached, and heated to 100° C. After adding 139 mg of a platinum catalyst, 354 g of the chemical substance obtained aforehand was added dropwise. After aging for two hours, ablation of the Si—H bonds was confirmed using IR spectroscopy. Then, the volatile content was removed under reduced pressure. Thus, the compound of Synthesis Example 4 (organopolysiloxane copolymer P4) was obtained. Yield thereof was 515 g (99% yield). The product was identified and verified using NMR spectroscopy.

Practical Example 10

Synthesis Example 11

Synthesis of Organopolysiloxane Copolymer P5

174 g of allyl polyether were added to a 500 ml four-necked flask to which an agitation device, a thermometer, and a reflux condenser were attached, and heated to 80° C. After adding 175 mg of a platinum catalyst, 300 g of the chemical substance obtained aforehand was added dropwise. After aging for eight hours, ablation of the Si—H bonds was confirmed using IR spectroscopy. Then, the volatile content was removed under reduced pressure. Thus, the compound of Synthesis Example 5 (organopolysiloxane copolymer P5)

was obtained. Yield thereof was 407 g (93% yield). The product was identified and verified using NMR spectroscopy.

Practical Example 11

Synthesis Example 12

Synthesis of Organopolysiloxane Copolymer P6

A mixed solution of 381 g of allyl polyether and 381 g of IPA was added to a one-liter four-necked flask to which an agitation device, a thermometer, and a reflux condenser were attached, and heated to 80° C. After adding 170 mg of a platinum catalyst, 300 g of the chemical substance obtained aforehand was added dropwise. After aging for eight hours, ablation of the Si—H bonds was confirmed using IR spectroscopy. Then, the volatile content was removed under reduced pressure. Thus, the compound of Synthesis Example 6 (organopolysiloxane copolymer P6) was obtained. Yield thereof was 605 g (99% yield). The product was identified and verified using NMR spectroscopy.

Water-in-oil emulsion compositions having the formulations shown in Table 1 were prepared and were evaluated for emulsion stability and functionality (feeling to touch and sensation during use) according to the following evaluation standards. The results are shown in Table 1. In the table, "parts" is an abbreviation for "parts by weight".

In the table, "Synthesis Example—" refers to the AB-type organopolysiloxane copolymer of the synthesis example (where "—" is replaced by a synthesis example number). Additionally, in the table, SS2910 and FZ2233 used in the Comparative Experiments are the following products.

(1) SS2910: Polyether-modified silicone (trade designation: SS2910, manufactured by Dow Corning Toray Co., Ltd.)

(2) FZ2233: Straight block copolymer (ABn)-type polyether-modified silicone (trade designation: FZ-2233, manufactured by Dow Corning Toray Co., Ltd.)

Evaluation of Emulsion Stability

The water-in-oil emulsion composition of each formulation was allowed to sit at rest for one month at room temperature (25° C.) and 40° C. Then, changes in the emulsion state before and after the sitting at rest were evaluated according to the following standards.
⊚: No change
o: Slight amount of separation
Δ: Agglomeration, reduced viscosity
x: Separation and/or agglomeration Evaluation of Functionality Evaluation Standards Ten panelists evaluated sensation during use (feeling to touch and spreadability) when using the water-in-oil emulsion composition of each formulation (subject for evaluation) as a cosmetic composition. Each panelist was made to answer a questionnaire in which the quality of feeling to touch and spreadability were scored on a scale of 1 to 5, with 1 being inferior, 5 being superior, and 2, 3, and 4 being mid-range scores. The scores were averaged and recorded as the evaluation results for sensation during use.

TABLE 1

Formulation and evaluation of water-in-oil emulsion compositions

| | | Practical Examples | | | | | | | | | Comparative Examples | | | | | |
|---|---|---|---|---|---|---|---|---|---|---|---|---|---|---|---|---|
| | | 13 | 14 | 15 | 16 | 17 | 18 | 19 | 20 | 21 | 1 | 2 | 3 | 4 | 5 | 6 |
| Synthesis Example 1: Organopolysiloxane Copolymer P1 | | 2 | 2 | 2 | | | | | | | | | | | | |
| Synthesis Example 3: Organopolysiloxane Copolymer P3 | | | | | 2 | 2 | 2 | | | | | | | | | |
| Synthesis Example 5: Organopolysiloxane Copolymer P5 | | | | | | | | 2 | 2 | 2 | | | | | | |
| SS2910 | | | | | | | | | | | 2 | 2 | 2 | | | |
| FZ2233 | | | | | | | | | | | | | | 2 | 2 | 2 |
| SH200-2cs | | 8 | 8 | 8 | 8 | 8 | 8 | 8 | 8 | 8 | 8 | 8 | 8 | 8 | 8 | 8 |
| SH200-6cs | | 10 | | | 10 | | | 10 | | | 10 | | | 10 | | |
| Trioctanoin | | | 10 | | | 10 | | | 10 | | | 10 | | | 10 | |
| Isododecane | | | | 10 | | | 10 | | | 10 | | | 10 | | | 10 |
| Purified water | | 79 | 79 | 79 | 79 | 79 | 79 | 79 | 79 | 79 | 79 | 79 | 79 | 79 | 79 | 79 |
| Sodium chloride | | 1 | 1 | 1 | 1 | 1 | 1 | 1 | 1 | 1 | 1 | 1 | 1 | 1 | 1 | 1 |
| Emulsion stability (one-month) | Room temperature | O | ⊚ | Δ | X | X | X | O | O | O | O | O | Δ | O | O | Δ |
| | 40° C. | O | ⊚ | Δ | X | X | X | Δ | O | Δ | O | Δ | Δ | O | Δ | Δ |
| Quality of feeling to touch and spreadability | | 4.5 | 4.7 | 4.4 | 4.5 | 4.5 | 4.6 | 4.5 | 4.6 | 4.7 | 3.1 | 3 | 3 | 2.7 | 2.6 | 2.7 |

Evaluation of Dispersion Stability

Slurry-like micro-particle dispersions were prepared according to the formulations and preparation methods shown in Dispersion Preparation 1 to Dispersion Preparation 3 below. These micro-particle dispersions were then evaluated from the standpoints of dispersion characteristics and flow characteristics. The results are shown in Tables 1 and 2. The components used in the preparation of each dispersion are as follows.

(1) micro-particle powder: Fine particulate titanium oxide
   Trade designation: MTY-100SAS (manufactured by Tayca Corporation) Particle size: 15 nm (2) Comparative sample 1: Polyether-modified silicone Product Name: SS2910 (manufactured by Dow Corning Toray Co., Ltd.)
(3) Comparative sample 2: Polyglycerin-modified silicone
(4) Dispersing medium: Decamethyl cyclopentasiloxane Product Name: DC245 (manufactured by Dow Corning Toray Co., Ltd.)

Practical Example 22

Preparation of Dispersion D1

A slurry-like dispersion (D1) was produced by mixing 20 g of the micro-particle powder, 5 g of the organopolysiloxane copolymer (P1) of Synthesis Example 1, and 25 g of decamethyl cyclopentasiloxane; adding 200 g of zirconia beads (Φ0.8 mm) thereto; and mixing the mixture using a paint shaker for one hour.

Comparative Example 7

Preparation of Dispersion D2

A slurry-like dispersion (D2) was produced the same as in the Preparation of dispersion D1, except that a polyether-modified silicone (Comparative Sample 1) was used in place of the organopolysiloxane copolymer (P1) of Synthesis Example 1.

Comparative Example 8

Preparation of Dispersion D3

A slurry-like dispersion (D3) was produced the same as in the Preparation of dispersion D1, except that a polyglycerin-modified silicone (Comparative Sample 2) was used in place of the organopolysiloxane copolymer (P1) of Synthesis Example 1.

Practical Example 23

Preparation of Dispersion D4

A slurry-like dispersion (D4) was produced by mixing 20 g of the micro-particle powder, 5 g of the organopolysiloxane copolymer (P1) of Synthesis Example 1, 20 g of decamethyl cyclopentasiloxane, and 5 g of torioctanoin; adding 200 g of zirconia beads (Φ0.8 mm) thereto; and mixing the mixture using a paint shaker for one hour.

Comparative Example 9

Preparation of Dispersion D5

A slurry-like dispersion (D5) was produced the same as in the Preparation of dispersion D4, except that a polyether-modified silicone (Comparative Sample 1) was used in place of the organopolysiloxane copolymer (P1) of Synthesis Example 1.

Comparative Example 10

Preparation of Dispersion D6

A slurry-like dispersion (D6) was produced the same as in the Preparation of dispersion D4, except that a polyglycerin-modified silicone (Comparative Sample 2) was used in place of the organopolysiloxane copolymer (P1) of Synthesis Example 1.

Using the following measurement device and measurement conditions, the rheology of each of the slurry-like dispersions described above was measured, and each dispersion was evaluated from the standpoints of dispersion characteristics and flow characteristics.

Evaluation Method

Evaluation device: Cone and plate-type viscometer AR1000-N, manufactured by TA Instruments Japan Inc.

Measurement conditions: 40 mm 1° steel geometry, 0.01 to 1,000 s$^{-1}$ shear rate, 25° C.

Results

Evaluation results of slurry-like dispersions (D1) to (D3) in which decamethyl cyclopentasiloxane was used as the dispersing medium are shown in FIG. 1.

Evaluation results of slurry-like dispersions (D4) to (D6) in which a mixed solution including decamethyl cyclopentasiloxane and trioctanoin at a ratio of 4:1 is used as the dispersing medium are shown in FIG. 2.

In cases where the dispersion stability of the powder in the dispersion was excellent, the flow characteristics thereof ideally reflect the flow characteristics of the silicone dispersing medium, and display Neutonian behavior in which viscosity is constant, and not restricted by the shear rate.

The slurry-like dispersions (D1) and (D4) prepared using the organopolysiloxane copolymer (P1) of Synthesis Example 1 both had low viscosities, and regardless of the polarity of the dispersing medium, displayed Neutonian behavior in which viscosity was constant, and not restricted by the shear rate. In other words, these dispersions had extremely high dispersion stability. (see FIGS. 1 and 2)

With the dispersions prepared using Comparative Sample 1 or Comparative Sample 2, in cases when only decamethyl cyclopentasiloxane was used as the dispersing medium, both dispersions displayed Neutonian behavior and excellent dispersion stability.

However, in cases where a dispersing medium was used in which 20 wt. % of the high polarity solvent trioctanoin was mixed, in Comparative Sample 1, the viscosity increased significantly and the powder agglomerated, which indicates a decline in dispersion stability. Additionally, with the dispersion prepared using Comparative Sample 2, while there was not a large change in viscosity due to the difference in polarity of the dispersing medium, viscosity was higher comparted to the slurry-like dispersion prepared using the organopolysiloxane copolymer (P1) of Synthesis Example 1.

Formulation Examples

Hereinafter, formulation examples of the cosmetic composition of the present invention in which the organopolysiloxane copolymer of the present invention is compounded are described. However, it should be understood that the present invention is not limited to these examples. Additionally, "Synthesis Example X" as shown in the compositions of each of the formulation examples refers to the organopolysiloxane copolymer obtained in the Synthesis Example of the same number (where "X" is replaced by a number).

Formulation Example 1

Toilet Water

| | |
|---|---|
| 1. Synthesis Example 1 | 1 part |
| 2. Dipropylene glycol | 1 part |
| 3. Dimethicone (6 cs) | 0.8 parts |
| 4. Phenyl trimethicone (see note 1) | 0.8 parts |
| 5. PEG-12 dimethicone (see note 2) | 1.4 parts |
| 6. Ethanol | 20.3 parts |
| 7. Trilaureth-4 phosphate | 0.15 parts |
| 8. PEG-6 cocamide | 0.3 parts |
| 9. PEG-3 cocamide | 0.2 parts |
| 10. Purified water | 44.9 parts |
| 11. Carnosine | 0.1 parts |
| 12. Citric acid | 0.05 parts |
| 13. Polyoxypropylene methylglucoside | 0.4 parts |
| 14. Carbomer (2% aqueous solution) | 18 parts |
| 15. Sodium hydroxide (1% aqueous solution) | 10.5 parts |

Note 1:
Used SH556, manufactured by Dow Corning Toray Co., Ltd.
Note 2:
Used SH3775M, manufactured by Dow Corning Toray Co., Ltd.

Procedure

1. Mix components 1 to 9 (A layer).
2. Mix components 10 and 11, and add components 14 and 15 (B layer).
3. Add the A layer to the B layer and emulsify.

Effects

The obtained toilet water has a stable emulsified state, displays little stickiness, and has a superior feeling to touch.

Formulation Example 2

Cleansing Gel

| | |
|---|---|
| 1. Synthesis Example 1 | 1 part |
| 2. Dipropylene glycol | 1 part |
| 3. Dimethicone (6 cs) | 0.8 parts |
| 4. Phenyl trimethicone | 0.8 parts |
| 5. PEG-12 dimethicone (see note 1) | 1.4 parts |
| 6. Ethanol | 20.3 parts |
| 7. Dimethicone (50 cs) | 10 parts |
| 8. Purified water | 46 parts |
| 9. Carbomer | 0.45 parts |
| 10. Sodium hydroxide (1%) | 10.5 parts |
| 11. Polyoxypropylene methylglucoside | 0.4 parts |
| 11. 1,3-butylene glycol | 7 parts |
| 13. Ethanol | 5 parts |
| 14. Glycerin | 8 parts |
| 15. Preservative | 0.05 parts |

Note 1:
Used SH3775M, manufactured by Dow Corning Toray Co., Ltd.

Procedure

1. Components 1 to 7 are mixed. (mixture 1)
2. Components 8 to 10 are mixed. (mixture 2)
3. Components 11 to 15 are mixed. (mixture 3)
4. The mixture 1 is added to the mixture 2 and this mixture is emulsified.
5. Then, the mixture 3 is added and this mixture is agitated.

Effects

The obtained cleansing gel has a high silicone content, displays little stickiness, and has a superior feeling to touch.

Formulation Example 3

Sunscreen Cream (O/W Cream)

| | |
|---|---|
| 1. Synthesis Example 2 | 1 part |
| 2. Dipropylene glycol | 1 part |
| 3. Sodium laureth-3 (POE) phosphate | 0.05 parts |
| 4. Ethylhexyl methoxycinnamate | 8.5 parts |
| 5. t-butyl methoxybenzoyl methane | 1.5 parts |
| 6. Phenyl trimethicone | 3.4 parts |
| 7. PEG12-dimethicone (see note 1) | 0.7 parts |
| 8. Dimethicone (6 cs) | 1.4 parts |
| 9. Ethanol | 7.35 parts |
| 10. Bis(hydroxyethoxy)dimethicone (see note 2) | 1 part |
| 11. Carbomer (2% solution) | 22.5 parts |
| 12. Purified water | bal. |
| 13. Sodium hydroxide (1% aq) | 10.5 parts |
| 14. Ethanol | 2 parts |
| 11. 1,3-butylene glycol | 5 parts |
| 16. Glycerin | 5 parts |
| 17. Preservative | 0.05 parts |

Note 1:
Used SS2804, manufactured by Dow Corning Toray Co., Ltd.
Note 2:
Used DH5562, manufactured by Dow Corning Toray Co., Ltd.

Procedure

1. Components 1 to 10 are mixed. (mixture 1)
2. Components 11 to 16 are mixed. (mixture 2)
3. The mixture 1 is added to the mixture 2 and this mixture is emulsified.
4. Then, the mixture 3 is added and this mixture is agitated.

Effects

The obtained sunscreen cream has a stable emulsified state, and displays water repellency when applied to skin.

Formulation Example 4

Sunscreen (Shakeup Type)

| | |
|---|---|
| 1. Octyl methoxycinnamate | 10 parts |
| 2. Titanium oxide slurry (see note 1) | 1 part |
| 3. Zinc oxide slurry (see note 2) | 32 parts |
| 4. Cyclopentasiloxane | 20.2 parts |
| 5. Dimethicone crosspolymer | 3 parts |
| 6. Trimethylsiloxysilicate | 3.3 parts |
| 7. Preservative | 0.1 parts |
| 8. Ethanol | 5 parts |
| 9. 1,3-butylene glycol | 3 parts |
| 10. Purified water | bal. |

Procedure

1. A titanium oxide slurry is produced by mixing a formulation of 40 parts of a fine particulate titanium oxide (MTY-100SAS, manufactured by Tayca Corporation), 50 parts of decamethylpentacyclosiloxane, and 10 parts of Synthesis Example 3. Zirconia beads (Φ0.8 mm) are added thereto, and the mixture is agitated using a paint shaker.
2. A zinc oxide slurry is produced by mixing a formulation of 40 parts of a fine particulate zinc oxide (MZY-505S, manufactured by Tayca Corporation), 50 parts of decamethylpentacyclosiloxane, and 10 parts of Synthesis Example 3. Zirconia beads (Φ0.8 mm) are added thereto, and the mixture is agitated using a paint shaker.
3. Components 1 to 8 are mixed.
4. Components 9 and 10 are mixed with the mixture of step 3, and this mixture is emulsified.

Effects

The obtained sunscreen has reduced stickiness and superior sensation during use when applied on skin, and provides lasting ultraviolet light protection effects.

Formulation Example 5

Sunscreen Cream (W/O Type)

| | |
|---|---|
| 1. Octyl methoxycinnamate | 7.5 parts |
| 2. Cyclopentasiloxane | 8 parts |
| 3. Dimethicone (6 cs) | 2 parts |
| 4. Copolymer of cyclopentasiloxane and (acrylates/polytrimethylsiloxy methacrylate) (see note 1) | 1 part |
| 5. Didimethicone crosspolymer (see note 2) | 2 parts |
| 6. Polysilicone 13 (see note 3) | 1 part |
| 7. Synthesis Example 1 | 1 part |
| 8. Titanium oxide slurry (30%) (see note 4) | 2 parts |
| 9. Zinc oxide slurry (50%) (see note 5) | 10 parts |
| 10. Sodium chloride | 1 part |
| 11. Panthenol | 0.5 parts |
| 12. Purified water | bal. |
| 13. Glycerin | 2 parts |
| 14. Preservative | 0.05 parts |

Note 1:
Used FA4001CM Silicone Acrylate, manufactured by Dow Corning Toray Co., Ltd.
Note 2:
Used DC9041, manufactured by Dow Corning Toray Co., Ltd.
Note 3:
Used straight block interpolymer (ABn)-type polyether-modified silicone (FZ-2233, manufactured by Dow Corning Toray Co., Ltd.)
Note 4:
Other than using Synthesis Example 6 as the dispersing agent, the slurry was produced according to the same formulation as the titanium oxide slurry of Formulation Example 4.
Note 5:
Other than using Synthesis Example 6 as the dispersing agent, the slurry was produced according to the same formulation as the zinc oxide slurry of Formulation Example 4.

Procedure

1. Components 1 to 9 are mixed. (mixture 1)
2. Components 10 to 14 are mixed. (mixture 2)
3. The mixture 2 is added to the mixture 1 while agitating using a disper.

Effects

Because the powder is efficiently dispersed, the obtained sunscreen cream has reduced stickiness and superior sensation during use when applied on skin, and provides lasting ultraviolet light protection effects.

Formulation Example 6

Liquid Foundation

| | |
|---|---|
| 1. Dextrin palmitate | 2.1 parts |
| 2. Tri(capryl-capric acid)glyceryl | 5 parts |
| 3. PEG/PPG-18/18 dimethicone (see note 1) | 10 parts |
| 4. Synthesis Example 10 | 1.9 parts |
| 5. Dimethicone (2 cs) | 10 parts |
| 6. Cyclopenta cyclosiloxane | 10 parts |
| 7. Silicone treated red, yellow, or black iron oxide | 3.5 parts |
| 8. Mica | 3.5 parts |
| 9. Silicone treated titanium oxide | 4 parts |
| 10. Purified water | bal. |
| 11. Sodium chloride | 1 part |

Note 1:
Used BY11-030, manufactured by Dow Corning Toray Co., Ltd.

Procedure

A liquid foundation is obtained by mixing components 1 to 6 and adding/dispersing therein components 6 to 9, which have been pre-crushed. Then, the mixture is emulsified while adding the dissolved/mixed components 10 and 11 in small amounts.

Effects

The obtained foundation has superior emulsion stability and superior cosmetic retainability.

Formulation Example 7

Wrinkle Concealing Cosmetic Composition

| | |
|---|---|
| 1. Dimethicone/Vinyldimethicone crosspolymer—silica (see note 1) | 4 parts |
| 2. Synthesis Example 5 | 3 parts |
| 3. PEG/PPG-18/18 dimethicone | 7 parts |
| 4. Cyclopentasiloxane | 16 parts |
| 5. PPG-myristyl ether | 0.5 parts |
| 6. Purified water | bal. |
| 7. Glycerin | 5 parts |
| 8. Sodium chloride | 2 parts |
| 9. Preservative | 0.5 parts |

Note 1:
Used 9701 Cosmetic Powder, manufactured by Dow Corning Toray Co., Ltd.

Procedure

1. Components 1 to 5 are mixed. (mixture 1)
2. Components 6 to 9 are mixed. (mixture 2)
3. The mixture 2 is added to the mixture 1 and this mixture is emulsified.

Effects

The obtained cosmetic composition has superior emulsion stability, displays little stickiness, and has superior sensation during use.

Formulation Example 8

Rouge

| | |
|---|---|
| 1. Ceresin wax | 10 parts |
| 2. Paraffin wax | 8 parts |
| 3. Candelilla wax | 2 parts |
| 4. Liquid paraffin | 21.8 parts |
| 5. Liquid lanolin | 10 parts |
| 6. Isodecyl isononanoate | 25 parts |
| 7. Tri(capryl-capric acid)glyceryl | 5 parts |
| 8. Synthesis Example 9 | 9 parts |
| 9. Copolymer of isododecane and (acrylates/polytrimethylsiloxy methacrylate) (see note 1) | 1 part |
| 10. Titanium oxide | 2 parts |
| 11. Red No. 201 | 2 parts |
| 12. Red No. 202 | 1 part |
| 13. Yellow No. 4, Aluminum Lake | 3 parts |
| 14. Antioxidant | 0.1 parts |
| 15. Perfume | 0.1 parts |

Note 1:
Used FA4002ID Silicone Acrylate, manufactured by Dow Corning Toray Co., Ltd.

Procedure

All of the components are mixed and poured into a mold.

Effects

The obtained rouge has excellent compatibility with the oil-based raw materials, has superior storage stability, and has superior color development and luster when applied.

Formulation Example 9

Eye Shadow

| Components | (wt. %) |
|---|---|
| 1. Dimethylpolysiloxane (2 cs) | 13.0 |
| 2. Dimethylpolysiloxane (6 cs) | 12.0 |
| 3. Synthesis Example 11 | 2.0 |
| 4. PEG(10)lauryl ether | 0.5 |
| 5. Octylsilane treated titanium oxide | 6.2 |
| 6. Octylsilane treated sericite | 4.0 |
| 7. Octylsilane treated mica | 6.0 |
| 8. Sodium chloride | 2.0 |
| 9. Propylene glycol | 8.0 |
| 10. Preservative | q.s. |
| 11. Perfume | q.s. |
| 12. Purified water | bal. |

Procedure

A: Components 1 to 4 are mixed, and components 5 to 7 are added and dispersed uniformly.

B: Components 8 to 12 are dissolved uniformly.

C: B is added to A in small amounts and emulsified. Thus, an eye shadow is obtained.

Effects

The obtained eye shadow spreads smoothly when applying and has superior color development.

Formulation Example 10

Mascara

| Components | (wt. %) |
|---|---|
| 1. Isohexadecane | 34.0 |
| 2. Dimethicone (6 cs) | 1.5 |
| 3. Trimethylsiloxysilicate (see note 1) | 31.0 |
| 4. Dextrin fatty acid ester | 15.0 |
| 5. Composition of Synthesis Example 8 | 3.0 |
| 6. Organo-modified bentonite | 1.5 |
| 7. Hydrophobized silicic anhydride | 2.0 |
| 8. Nylon fiber (average length: 2 μm) | 2.0 |
| 9. Carbon black | 10.0 |

Procedure

Components 1 to 9 are uniformly mixed. Then, a container is filled with the mixture. Thus, a mascara is obtained.

Effects

The obtained mascara has a deep appearance when applied and has superior luster. Moreover adhesion to eyelashes is excellent and durability is superior.

Industrial Applicability

The novel organopolysiloxane copolymer according to the present invention can be used as a topical composition, particularly in applications other than those of cosmetic compositions. Examples thereof include varnishes or coating additives having superior heat resistance, weather resistance, or electrical properties; foam stabilizers or modifying agents for polyol base compounds used in various urethane and foam materials; debonding agents or release agents; antifoaming agents; grease or oil compounds; modifying agents, additives, or surface treatment agents use for oil, rubber, or resin of insulating, glazing, water repelling, heating mediums, cooling mediums, and lubricants; compounds, modifying agents, and precursors for silane coupling agents; coating materials or sealing materials for buildings or linings; protective agents, lubricants, or buffer agents for fiber optics and electrical wiring; and the like. However, the novel organopolysiloxane copolymer according to the present invention is not limited to such applications.

The invention claimed is:

1. An organopolysiloxane copolymer expressed by the following general formula (1):

General Formula (1):

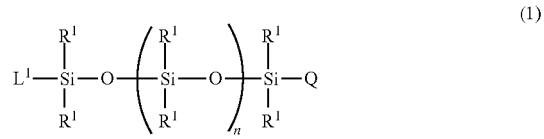

wherein $R^1$ independently represents an aryl group having from 1 to 10 carbons or an alkyl group having from 1 to 10 carbons, n is a number in a range of 0 to 10, Q is a hydrophilic segment and a linking group, wherein said hydrophilic segment is derived from a hydrophilic compound selected from polyhydric alcohols comprising glycerin or polyglycerines, said hydrophilic segment bonded to the silicon atom via said linking group that is at least divalent, said hydrophilic segment comprising at least one hydrophilic unit selected from hydrophilic units expressed by the following structural formulae (3-2) to (3-4):

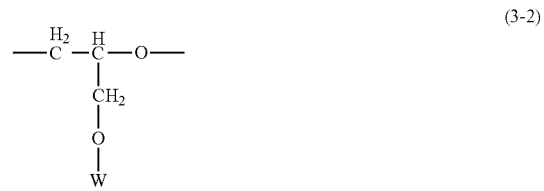

wherein W is a hydrogen atom or an alkyl group having from 1 to 20 carbons;

wherein W is defined above;

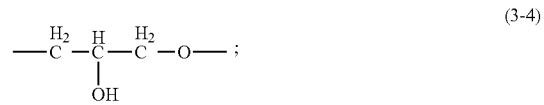

and $L^1$ is a silylalkyl group expressed by the following general formula (2) when i=1;

General Formula (2):

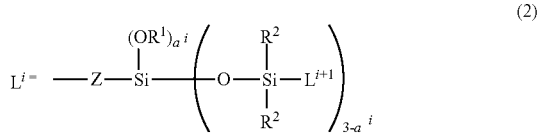

(2)

wherein $R^1$ is defined above, $R^2$ is a phenyl group or an alkyl group having from 1 to 6 carbons, Z is a divalent organic group; i represents a generation of the silylalkyl group represented by $L^i$, and is an integer of 1 to c with c being an integer from 1 to 10, and $L^{i+1}$ is a generation of the silylalkyl group when i is less than c and is a methyl group or a phenyl group at terminal $L^{i+1}$ generations; and $a^i$ is a number in a range of 0 to 3.

2. The organopolysiloxane copolymer according to claim 1, wherein in the general formula (1), $L^1$ is a functional group expressed by the following general formula (2-1) or general formula (2-2):

General Formula (2-1):

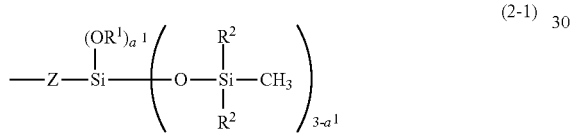

(2-1)

General Formula (2-2):

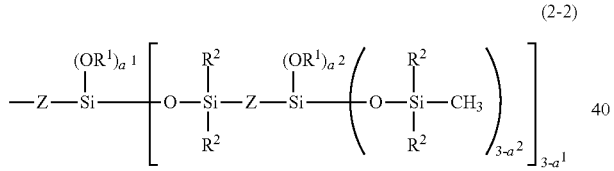

(2-2)

wherein $R^1$, $R^2$, and Z are defined above, and $a^1$ and $a^2$ are each independently numbers in a range of 0 to 3.

3. The organopolysiloxane copolymer according to claim 1, wherein in the general formula (1)
Q is a hydrophilic segment and a linking group, wherein said hydrophilic segment is derived from a hydrophilic compound selected from polyhydric alcohols comprising glycerin or polyglycerines, said hydrophilic segment bonded to the silicon atom via said linking group that is at least divalent, comprising at least one linearly bonded hydrophilic unit selected from hydrophilic units expressed by the structural formulae (3-2) to (3-4) above; or Q is a hydrophilic segment and a linking group, wherein said hydrophilic segment is derived from a hydrophilic compound selected from polyhydric alcohols comprising glycerin or polyglycerines, said hydrophilic segment bonded to the silicon atom via said linking group that is at least divalent, wherein said hydrophilic segment comprises at least one hydrophilic unit selected from hydrophilic units expressed by structural formulae (3-2) to (3-4) above, and further comprises a branch unit selected from structural formulas (3-5) to (3-7) below:

(3-5)

(3-6)

(3-7)

4. The organopolysiloxane copolymer according to 3, wherein Q is selected from the group consisting of:

General Formula (4-1):

(4-1)

wherein $R^3$ is an organic group having (p+1) valency, and p is a number that is greater than or equal to 1; $X^1$ are each independently at least one hydrophilic unit selected from the hydrophilic units expressed by the general formulae (3-2) to (3-4) above, and m is a number in a range of 1 to 100; and $R^4$ is a hydrogen atom or a group selected from the group consisting of acyl groups, glycidyl groups, and alkyl groups having from 1 to 20 carbons;

General Formula (4-2-2):

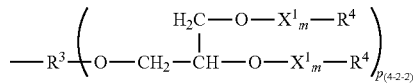

wherein $R^3$, $X^1$, $R^4$, m, and p are defined above;

General Formula (4-3-2):

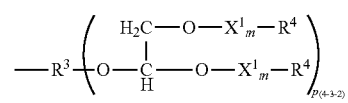

wherein $R^3$, $X^1$, $R^4$, m, and p are defined above; and

General Formula (4-4-2):

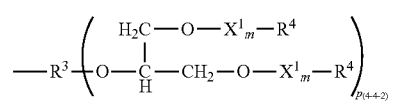

wherein $R^3$, $X^1$, $R^4$, m, and p are defined above.

5. The organopolysiloxane copolymer according to claim 1, expressed by any one of structural formulae (1-1) to (1-4) below:

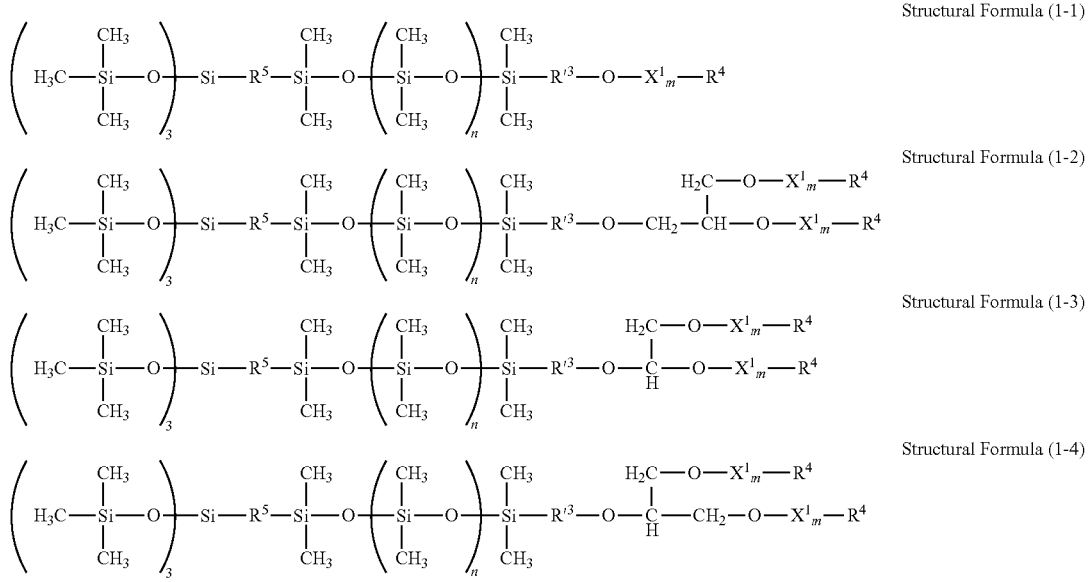

wherein in structural formulae (1-1) to (1-4), n is a number in a range from 0 to 10 and m is a number in a range from 1 to 100;

$X^1$ are each independently at least one hydrophilic unit selected from the hydrophilic units expressed by the general formulae (3-2) to (3-4) above;

$R^{13}$ is a group selected from divalent organic groups expressed by general formulae (5-1), (5-1-2), (5-1-3), and (5-2) below;

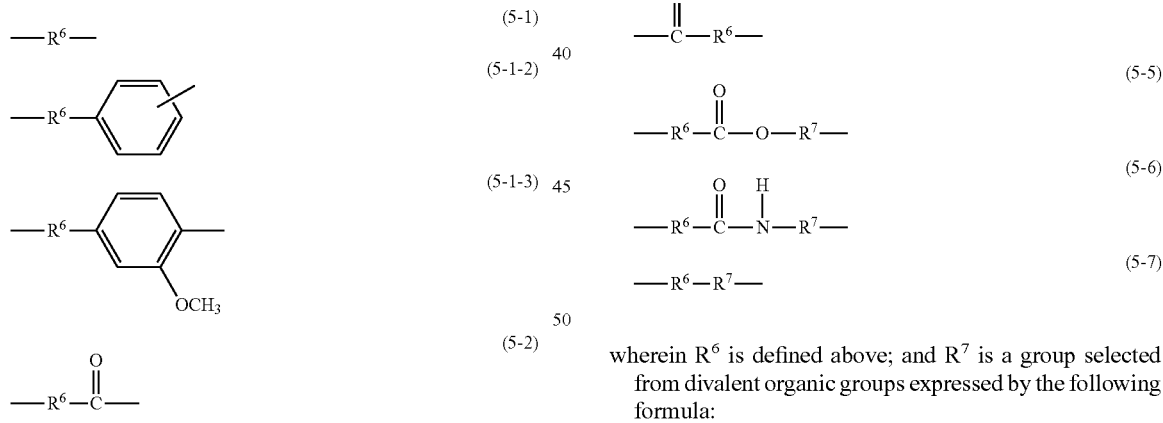

wherein $R^6$ may have a substituent, and each $R^6$ is independently a straight or branched chain alkylene group having from 2 to 22 carbons or a straight or branched chain alkenylene group having from 2 to 22 carbons, or an arylene group having from 6 to 22 carbons;

$R^4$ is a hydrogen atom or a group selected from the group consisting of acyl groups having from 1 to 20 carbons, glycidyl groups having from 1 to 20 carbons, and alkyl groups having from 1 to 20 carbons;

$R^5$ is a group selected from divalent organic groups expressed by general formulae (5-1) to (5-7) below;

$$—R^6— \quad (5\text{-}1)$$

$$—R^6—\overset{O}{\underset{\|}{C}}— \quad (5\text{-}2)$$

$$—R^6—\overset{O}{\underset{\|}{C}}—O—R^6— \quad (5\text{-}3)$$

$$—\overset{O}{\underset{\|}{C}}—R^6— \quad (5\text{-}4)$$

$$—R^6—\overset{O}{\underset{\|}{C}}—O—R^7— \quad (5\text{-}5)$$

$$—R^6—\overset{O}{\underset{\|}{C}}—\overset{H}{\underset{|}{N}}—R^7— \quad (5\text{-}6)$$

$$—R^6—R^7— \quad (5\text{-}7)$$

wherein $R^6$ is defined above; and $R^7$ is a group selected from divalent organic groups expressed by the following formula:

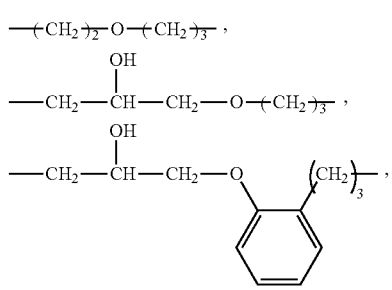

-continued

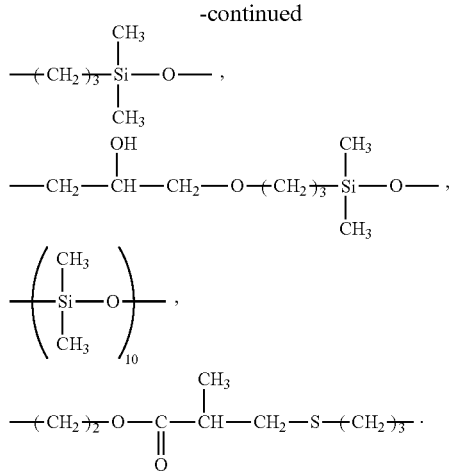

6. The organopolysiloxane copolymer according to claim 1, wherein n is equal to 0.

7. A surfactant comprising the organopolysiloxane copolymer described in claim 1.

8. A powder treatment agent comprising the organopolysiloxane copolymer described in claim 1.

9. A topical composition comprising the organopolysiloxane copolymer described in claim 1.

10. The topical composition according to claim 9 that is a cosmetic composition or a medicament.

11. The cosmetic composition according to claim 10 comprising the following components:
   (a) from 0.1 to 99.9 wt. % of the organopolysiloxane copolymer; and
   (b) from 99.9 to 0.1 wt. % of a silicone oil, a nonpolar organic compound, or an oil agent.

12. The cosmetic composition according to claim 10, wherein the cosmetic composition is a skin care product, a cosmetic product for hair, an anti-perspirant product, a makeup product, or an ultraviolet light blocking product.

13. A method for manufacturing the organopolysiloxane copolymer according to claim 1, comprising: addition reacting (A) an organopolysiloxane having silicon-bonded hydrogen atoms at both molecular terminals expressed by general formula (1') below, and (B) a compound having a carbosiloxane dendron structure that has one carbon-carbon double bond at a molecular terminal expressed by general formula (2') below at an amount less than or equal to ½ a molar equivalent of the component (A) in the presence of (C) a hydrosilylation reaction catalyst; and, thereafter, further addition reacting (D) a hydrophilic segment having one alkenyl group at a molecular terminal at an amount less than or equal to ½ a molar equivalent of the component (A), wherein the hydrophilic segment is derived from a hydrophilic compound selected from polyhydric alcohols comprising glycerin or polyglycerines, the hydrophilic segment comprising at least one hydrophilic unit selected from hydrophilic units expressed by structural formulae (3-2) to (3-4):

General Formula (1'):

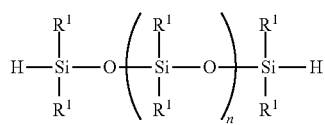

(1')

wherein $R^1$ each independently represent an aryl group or an alkyl group having from 1 to 10 carbons, and n is a number in a range of 0 to 10; and General Formula (2'):

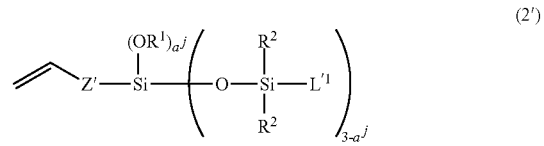

(2')

wherein $L'^1$ is a methyl group or, when j=1, is a silylalkyl group expressed by general formula (2") below, and Z' is a divalent organic group;

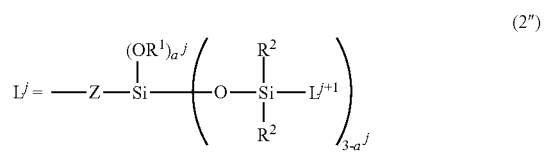

(2")

wherein $R^2$ is a phenyl group or an alkyl group having from 1 to 6 carbons, and Z is a divalent organic group; j represents a generation of the silylalkyl group represented by $L^j$ and is an integer of 1 to c' with c' being an integer from 1 to 10, and $L^{j+1}$ is the silylalkyl group when j is less than c' and is a methyl group or a phenyl group at terminal $L^{j+1}$ generations; and $a^j$ is a number in a range of 0 to 3.

14. The organopolysiloxane copolymer according to claim 1 expressed by structural formula (PI):

Structural Formula (PI)

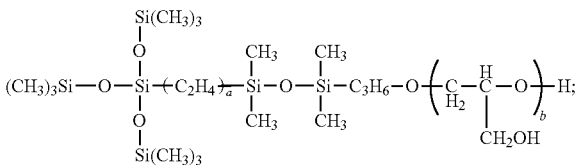

wherein a and b are selected from the group consisting of:
a=1 and b=4;
a=3 and b=4;
a=1 and b=1; and
a=1 and b=2.

* * * * *